US008513255B2

(12) United States Patent
Wunberg et al.

(10) Patent No.: US 8,513,255 B2
(45) Date of Patent: *Aug. 20, 2013

(54) SUBSTITUTED DIHYDROQUINAZOLINES

(75) Inventors: Tobias Wunberg, Hinterbruehl (AT); Judith Baumeister, Mechelen (BE); Ulrich Betz, Reinheim (DE); Mario Jeske, Solingen (DE); Thomas Lampe, Duesseldorf (DE); Susanne Nikolic, Monheim (DE); Juergen Reefschlaeger, Oldenburg (DE); Rudolf Schohe-Loop, Wuppertal (DE); Frank Suessmeier, Wuppertal (DE); Holger Zimmermann, Wuppertal (DE); Rolf Grosser, Leverkusen (DE); Kerstin Henninger, Wuppertal (DE); Guy Hewlett, Haan (DE); Joerg Keldenich, Wuppertal (DE); Dieter Lang, Velbert (DE); Peter Nell, Wuppertal (DE)

(73) Assignee: AiCuris GmbH + Co. KG., Wuppertal (DE)

( * ) Notice: Subject to any disclaimer, the term of this patent is extended or adjusted under 35 U.S.C. 154(b) by 1095 days.

This patent is subject to a terminal disclaimer.

(21) Appl. No.: 11/728,896

(22) Filed: Mar. 26, 2007

(65) Prior Publication Data

US 2007/0191387 A1    Aug. 16, 2007

Related U.S. Application Data

(62) Division of application No. 10/832,109, filed on Apr. 26, 2004, now Pat. No. 7,196,086.

(30) Foreign Application Priority Data

May 2, 2003   (DE) ................... 103 19 612

(51) Int. Cl.
*A61K 31/497*   (2006.01)
*C07D 401/00*   (2006.01)

(52) U.S. Cl.
USPC ..................... 514/252.17; 544/284

(58) Field of Classification Search
USPC ..................... 514/252.17; 544/284
See application file for complete search history.

(56) References Cited

U.S. PATENT DOCUMENTS

| | | | |
|---|---|---|---|
| 5,854,245 A | 12/1998 | Duggan et al. | |
| 7,196,086 B2 * | 3/2007 | Wunberg et al. | 514/252.17 |
| 7,271,260 B2 | 9/2007 | Lee et al. | |
| 2002/0019397 A1 | 2/2002 | Schnute et al. | |
| 2003/0216401 A1 | 11/2003 | Bentley et al. | |
| 2005/0065160 A1 | 3/2005 | Wunberg et al. | |
| 2006/0211683 A1 | 9/2006 | Selliah et al. | |
| 2006/0235032 A1 | 10/2006 | Wunberg et al. | |
| 2007/0066622 A1 * | 3/2007 | Wunberg et al. | 514/252.17 |
| 2007/0185121 A1 | 8/2007 | Wunberg et al. | |
| 2007/0281953 A1 | 12/2007 | Wunberg et al. | |
| 2008/0132515 A1 | 6/2008 | Wunberg et al. | |
| 2009/0221822 A1 * | 9/2009 | Goossen et al. | 544/292 |
| 2010/0280021 A1 | 11/2010 | Berthel et al. | |

FOREIGN PATENT DOCUMENTS

| | | |
|---|---|---|
| EP | 1201765 | 2/2002 |
| WO | WO-99/41253 | 8/1999 |
| WO | WO-2004/041790 | 5/2004 |
| WO | WO-2004/072048 | 8/2004 |
| WO | WO-2004/096778 | 11/2004 |
| WO | WO-2004/099212 | 11/2004 |

OTHER PUBLICATIONS

Martinez, A., Gil, C., Castro, A., Bruno, A., Pérez, C., Prieto, C., Otero, J., "Benzothiadiazine dioxide human cytomegalovirus inhibitors: synthesis and antiviral evaluation of main heterocycle modified derivatives," Antiviral Chem. Chemo., 14: 107-114 (2003).
Gribaudo, G., Riera, L., Lembo, D., De Andrea, M., Johnson, L., Landolfo, S., "The anticytomegaloviral activity of raltitrexed is abrogated in quiescent mouse fibroblasts that overexpress the thymidylate synthase," Virus Research, 73: 57-65 (2001).
Saito, et al., "A Facile and Efficient Carbodiimide-Mediated Synthesis of Dihydroquinazolines via a Tandem Nucleophilic Addition-Intramolecular Hetero Conjugate Addition Annulation Strategy," Tet. Letts., 37(2): 209-212 (1996).
Wang, et al., "Solid-Phase Synthesis of 3,4-Dihydroquinazoline," Tet. Letts., 38(50): 8651-8654 (1997).
U.S. Appl. No. 12/647,210.
Desai et al., Indian J. Exp. Biol. (1998) 36(12):1280-1283 (abstract).
Desai et al., Farmaco (1996) 51(5):361-366 (abstract).
Search Report from Ecuadorian Patent Application No. SP 05-6138, received Dec. 20, 2010, 1 page.
Wilson et al., Med. Chem. Res. (1992) 2:102-110 (abstract).
Griesser, Chapter 8, The Importance of Solvates (pp. 211-230), in the text, Polymorphism: In the Pharmaceutical Industry, Hilfiker, 2006.
Lee et al., Bioorganic & Medicinal Chemistry Letters (2004) 14:3379-3384.
Lischka et al., Current Opinion in Pharmacology (Article in Press, Corrected Proof) (2008) 8:1-8.
Molina et al., Synthesis (1998) 3:283-287.
Vippagunta et al., Advanced Drug Delivery Review (2001) 48:3-26.
Viral Defense Found., http://www.viraldefense.org/mission.htm, downloaded Oct. 21, 2008.
Visiting Nurse Assns. of America, http://www.vnaa.org/vnaa/gen/Germ_Protection_Center_Cold_and_Flu_Resources, downloaded Oct. 21, 2008.
Wikipedia, Maribavir, updated Feb. 10, 2009, downloaded Mar. 10, 2009 http://en.wikipedia.org/wiki/Maribavir, downloaded Mar. 10, 2009.
Xin et al., Tetrahedron Lett. (2000) 41(8):1147-1150.

* cited by examiner

*Primary Examiner* — Paul V. Ward
(74) *Attorney, Agent, or Firm* — Cozen O'Connor

(57) ABSTRACT

The invention relates to substituted dihydroquinazolines and to processes for their preparation and also to their use for preparing medicaments for the treatment and/or prophylaxis of diseases, in particular for use as antiviral agents, in particular against cytomegalo viruses.

13 Claims, No Drawings

SUBSTITUTED DIHYDROQUINAZOLINES

The invention relates to substituted dihydroquinazolines and to processes for their preparation and also to their use for preparing medicaments for the treatment and/or prophylaxis of diseases, in particular for use as antiviral agents, in particular against cytomegalo viruses.

The synthesis of dihydroquinazolines is described in Saito T., et al. *Tetrahedron Lett.,* 1996, 37, 209-212 and in Wang F., et al. *Tetrahedron Lett.,* 1997, 38, 8651-8654.

Although agents with antiviral activity and a different structure are available on the market, it is always possible for resistance to develop. Novel agents for an effective therapy are therefore desirable.

One object of the present invention is therefore to provide novel compounds having the same or improved antiviral effect for the treatment of viral infective diseases in humans and animals.

It has been found, surprisingly, that the substituted dihydroquinazolines described in the present invention have antiviral effect.

The present invention provides compounds of the formula

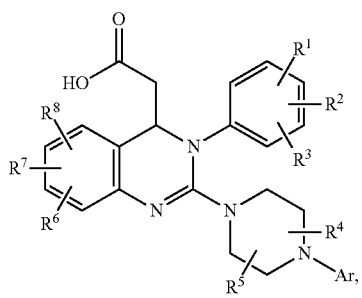

(I)

in which

Ar represents aryl which may be substituted by 1 to 3 substituents, where the substituents are selected independently of one another from the group consisting of alkyl, alkoxy, formyl, carboxyl, alkylcarbonyl, alkoxycarbonyl, trifluoromethyl, halogen, cyano, hydroxyl, amino, alkylamino, aminocarbonyl and nitro, where alkyl may be substituted by 1 to 3 substituents, where the substituents are selected independently of one another from the group consisting of halogen, amino, alkylamino, hydroxyl and aryl, or two of the substituents on the aryl radical together with the carbon atoms to which they are attached form a 1,3-dioxolane, a cyclopentane ring or a cyclohexane ring, and any third substituent present is selected independently from the group mentioned, $R^1$ represents hydrogen, amino, alkyl, alkoxy, alkylamino, alkylthio, cyano, halogen, nitro or trifluoromethyl, $R^2$ represents hydrogen, alkyl, alkoxy, alkylthio, cyano, halogen, nitro or trifluoromethyl, $R^3$ represents amino, alkyl, alkoxy, alkylamino, alkylthio, cyano, halogen, nitro, trifluoromethyl, alkylsulphonyl or alkylaminosulphonyl or one of the radicals $R^1$, $R^2$ and $R^3$ represents hydrogen, alkyl, alkoxy, cyano, halogen, nitro or trifluoromethyl and the other two together with the carbon atoms to which they are attached form a 1,3-dioxolane, a cyclopentane ring or a cyclohexane ring, $R^4$ represents hydrogen or alkyl, $R^5$ represents hydrogen or alkyl or the radicals $R^4$ and $R^5$ are attached to carbon atoms directly opposing each other in the piperazine ring and form a methylene bridge which is optionally substituted by 1 or 2 methyl groups, $R^6$ represents alkyl, alkoxy, alkylthio, formyl, carboxyl, aminocarbonyl, alkylcarbonyl, alkoxycarbonyl, trifluoromethyl, halogen, cyano, hydroxyl or nitro, $R^7$ represents hydrogen, alkyl, alkoxy, alkylthio, formyl, carboxyl, alkylcarbonyl, alkoxycarbonyl, trifluoromethyl, halogen, cyano, hydroxyl or nitro and $R^8$ represents hydrogen, alkyl, alkoxy, alkylthio, formyl, carboxyl, alkylcarbonyl, alkoxycarbonyl, trifluoromethyl, halogen, cyano, hydroxyl or nitro, and their salts, their solvates and the solvates of their salts.

Compounds according to the invention are the compounds of the formula (I)

and their salts, solvates and solvates of the salts, compounds mentioned below as embodiment(s) and their salts, solvates and solvates of the salts, unless the compounds below, embraced by formula (I), are already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

If the compounds according to the invention may exist in tautomeric forms, the present invention embraces all such tautomeric forms.

Salts which are preferred for the purposes of the present invention are physiologically acceptable salts of the compounds according to the invention. However, the invention also embraces salts which are per se not suitable for pharmaceutical applications but can be used, for example, for isolating or purifying the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of customary bases, such as, by way of example and preferably, alkali metal salts (for example sodium and potassium salts), alkaline earth metal salts (for example calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refer for the purposes of the invention to those forms of the compounds according to the invention which form a complex in the solid or liquid state by coordination with solvent molecules. Hydrates are a special form of solvates in which the coordination takes place with water.

For the purposes of the present invention, unless specified otherwise, the substituents have the following meanings:

Alkyl per se and "alk" and "alkyl" in alkoxy, alkylamino, alkylcarbonyl, alkylsulphonyl, alkylaminosulphonyl and alkoxycarbonyl are a straight-chain or branched alkyl radical having generally 1 to 6, preferably 1 to 4, particularly preferably 1 to 3, carbon atoms, by way of example and preferably methyl, ethyl, n-propyl, isopropyl, tert-butyl, n-pentyl and n-hexyl.

Alkoxy is, by way of example and preferably, methoxy, ethoxy, n-propoxy, isopropoxy, tert-butoxy, n-pentoxy and n-hexoxy.

Alkylamino is an alkylamino radical having one or two alkyl substituents (chosen independently of one another), by way of example and preferably methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino. $C_1$-$C_3$-alkylamino is, for example, a monoalkylamino radical having 1 to 3 carbon atoms or a dialkylamino radical having in each case 1 to 3 carbon atoms per alkyl substituent.

Alkylsulphonyl is, by way of example and preferably, methylsulphonyl, ethylsulphonyl, n-propyl-sulphonyl, isopropylsulphonyl, tert-butylsulphonyl, n-pentylsulphonyl and n-hexylsulphonyl.

Alkylaminosulphonyl is an alkylaminosulphonyl radical having one or two alkyl substituents (chosen independently of one another), by way of example and preferably methylaminosulphonyl, ethylaminosulphonyl, n-propylaminosulphonyl, isopropylaminosulphonyl, tert-butylaminosulphonyl, n-pentylaminosulphonyl, n-hexyl-aminosulphonyl, N,N-dimethylaminosulphonyl, N,N-diethylaminosulphonyl, N-ethyl-N-methylaminosulphonyl, N-methyl-N-n-propylaminosulphonyl, N-isopropyl-N-n-propyl-aminosulphonyl, N-tert-butyl-N-methylaminosulphonyl, N-ethyl-N-n-pentyl-aminosulphonyl and N-n-hexyl-N-methylaminosulphonyl. $C_1$-$C_3$-alkylaminosulphonyl is, for example, a monoalkylaminosulphonyl radical having 1 to 3 carbon atoms or a dialkylaminosulphonyl radical having in each case 1 to 3 carbon atoms per alkyl substituent.

Alkylcarbonyl is, by way of example and preferably, acetyl and propanoyl.

Alkoxycarbonyl is, by way of example and preferably, methoxycarbonyl, ethoxycarbonyl, n-propoxycarbonyl, isopropoxycarbonyl, tert-butoxycarbonyl, n-pentoxycarbonyl and n-hexoxy-carbonyl.

Aryl is a mono- to tricyclic aromatic carbocyclic radical having generally 6 to 14 carbon atoms; by way of example and preferably phenyl, naphthyl and phenanthrenyl.

Halogen is fluorine, chlorine, bromine and iodine, preferably fluorine and chlorine.

A symbol * on a carbon atoms means that the compound, with respect to the configuration at this carbon atom, is present in enantiomerically pure form which, for the purposes of the present invention, is to be understood as meaning an enantiomeric excess of more than 90% (>90% ee).

Preference is given to those compounds of the formula (I) in which

Ar represents phenyl which may be substituted by 1 to 3 substituents, where the substituents are selected independently of one another from the group consisting of $C_1$-$C_6$-alkyl, $C_1$-$C_6$-alkoxy, carboxyl, $C_1$-$C_6$-alkylcarbonyl, $C_1$-$C_6$-alkoxycarbonyl, trifluoromethyl, fluorine, chlorine, bromine, cyano, hydroxyl, amino, $C_1$-$C_6$-alkylamino and nitro, or two of the substituents on the phenyl radical together with the carbon atoms to which they are attached form a 1,3-dioxolane and any third substituent present is selected independently from the group mentioned, $R^1$ represents hydrogen, $C_1$-$C_3$-alkyl, $C_1$-$C_3$-alkoxy, $C_1$-$C_3$-alkylthio, fluorine or chlorine, $R^2$ represents hydrogen, $C_1$-$C_3$-alkyl, $C_1$-$C_3$-alkoxy, $C_1$-$C_3$-alkylthio, fluorine or chlorine, $R^3$ represents $C_1$-$C_4$-alkyl, cyano, fluorine, chlorine, nitro, trifluoromethyl or $C_1$-$C_3$-alkylsulphonyl, or one of the radicals $R^2$ and $R^3$ represents hydrogen, $C_1$-$C_3$-alkyl, $C_1$-$C_3$-alkoxy, cyano, halogen, nitro or trifluoromethyl and the other two together with the carbon atoms to which they are attached form a cyclopentane ring or a cyclohexane ring, $R^4$ represents hydrogen or methyl, $R^5$ represents hydrogen, $R^6$ represents $C_1$-$C_3$-alkyl, $C_1$-$C_3$-alkoxy, carboxyl, aminocarbonyl, trifluoromethyl, fluorine, chlorine, cyano, hydroxyl or nitro, $R^7$ represents hydrogen, $C_1$-$C_3$-alkyl, $C_1$-$C_3$-alkoxy, fluorine, chlorine, cyano or hydroxyl and $R^8$ represents hydrogen, $C_1$-$C_3$-alkyl, $C_1$-$C_3$-alkoxy, fluorine, chlorine, cyano or hydroxyl.

Among these, particular preference is given to those compounds of the formula (I), in which Ar represents phenyl which may be substituted by 1 or 2 substituents, where the substituents are selected independently of one another from the group consisting of methyl, methoxy, fluorine and chlorine, $R^1$ represents hydrogen, methyl, methoxy, methylthio, fluorine or chlorine, $R^2$ represents hydrogen, $R^3$ represents methyl, isopropyl, tert-butyl, cyano, fluorine, chlorine, nitro or trifluoromethyl, $R^4$ represents hydrogen, $R^5$ represents hydrogen, $R^6$ represents aminocarbonyl, fluorine, chlorine, cyano or hydroxyl, $R^7$ represents hydrogen and $R^8$ represents hydrogen, fluorine or chlorine.

Among these, particular preference is also given to those compounds of the formula (I), in which Ar represents phenyl which may be substituted by 1 or 2 substituents, where the substituents are selected independently of one another from the group consisting of methyl, methoxy, fluorine and chlorine, $R^1$ represents hydrogen, methyl, methoxy, methylthio, fluorine or chlorine, $R^2$ represents hydrogen, $R^3$ represents methyl, tert-butyl, cyano, fluorine, chlorine, nitro or trifluoromethyl, $R^4$ represents hydrogen, $R^5$ represents hydrogen, $R^6$ represents aminocarbonyl, fluorine, chlorine, cyano or hydroxyl, $R^7$ represents hydrogen and $R^8$ represents hydrogen, fluorine or chlorine.

Among these, very particular preference is given to those compounds of the formula (I), in which Ar represents phenyl which may be substituted by 1 or 2 substituents, where the substituents are selected independently of one another from the group consisting of methyl, methoxy, fluorine and chlorine, $R^1$ represents hydrogen or methoxy, $R^2$ represents hydrogen, $R^3$ represents methyl, tert-butyl, chlorine or trifluoromethyl, $R^4$ represents hydrogen, $R^5$ represents hydrogen, $R^6$ represents aminocarbonyl or fluorine, $R^7$ represents hydrogen and $R^8$ represents hydrogen or fluorine.

Preference is also given to those compounds of the formula (I), in which $R^1$ represents hydrogen, methyl, methoxy or fluorine.

Among these, particular preference is given to those compounds of the formula (I), in which $R^1$ represents methoxy.

Preference is also given to those compounds of the formula (I) in which $R^1$ is attached to the phenyl ring via the position ortho to the point of attachment of the phenyl ring. For the purposes of the present invention, the point of attachment of the phenyl ring substituted by radicals $R^1$, $R^2$ and $R^3$ is to be understood as meaning the carbon atom of the phenyl ring which, according to formula (I), is attached to one of the two nitrogen atoms of the dihydroquinazoline.

Particular preference is given to those compounds of the formula (I), in which $R^1$ represents methoxy and $R^1$ is attached to the phenyl ring via the position ortho to the point of attachment of the phenyl ring.

Preference is also given to those compounds of the formula (I) in which $R^2$ represents hydrogen.

Preference is also given to those compounds of the formula (I) in which $R^3$ represents trifluoromethyl, chlorine, methyl, isopropyl or tert-butyl.

Among these, particular preference is given to those compounds of the formula (I) in which $R^3$ represents trifluoromethyl, chlorine or methyl.

Among these, very particular preference is given to those compounds of the formula (I) in which $R^3$ represents trifluoromethyl.

Preference is also given to those compounds of the formula (I) in which $R^1$ is attached to the phenyl ring via the position ortho to the point of attachment of the phenyl ring and $R^3$ is attached to the phenyl ring via the position meta to the point of attachment of the phenyl ring, which position is opposite to that of $R^1$.

Particular preference is given to those compounds of the formula (I) in which $R^1$ is attached to the phenyl ring via the position ortho to the point of attachment of the phenyl ring, $R^3$ represents trifluoromethyl, chlorine or methyl and $R^3$ is attached to the phenyl ring via the position meta to the point of attachment of the phenyl ring, which position is opposite to that of $R^1$.

Among these, particular preference is given to those compounds of the formula (I) in which $R^1$ is attached to the phenyl ring via the position ortho to the point of attachment of the phenyl ring, $R^3$ represents trifluoromethyl and $R^3$ is attached to the phenyl ring via the position meta to the point of attachment of the phenyl ring, which position is opposite to that of $R^1$.

Preference is also given to those compounds of the formula (I) in which $R^4$ and $R^5$ represent hydrogen.

Preference is also given to those compounds of the formula (I) in which $R^6$ represents fluorine.

Particular preference is given to those compounds of the formula (I) in which $R^6$ represents fluorine and $R^6$ is, as described in formula

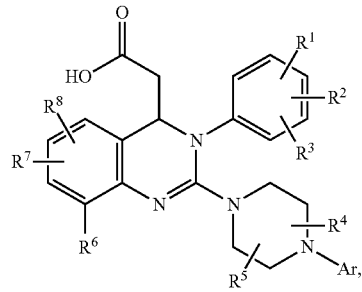

(Ia)

attached to the aromatic radical of the dihydroquinazoline.

Preference is also given to those compounds of the formula (I) in which $R^7$ represents hydrogen.

Among these, particular preference is given to those compounds of the formula (I) in which $R^8$ represents hydrogen, methyl or fluorine.

Among these, very particular preference is given to those compounds of the formula (I) in which $R^8$ represents hydrogen.

Preference is also given to those compounds of the formula (I) in which Ar represents phenyl which may be substituted by 1 or 2 substituents, where the substituents are selected independently of one another from the group consisting of methyl, methoxy, fluorine and chlorine.

The particular radical definitions given in the respective combinations or preferred combinations of radicals are, independently of the combinations of radicals given in each case, also replaced by radical definitions of other combinations.

Very particular preference is given to combinations of two or more of the preferred ranges mentioned above.

The invention furthermore provides a process for preparing the compounds of the formula (I), which comprises reacting compounds of the formula

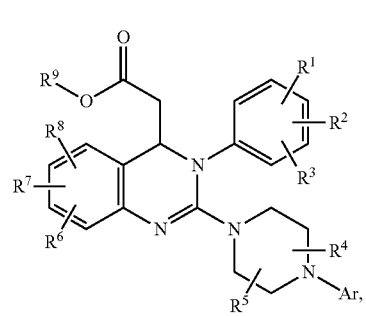

(II)

in which
Ar, $R^1$, $R^2$, $R^3$, $R^4$, $R^5$, $R^6$, $R^7$ and $R^8$ are as defined above and $R^9$ represents alkyl, preferably methyl or ethyl or tert-butyl, with bases or acids.

In the case of methyl and ethyl, the reaction is generally carried out using bases in inert solvents, preferably in a temperature range of from room temperature to the reflux temperature of the solvent, at atmospheric pressure.

Suitable bases are, for example, alkali metal hydroxides, such as sodium hydroxide, lithium hydroxide or potassium hydroxide, or alkali metal carbonates, such as caesium carbonate, sodium carbonate or potassium carbonate, if appropriate in aqueous solution; preference is given to sodium hydroxide in water.

Inert solvents are, for example, ethers, such as 1,2-dimethoxyethane, dioxane, tetrahydrofuran, glycol dimethyl ether or diethylene glycol dimethyl ether, alcohols, such as methanol, ethanol, n-propanol, isopropanol, n-butanol or tert-butanol, or mixtures of solvents; preference is given to dioxane or tetrahydrofuran.

In the case of tert-butyl, the reaction is generally carried out using acids in inert solvents, preferably in a temperature range of from 0° C. to 40° C., at atmospheric pressure.

Here, suitable acids are hydrogen chloride in dioxane, hydrogen bromide in acetic acid or trifluoroacetic acid in methylene chloride.

The compounds of the formula (H) are known or can be prepared by reacting compounds of the formula

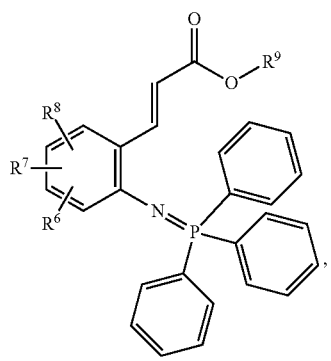

(III)

in which
$R^6$, $R^7$, $R^8$ and $R^9$ are as defined above
in a two-step reaction initially with compounds of the formula

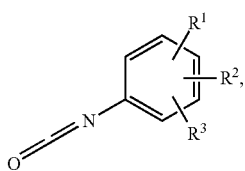

(IV)

in which
$R^1$, $R^2$ and $R^3$ are as defined above
and then with compounds of the formula

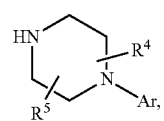

(V)

in which
Ar, $R^4$ and $R^5$ are as defined above.

Both steps of the reaction are generally carried out in inert solvents, preferably in a temperature range of from room temperature to 100° C., at atmospheric pressure. In the second step, if appropriate, silica gel is added to the reaction mixture. The reaction is preferably carried out with work-up between the first and the second step.

Suitable inert solvents are, for example, halogenated hydrocarbons, such as methylene chloride, trichloromethane, carbon tetrachloride, trichloroethane, tetrachloroethane, 1,2-dichloroethane or trichloroethylene, ethers, such as diethyl ether, methyl tert-butyl ether, 1,2-dimethoxyethane, dioxane, tetrahydrofuran, glycol dimethyl ether or diethylene glycol dimethyl ether, hydrocarbons, such as benzene, xylene, toluene, hexane, cyclohexane or mineral oil fractions, or other solvents, such as dimethylformamide, dimethylacetamide, acetonitrile or ethyl acetate, or mixtures of solvents; preference is given to methylene chloride.

The compounds of the formula (IV) are known or can be synthesized by known processes from the corresponding starting materials.

The compounds of the formula (V) are known or can be synthesized by known processes from the corresponding starting materials, for example by a Buchwald-Hartwig reaction according to the synthesis scheme below (review in: C. G. Frost, P. Mendonca, *J. Chem. Soc., Perkin Trans* 1, 1998, 2615-2623):

Buchwald-Hartwig reaction:

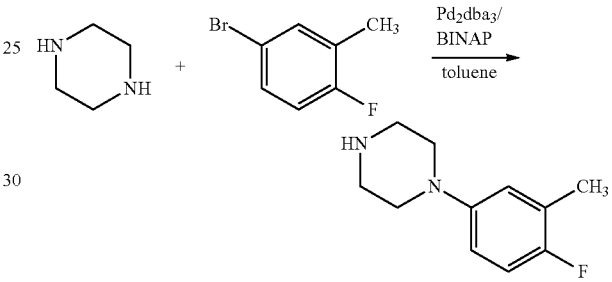

The starting materials required for this purpose are known or can be synthesized by known processes from the corresponding starting materials.

The compounds of the formula (III) are known or can be prepared by reacting compounds of the formula

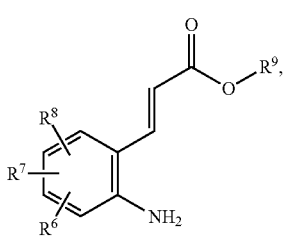

(VI)

in which
$R^6$, $R^7$, $R^8$ and $R^9$ are as defined above
with triphenylphosphine and carbon tetrachloride.

The reaction is generally carried out in inert solvents, in the presence of a base, preferably in a temperature range of from room temperature to 50° C., at atmospheric pressure.

Suitable inert solvents are, for example, ethers, such as diethyl ether, methyl tert-butyl ether, 1,2-dimethoxyethane, dioxane, tetrahydrofuran, glycol dimethyl ether or diethylene glycol dimethyl ether, hydrocarbons, such as benzene, xylene, toluene, hexane, cyclohexane or mineral oil fractions, or other solvents, such as dimethylformamide, dimethylacetamide, acetonitrile or pyridine; preference is given to acetonitrile.

Suitable bases are, for example, alkali metal and alkaline earth metal carbonates, such as caesium carbonate, sodium carbonate or potassium carbonate, or amines, such as triethylamine, diisopropylethylamine, N-methylmorpholine or pyridine; preference is given to triethylamine.

The compounds of the formula (VI) are known or can be synthesized by known processes from the corresponding starting materials, for example by a Heck reaction or a Wittig-Horner reaction, according to the synthesis schemes below:

Heck reaction:

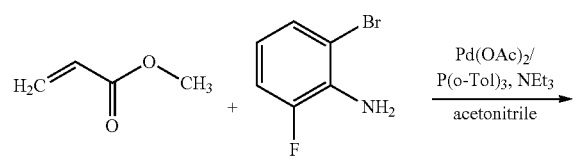

Wittig-Horner reaction:

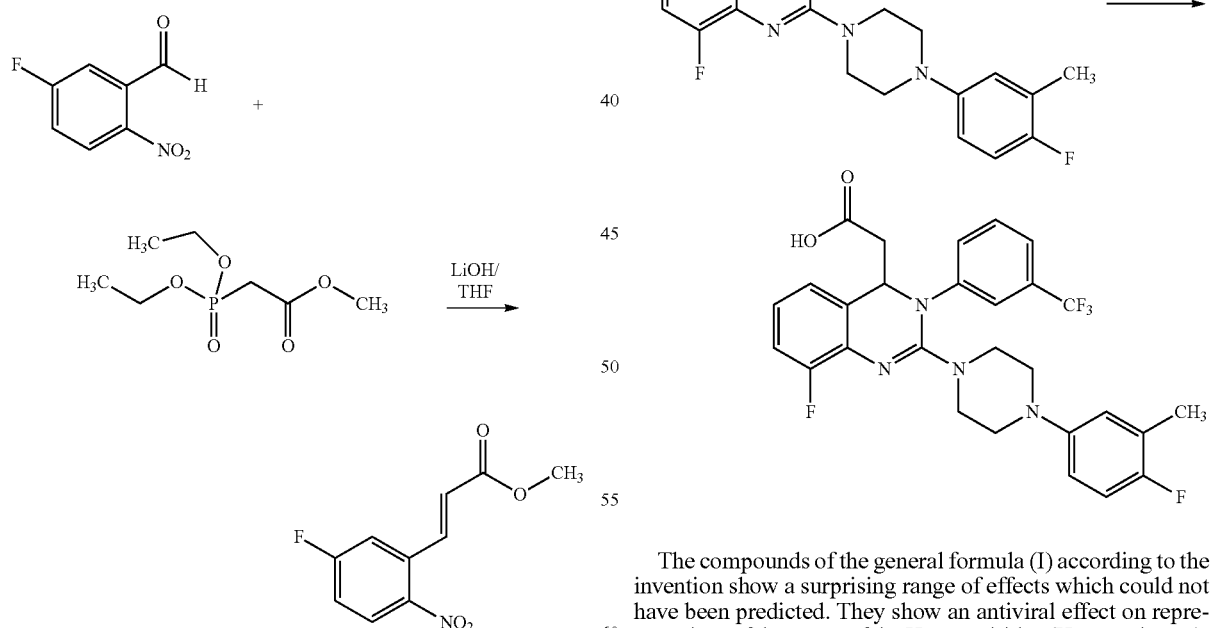

The starting materials required for this purpose are known or can be synthesized by known processes from the corresponding starting materials.

The preparation of the compounds according to the invention can be illustrated by the synthesis scheme below.

Synthesis scheme:

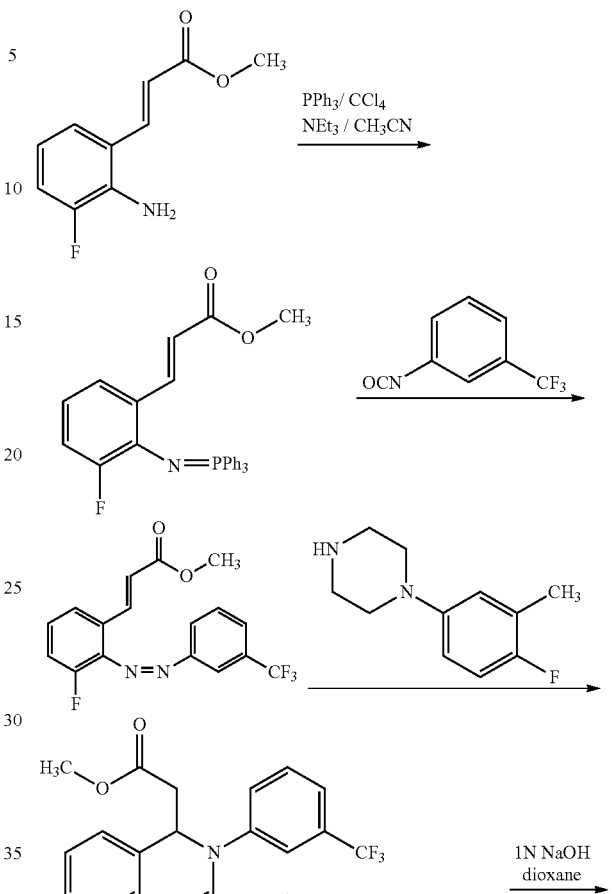

The compounds of the general formula (I) according to the invention show a surprising range of effects which could not have been predicted. They show an antiviral effect on representatives of the group of the Herpes viridae (Herpes viruses), especially on cytomegalo viruses (CMV), in particular, on human cytomegalovirus (HCMV).

Areas of indication which may be mentioned by way of example are:

1) Treatment and prophylaxis of HCMV infections in AIDS patients (retinitis, pneumonitis, gastrointestinal infections).

2) Treatment and prophylaxis of cytomegalovirus infections in bone-marrow and organ transplantations which develop often life-threatening HCMV pneumonitis or encephalitis, and gastrointestinal and systemic HCMV infections.
3) Treatment and prophylaxis of HCMV infections in neonates and infants.
4) Treatment of an acute HCMV infection in pregnant women.
5) Treatment of HCMV infection in immunosuppressed patients associated with cancer and cancer therapy.
6) Treatment of HCMV-positive cancer patients with the aim to reduce HCMV-mediated tumour progression (cf. J. Cinatl, et al., *FEMS Microbiology Reviews* 2004, 28, 59-77).

The present invention further provides the use of the compounds according to the invention for the treatment and/or prophylaxis of diseases, especially of infections with viruses, in particular the viruses mentioned above, and the infective diseases caused by these infections. Hereinbelow, a viral infection is to be understood as including both an infection with a virus and a disease caused by an infection with a virus.

The present invention also provides the use of the compounds according to the invention for the treatment and/or prophylaxis of disorders, in particular the disorders mentioned above.

The present invention also provides the use of the compounds according to the invention for preparing a medicament for the treatment and/or prophylaxis of disorders, in particular the disorders mentioned above.

The compounds according to the invention are preferably used for preparing medicaments suitable for the prophylaxis and/or treatment of infections with a representative of the group of the Herpes viridae, in particular a cytomegalovirus, in particular the human cytomegalovirus.

The present invention also provides a method for the treatment and/or prophylaxis of disorders, in particular the disorders mentioned above, using an antivirally effective amount of the compounds according to the invention.

The present invention also provides medicaments comprising at least one compound according to the invention and at least one or more further active compounds, in particular for the treatment and/or prophylaxis of the disorders mentioned above. Active compounds suitable for combinations are, by way of example and preferably: antiviral active compounds, such as gancyclovir or acyclovir.

The compounds according to the invention can act systemically and/or locally. For this purpose, they can be administered in a suitable way, such as, for example, by the oral, parenteral, pulmonary, nasal, sublingual, lingual, buccal, rectal, dermal, transdermal, conjunctival or otic route, or as implant or stent.

For these administration routes, it is possible to administer the compounds according to the invention in suitable administration forms.

Suitable for oral administration are known administration forms which deliver the compounds according to the invention rapidly and/or in modified form and which comprise the compounds according to the invention in crystalline and/or amorphous and/or dissolved form, such as, for example, tablets (uncoated or coated tablets, for example tablets provided with enteric coatings or coatings which dissolve slowly or are insoluble and which control the release of the compound according to the invention), tablets which disintegrate rapidly in the oral cavity and/or films/wafers, films/lyophylisates, capsules (for example Hart or soft gelatin capsules), sugar-coated tablets, granules, pellets, powders, emulsions, suspensions, aerosols or solutions.

Parenteral administration can take place with avoidance of an adsorption step (for example intravenously, intraarterially, intracardially, intraspinally or intralumbally) or with inclusion of absorption (for example intramuscularly, subcutaneously, intracutaneously, percutaneously or intraperitoneally). Administration forms suitable for parenteral administration are, inter alia, preparations for injection and infusion in the form of solutions, suspensions, emulsions, lyophilisates or sterile powders.

Examples suitable for other administration routes are, for example, pharmaceutical forms for inhalation (inter alia powder inhalers, nebulizers), nasal drops/solutions/sprays; tablets to be administered lingually, sublingually or buccally, films/wafers or capsules, suppositories, preparations for the eyes or ears, vaginal capsules, aqueous suspensions (lotions, shaking mixtures), lipophilic suspensions, ointments, creams, transdermal therapeutic systems, milk, pastes, foams, dusting powders, implants or stents.

The compounds according to the invention can be converted into the stated administration forms. This can take place in a known manner with the mixing of inert, non-toxic, pharmaceutically acceptable auxiliaries. These auxiliaries include, inter alia, carriers (for example microcrystalline cellulose, lactose, mannitol), solvents (for example liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (for example antioxidants such as ascorbic acid), colorants (for example inorganic pigments such as iron oxides) and flavour- and/or odour-masking agents.

The present invention furthermore provides medicaments comprising at least one compound according to the invention, usually together with one or more inert, non-toxic, pharmaceutically acceptable auxiliaries, and their use for the purposes mentioned above.

In general, it has proved advantageous to administer on intravenous administration amounts of about 0.001 to 10 mg/kg, preferably about 0.01 to 5 mg/kg, of body weight to achieve effective results, and the dosage on oral administration is about 0.01 to 25 mg/kg, preferably 0.1 to 10 mg/kg, of body weight.

It may nevertheless be necessary where appropriate to deviate from the amounts mentioned, specifically as a function of the body weight, administration route, individual response to the active compound, mode of preparation and time or interval over which administration takes place.

Thus, it may be sufficient in some cases to make do with less than the aforementioned minimal amount, whereas in other cases the upper limit mentioned must be exceeded. It may in the event of administration of larger amounts be advisable to divide these into a plurality of individual doses over the day.

The percentage data in the following tests and examples are percentages by weight unless otherwise indicated; parts or parts by weight. Solvent ratios, dilution ratios and concentration data of liquid/liquid solutions are in each case based on volume.

A. Examples

| Abbreviations: | |
|---|---|
| BINAP | 2,2'-bis(diphenylphosphino)-1,1'-binaphthyl |
| CDCl₃ | deuterated chloroform |
| DCI | direct chemical ionization (in MS) |
| DCM | dichloromethane |
| DIEA | N,N-diisopropylethylamine |
| DMSO | dimethyl sulphoxide |
| DMF | N,N-dimethylformamide |
| EA | ethyl acetate |
| EI | electron impact ionization (in MS) |
| ESI | electrospray ionization (in MS) |
| h | hour |
| HPLC | high-pressure, high-performance liquid chromatography |
| LC-MS | liquid-chromatography-coupled mass spectroscopy |
| LDA | lithium diisopropylamide |
| min | minutes |
| m.p. | melting point |
| MS | mass spectroscopy |
| MTBE | methyl tert-butyl ether |
| NMR | nuclear magnetic resonance spectroscopy |
| Pd—C | palladium-on-carbon |
| RP-HPLC | reverse phase HPLC |
| RT | room temperature |
| $R_t$ | retention time (in HPLC) |
| THF | tetrahydrofuran |
| TLC | Thin-layer chromatography |

General LC-MS and HPLC Methods:

Method 1 (analytical HPLC): column: Kromasil C18 60 mm×2 mm; temperature: 30° C.; flow rate: 0.75 ml/min; mobile phase A: 0.005 M HClO₄, mobile phase B: acetonitrile; gradient: →0.5 min 98% A, →4.5 min 10% A, →6.5 min 10% A.

Method 2 (preparative HPLC): column: GromSil C18, 250 mm×30 mm; flow rate: 50 ml/min; time per run: 38 min; detection: 210 nm; mobile phase A: water, mobile phase B: acetonitrile; gradient: 10% B (3 min)->90% B (31 min)->90% B (34 min)->10% B (34.01 min).

Method 3 (LC-MS): column: GromSil 120 ODS-4 HE, 50 mm×2.0 mm, 3 μm; mobile phase A: 1 l of water+1 ml of 50% strength formic acid, mobile phase B: 1 l of acetonitrile+1 ml of 50% strength formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 208-400 nm.

Method 4 (preparative HPLC, separation of enantiomers, carboxylic acids): column: packing chiral silica gel selector KBD 8361 (420 mm×100 mm) based on the selector poly(N-methacryloyl-L-leucine-1-menthylamide); temperature: 23° C.; mobile phase: methyl tert-butyl ether; flow rate: 100 ml/min; the compound is dissolved in methyl tert-butyl ether/ethyl acetate (9:1).

Method 5 (preparative HPLC): column: GromSil C18, 250 mm×30 mm; flow rate: 50 ml/min; time per run: 38 min; detection: 210 nm; mobile phase A: water with 0.1% formic acid, mobile phase B: acetonitrile; gradient: 10% B (3 min)->90% B (31 min)->90% B (34 min)->10% B (34.01 min).

Method 6 (analytical HPLC): instrument: HP 1100 with DAD detection; column: Kromasil RP-18, 60 mm×2 mm, 3.5 μm; mobile phase A: 5 ml of HClO₄/l of water, mobile phase B: acetonitrile; gradient: 0 min 2% B, 0.5 min 2% B, 4.5 min 90% B, 9 min 90% B; flow rate: 0.75 ml/min; temp.: 30° C.; detection: UV 210 nm.

Method 7 (LC-MC): instrument: Micromass Platform LCZ with HPLC Agilent series 1100; column: Grom-SIL120 ODS-4 HE, 50 mm×2.0 mm, 3 μm; mobile phase A: 1 l of water+1 ml of 50% strength formic acid, mobile phase B: 1 l of acetonitrile+1 ml of 50% strength formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 210 nm.

Method 8 (LC-MC): instrument: Micromass Platform LCZ, HP1100; column: Symmetry C18, 50 mm×2.1 mm, 3.5 μm; mobile phase A: acetonitrile+0.1% formic acid, mobile phase B: water+0.1% formic acid; gradient: 0.0 min 10% A→4.0 min 90% A→6.0 min 90% A; oven: 40° C.; flow rate: 0.5 ml/min; UV detection: 208-400 nm.

Method 9 (LC-MC): MS instrument: Micromass ZQ; HPLC instrument: Waters Alliance 2795; column: Merck Chromolith SpeedROD RP-18e 50 mm×4.6 mm; mobile phase A: water+500 μl of 50% strength formic acid/l, mobile phase B: acetonitrile+500 μl of 50% strength formic acid/l; gradient: 0.0 min 10% B→3.0 min 95% B→4.0 min 95% B; oven: 35° C.; flow rate: 0.0 min 1.0 ml/min→3.0 min 3.0 ml/min→4.0 min 3.0 ml/min; UV detection: 210 nm.

Method 10 (LC-MC): MS instrument: Micromass ZQ; HPLC instrument: HP 1100 Series; UV DAD; column: Grom-Sil 120 ODS-4 HE 50 mm×2 mm, 3.0 μm; mobile phase A: water+500 μl of 50% strength formic acid/l, mobile phase B: acetonitrile+500 μl of 50% strength formic acid/l; gradient: 0.0 min 0% B→2.9 min 70% B→3.1 min 90% B→4.5 min 90% B; oven: 50° C.; flow rate: 0.8 mL/min; UV detection: 210 nm.

Method 11 (preparative HPLC, separation of enantiomers): column: packing chiral silica gel selector KBD 8361 (250 mm×20 mm) based on the selector poly(N-methacryloyl-L-leucine-1-menthylamide); temperature: 23° C.; mobile phase: methyl tert-butyl ether+5% ethyl acetate; flow rate: 25 ml/min.

Method 12 (preparative HPLC, separation of enantiomers): column: packing chiral silica gel selector KBD 5326 (250 mm×20 mm) based on the selector poly(N-methacryloyl-L-leucine-dicyclopropylmethylamide); temperature: 23° C.; mobile phase: methyl tert-butyl ether+5% ethyl acetate; flow rate: 25 ml/min.

Method 13 (preparative HPLC, separation of enantiomers): column: packing chiral silica gel selector KBD 8361 (250 mm×20 mm) based on the selector poly(N-methacryloyl-L-leucine-1-menthylamide); temperature: 23° C.; mobile phase: methyl tert-butyl ether; flow rate: 25 ml/min.

Method 14 (preparative HPLC, separation of enantiomers, esters): column: packing chiral silica gel selector KBD 8361 (420 mm×100 mm) based on the selector poly(N-methacryloyl-L-leucine-1-menthylamide); temperature: 23° C.; mobile phase: isohexane/ethyl acetate 85/15 v/v; flow rate: 100 ml/min; the compound is dissolved in isohexane/ethyl acetate (85:15).

Method 15 (preparative HPLC, separation of enantiomers, esters): column: packing chiral silica gel selector KBD 8361 (420 mm×100 mm) based on the selector poly(N-methacryloyl-L-leucine-1-menthylamide); temperature: 23° C.; mobile phase: methyl tert-butyl ether; flow rate: 100 ml/min; the compound is dissolved in methyl tert-butyl ether.

Method 16 (LC-MS): instrument: Micromass Platform LCZ with HPLC Agilent Series 1100; column: Grom-SIL120 ODS-4 HE, 50 mm×2.0 mm, 3 μm; mobile phase A: 1 l of water+1 ml of 50% strength formic acid, mobile phase B: 1 l of acetonitrile+1 ml of 50% strength formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 208-400 nm.

Method 17 (LC-MS): MS instrument: Micromass ZQ; HPLC instrument: Waters Alliance 2790; column: Grom-Sil 120 ODS-4 HE 50 mm×2 mm, 3.0 μm; mobile phase A: water+500 μl of 50% strength formic acid/1, mobile phase B: acetonitrile+500 μl of 50% strength formic acid/l; gradient: 0.0 min 0% B→0.2 min 0% B→2.9 min 70% B→3.1 min 90% B→4.5 min 90% B; oven: 45° C.; flow rate: 0.8 ml/min; UV detection: 210 nm.

Starting Materials

General Procedure [A]: Synthesis of Substituted 2-aminocinnamic Acid Derivatives by Heck Coupling from 2-Halo-Substituted Anilines In a one-necked flask, 1.0 equivalent of an aryl halide is initially charged with 1.6 equivalents of methyl acrylate or tert-butyl acrylate, 2.0 equivalents of triethylamine, 0.03 equivalents of palladium(II) acetate and 0.03 equivalents of tri-o-tolylphosphine in acetonitrile (solution about 1M). The mixture is stirred under reflux for 48 hours. After the reaction has ended (the reaction is monitored by TLC), the solvent is removed. The residue is purified chromatographically on silica gel using cyclohexane/ethyl acetate=8:2 v/v.

Example 1A

Methyl (2E)-3-[2-amino-3-fluorophenyl]propenoate

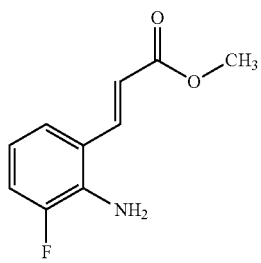

Starting with 42.00 g (221.04 mmol) of 2-bromo-6-fluoroaniline, the general procedure [A] gives 29.66 g (68% of theory) of product.

HPLC (Method 1): $R_t$=4.14 min
MS (ESI-pos): m/z=196 (M-41)$^+$

Example 2A

Methyl 2-amino-3-[(1E)-3-methoxy-3-oxo-1-propenyl]benzoate

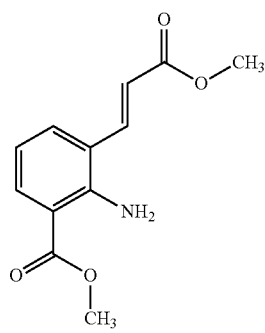 [SMILES: COC(=O)/C=C/c1cccc(C(=O)OC)c1N]

Starting with 2.00 g (8.69 mmol) of methyl 2-amino-3-bromobenzoate, the general procedure [A] gives 1.29 g (60% of theory) of product.

HPLC (Method 1): $R_t$=4.42 min
MS (ESI-pos): m/z=236 (M+H)$^+$

Example 3A

Methyl (2E)-3-(2-amino-3,5-difluorophenyl)-2-propenoate

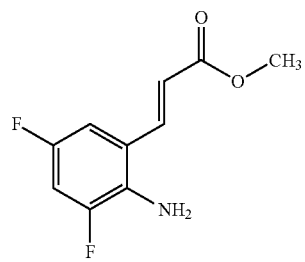

Starting with 3.00 g (14.42 mmol) of 2-bromo-4,6-difluoroaniline, the general procedure [A] gives 1.41 g (45% of theory) of product.

HPLC (Method 1): $R_t$=4.23 min
MS (ESI-pos): m/z=214 (M+H)$^+$

Example 4A

Methyl 4-amino-3-[(1E)-3-methoxy-3-oxo-1-propenyl]benzoate

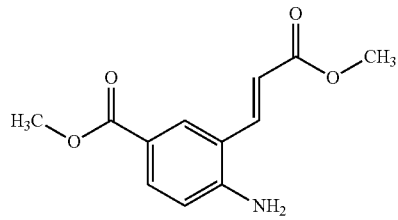

Starting with 25.00 g (90.23 mmol) of methyl 4-amino-3-iodobenzoate, the general procedure [A] gives 24.31 g (92% of theory) of product.

HPLC (Method 1): $R_t$=4.71 min
MS (ESI-pos): m/z=278 (M+H)$^+$

Example 5A

Methyl (2E)-3-[2-amino-5-cyanophenyl]-2-propenoate

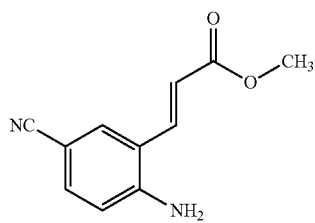

Starting with 1.90 g (9.64 mmol) of 3-bromo-4-aminobenzonitrile, the general procedure [A] gives 1.28 g (50% of theory) of product.

HPLC (Method 1): $R_t$=2.85 min

MS (DCI-pos): m/z=220 (M+NH$_4$)$^+$

General Procedure [B]: Synthesis of Substituted 2-Nitrocinnamic Acid Derivatives by Wittig-Horner Reaction from 2-Halo-Substituted Benzaldehydes In a 100 ml one-necked flask, 27.5 mmol of methyl diethyl phosphonoacetate, 25.0 mmol of the benzaldehyde and 27.5 mmol of lithium hydroxide are suspended in tetrahydrofuran. After the reaction has ended (the reaction is monitored by TLC), the reaction mixture is mixed with the same volume of water. The aqueous phase is extracted three times with ethyl acetate. The combined organic phases are washed with saturated sodium chloride solution and dried over sodium sulphate, and the solvent is removed. The product is dried under high vacuum at RT, without further purification. If the product is very impure, it is, if appropriate, purified by column chromatography on silica gel using cyclohexane/ethyl acetate.

Example 6A

Methyl (2E)-3-(3-methoxy-2-nitrophenyl)-2-propenoate

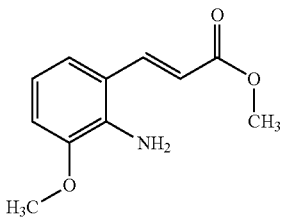

Starting with 2.00 g (11.04 mmol) of 3-methoxy-2-nitrobenzaldehyde, the general procedure [B] gives 2.46 g (92% of theory) of product.

HPLC (Method 1): $R_t$=4.37 min

MS (ESI-pos): m/z=238 (M+H)$^+$

Example 7A

Methyl (2E)-3-(5-fluoro-2-nitrophenyl)-2-propenoate

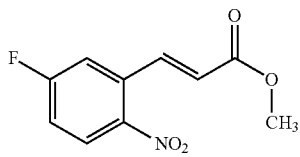 [SMILES: COC(=O)/C=C/c1cc(F)ccc1[N+](=O)[O-]]

Starting with 20.0 g (118.3 mmol) of 5-fluoro-2-nitrobenzaldehyde, the general procedure [B] gives 7.25 g (27% of theory) of product.

MS (DCI): m/z=243 (M+NH$_4$)$^+$

General Procedure [C]: Preparation of a 2-Nitrobenzaldehyde from a Benzyl Halide 10.0 mmol of the benzyl halide, 4.1 g of molecular sieve 4 Å and 20.0 mmol of N-methylmorpholine N-oxide are suspended in 45 ml of acetonitrile. The mixture is stirred at RT until the reaction has gone to completion (the reaction is monitored by TLC). After the reaction has ended, the molecular sieve is filtered off, the solvent is removed and the residue is taken up again in ethyl acetate. This solution is initially washed with 1N hydrochloric acid and then with saturated sodium chloride solution. The organic phase is separated off and then dried over sodium sulphate, and the solvent is again removed. Analysis shows that the crude product is sufficiently pure and can directly be reacted further.

Example 8A

2-Fluoro-6-nitrobenzaldehyde

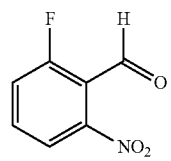

Starting with 2.00 g (8.55 mmol) of 3-fluoro-6-nitrobenzyl bromide, the general procedure [C] gives 1.09 g (75% of theory) of product.

HPLC (Method 1): $R_t$=3.58 min

General procedure [D]: Reduction of the Nitro Group of the 2-Nitrocinnamic Acid Derivatives Under argon, 25 mmol of the nitro compound and 125 mmol of tin(II) chloride dihydrate are initially charged in 60 ml of absolute ethanol in a 250 ml two-necked flask. This suspension is stirred under reflux for 30 minutes, and a clear solution is formed. The solution is then cooled to room temperature and subsequently poured onto ice-water. Using either solid sodium bicarbonate or a saturated sodium carbonate solution, the pH is adjusted to pH=7-8. 60 ml of ethyl acetate are then added, and the precipitated tin salts are filtered off through kieselguhr (a layer of a thickness of about 1 cm). The organic phase is separated off and the aqueous phase is re-extracted with ethyl acetate. The organic phases are combined, washed once with saturated sodium chloride solution and dried over sodium sulphate, and the solvent is concentrated to about half of its original volume. Activated carbon corresponding to 1% of the weight of the nitro compound is then added, and the mixture is heated under reflux for 30 minutes (the colour of the solution changes). The activated carbon is filtered off and the solvent is removed.

The residue obtained is an oil which, on drying at RT under high vacuum, forms crystals. Without further purification, the product is directly used for the next step.

Example 9A

Methyl 3-[2-amino-6-fluorophenyl]propenoate

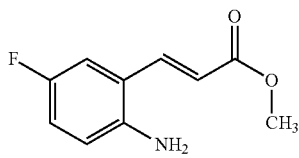

Starting with 7.25 g (32.2 mmol) of the nitro compound from Example 7A, the general procedure [D] gives 5.0 g (58% of theory) of product.

HPLC (Method 1): $R_t$=3.33 min

General Procedure [E]: Synthesis of the Iminophosphoranes by Appel Reaction of the Substituted Anilines In a 50 ml one-necked flask, 10.0 mmol of the amine of the 2-aminocinnamic ester, 20.0 mmol of triphenylphosphine, 100.0 mmol of carbon tetrachloride and 100.0 mmol of triethylamine are dissolved in 20 ml of acetonitrile. The mixture is stirred at room temperature for 2 hours. After the reaction has ended (the reaction is monitored by TLC or analytic HPLC), the solvent is removed under reduced pressure and the residue is purified by column chromatography on silica gel using cyclohexane/ethyl acetate=7:3.

Example 10A

Methyl (2E)-3-{3-fluoro-2-[(triphenylphosphoranyl idene)amino]phenyl}propenoate

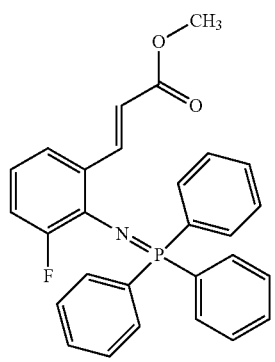 [SMILES: COC(=O)/C=C/c1cccc(F)c1N=P(c1ccccc1)(c1ccccc1)c1ccccc1]

Starting with 29.3 g (150.1 mmol) of the amine compound from Example 1A, the general procedure [E] gives 55.0 g (80% of theory) of product.

HPLC (Method 1): $R_t$=4.46 min
MS (ESI-pos): m/z=456 (M+H)$^+$

Example 11A

Methyl (2E)-3-{5-fluoro-2-[(triphenylphosphoranylidene)amino]phenyl}propenoate

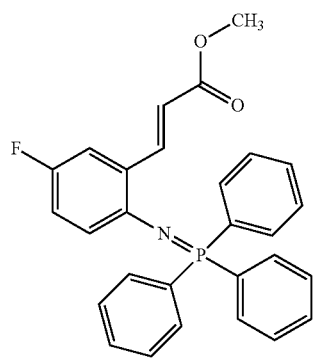 [SMILES: COC(=O)/C=C/c1cc(F)ccc1N=P(c1ccccc1)(c1ccccc1)c1ccccc1]

Starting with 50.0 g (256.2 mmol) of the amine compound from Example 9A, the general procedure [E] gives 89.6 g (77% of theory) of product.

HPLC (Method 1): $R_t$=4.36 min
MS (ESI-pos): m/z=456 (M+H)$^+$

Example 12A

Methyl (2E)-3-{5-cyano-2-[(triphenylphosphoranylidene)amino]phenyl}propenoate

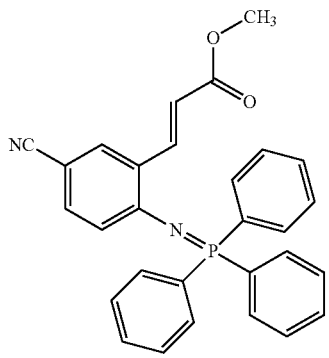 [SMILES: COC(=O)/C=C/c1cc(C#N)ccc1N=P(c1ccccc1)(c1ccccc1)c1ccccc1]

Starting with 1.24 g (4.60 mmol) of the amine compound from Example 5A, the general procedure [E] gives 2.12 g (92% of theory) of product.

HPLC (Method 1): $R_t$=4.42 min
MS (ESI-pos): m/z=463 (M+H)$^+$

General Procedure [F]: Synthesis of Phenylpiperazines by the Buchwald-Hartwig Reaction To prepare for the reaction, the reaction flask is thoroughly dried by heating under high vacuum and vented with argon. 1.0 equivalent of the bromoaryl compound and 6.0 equivalents of piperazine in absolute toluene are initially charged in the flask (0.2-0.3M solution of the bromo compound). 0.01 equivalent of tris(dibenzylideneacetone)dipalladium and 0.03 equivalent of BINAP are then added. The reaction mixture is stirred under reflux for 16 h. The mixture is then extracted once with water, the organic phase is extracted twice with 1N hydrochloric acid and the aqueous phase is adjusted to pH 8 using 1N aqueous sodium hydroxide solution and extracted three times with dichloromethane. The combined organic phases are dried over sodium sulphate and filtered, the solvent is removed under reduced pressure and the product is dried under high vacuum overnight.

Example 13A

N-(4-Fluoro-3-methylphenyl)piperazine

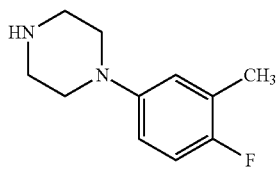

Starting with 5.0 g (26.5 mmol) of 4-fluoro-3-methyl-1-bromobenzene, the general procedure [F] gives 4.52 g (83% of theory) of product.
HPLC (Method 1): $R_1$=3.54 min
MS (ESI pos): m/z=195 (M+H)$^+$ Example 14A N-(4-Fluorophenyl)-3-methylpiperazine

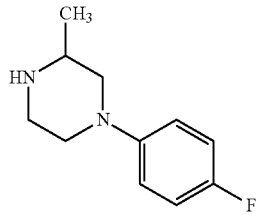

Starting with 1.0 g (5.71 mmol) of 4-fluoro-3-methyl-1-bromobenzene, the general procedure [F] gives 0.57 g (49% of theory) of product.
HPLC (Method 1): $R_t$=3.37 min
MS (DCI pos): m/z=195 (M+H)$^+$ Example 15A 1-(3-Fluorophenyl)piperazine

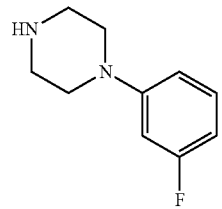 [SMILES: Fc1cccc(N2CCNCC2)c1]

1 g (5.71 mmol) of 3-fluorobromobenzene and 2.95 g (34.29 mmol) of piperazine are dissolved in 20 ml of toluene, and 0.77 g (8 mmol) of sodium tert-butoxide is added. In the presence of 0.11 g (0.17 mmol) of BINAP and 0.05 g (0.06 mmol) of tris(dibenzylideneacetone)dipalladium, the mixture is then stirred under reflux overnight. After cooling, ethyl acetate is added and the mixture is washed with water. The mixture is then extracted with 1N hydrochloric acid, and the aqueous phase is washed with ethyl acetate. The pH is adjusted to 8-9 and the mixture is then extracted with dichloromethane. The organic phase is dried over magnesium sulphate and the solvent is removed, giving the target compound.
Yield: 0.8 g (78% of theory)
HPLC (Method 1): $R_t$=3.4 min
MS (ESI-pos): m/z=181 (M+H)$^+$ Example 16A 1-(3,4-Difluorophenyl)piperazine

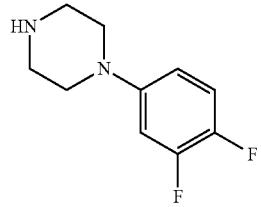 [SMILES: Fc1ccc(N2CCNCC2)cc1F]

In 100 ml of toluene, 5 g (25.91 mmol) of 3,4-difluorobromobenzene, 13.39 g (155.45 mmol) of piperazine, 3.49 g (36.27 mmol) of sodium tert-butoxide, 0.24 g (0.26 mmol) of tris(dibenzylidene-acetone)dipalladium and 0.48 g (0.78 mmol) of BINAP are stirred under reflux overnight. Ethyl acetate is added, the mixture is then washed with water and the organic phase is extracted with 1N hydrochloric acid. The aqueous phase is then washed with ethyl acetate and subsequently adjusted to pH 8. Using dichloromethane, the product is extracted from the aqueous phase. The extract is then dried over magnesium sulphate, the solvent is removed and the target compound is dried under reduced pressure.
Yield: 3.85 g (75% of theory)
HPLC (Method 1): $R_t$=3.4 min
MS (DCI): m/z=199 (M+H)$^+$ Example 17A 2-Isocyanato-1-methoxy-4-(trifluoromethyl)benzene

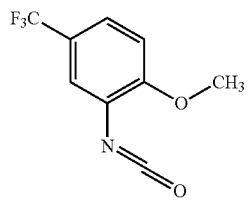

3 g (15.69 mmol) of 2-methoxy-5-trifluoromethylaniline are dissolved in 100 ml of dichloromethane, and 6.73 g (31.39 mmol) of 1,8-bis(dimethylamino)naphthalene are added. At 0-5° C., 2.24 g (11.3 mmol) of trichloromethyl chloroformate, dissolved in 50 ml of dichloromethane, are added dropwise, and the mixture is stirred at 0° C. for 30 min and then at room temperature for 60 min. At 0° C., the mixture is washed with 1N hydrochloric acid, ice-water and sodium bicarbonate solution. Drying over magnesium sulphate and removal of the solvent by distillation gives the product. The isocyanate is then used for the subsequent reactions without further purification.

Yield: 3.00 g (88% of theory)

Example 18A

Methyl (2E)-3-{3-fluoro-2-[({[2-methoxy-5-(trifluoromethyl)phenyl]imino}methylene)amino]-phenyl}-2-propenoate

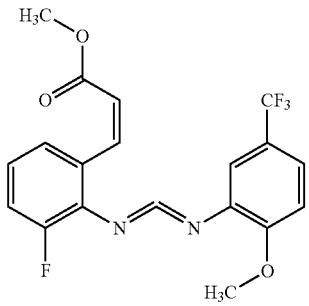 [SMILES: COC(=O)/C=C\c1cccc(F)c1N=C=Nc1cc(C(F)(F)F)ccc1OC]

5.0 g (10.98 mmol) of methyl (2E)-3-{3-fluoro-2-[(triphenylphosphoranylidene)amino]phenyl}-2-propenoate (Example 10A) are initially charged in 50 ml of dichloromethane, and the mixture is stirred with 2.5 g (11.53 mmol) of 2-isocyanato-1-methoxy-4-(trifluoromethyl)benzene (Example 17A) at room temperature overnight. The solvent is removed by distillation and the product is then purified by chromatography on silica gel (isohexane/dichloromethane 2:1; 1:1) and recrystallized from isohexane.

Yield: 2.69 g (62% of theory)
HPLC (Method 1): $R_t$=5.6 min
MS (ESI-pos): m/z=395 (M+H)$^+$ General procedure [G]: Reaction of the Iminophosphorane with an Isocyanate and Subsequent Reaction with an Amine to Give the Dihydroquinazoline Derivative 1.0 equivalent of the iminophosphorane is dissolved in 20 ml of dichloromethane (0.1-0.2M solution). 1.05 equivalents of a substituted isocyanate are then added, and the mixture is stirred at RT until the reaction has ended. The reaction is monitored by TLC or by analytical HPLC.

1.0 equivalent of amine and a spatula tip of silica gel are then added to the resulting solution of the carbodiimide and dichloromethane, and the mixture is stirred at room temperature until the reaction has gone to completion. After the reaction has ended (reaction is monitored by TLC or HPLC), the mixture is concentrated and purified by preparative HPLC on an RP phase.

In certain cases, the NMR shows the presence of a varying proportion of non-cyclized reaction product. In those cases, the mixture of cyclized and non-cyclized product is taken up in dioxane, a spatula tip of silica gel is added and the mixture is stirred under reflux for 30 min to 16 h. The silica gel is filtered off and the solution is used for further reactions.

If it is intended to produce enantiomerically pure compounds, the chromatographic separation is carried out at this stage.

Example 19A

Methyl {8-fluoro-2-[4-(4-fluorophenyl)-1-piperazinyl]-3-[3-(trifluoromethyl)phenyl]-3,4-dihydro-4-quinazolinyl}acetate

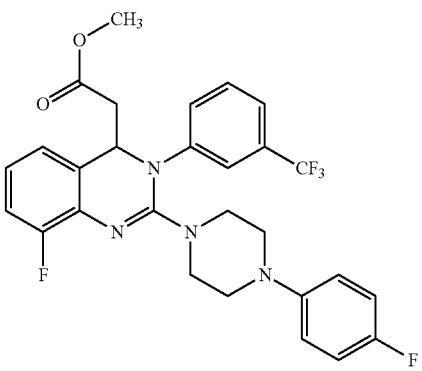 [SMILES: COC(=O)CC1c2cccc(F)c2N=C(N2CCN(c3ccc(F)cc3)CC2)N1c1cccc(C(F)(F)F)c1]

Starting with 92.5 mg (0.2 mmol) of the iminophosphorane from Example 10A, the general procedure [G] gives 50 mg (45% of theory) of product.

HPLC (Method 1): $R_t$=4.81 min

Example 20A

Methyl {8-fluoro-2-[4-(4-fluorophenyl)-1-piperazinyl]-3-[3-(trifluoromethyl)phenyl]-3,4-dihydro-4-quinazolinyl}acetate

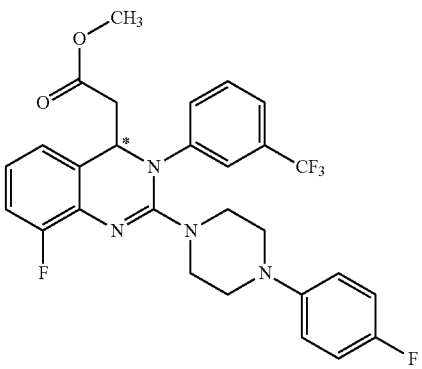 [SMILES: COC(=O)CC1c2cccc(F)c2N=C(N2CCN(c3ccc(F)cc3)CC2)N1c1cccc(C(F)(F)F)c1]

This compound is obtained as enantiomer A following the separation of enantiomers of 3.84 g of Example 19A (715 mg, 14% of theory).

HPLC (Method 1): $R_t$=4.81 min
MS (ESI-pos): m/z=544.9 (M+H)$^+$

Example 21A

Methyl {6-fluoro-2-[4-(4-fluorophenyl)-1-piperazinyl]-3-[3-(trifluoromethyl)phenyl]-3,4-dihydro-4-quinazolinyl}acetate

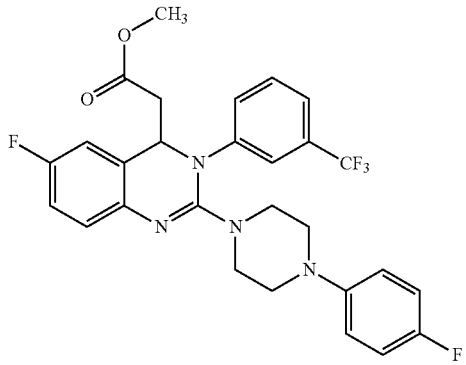 [SMILES: COC(=O)CC1c2cc(F)ccc2N=C(N2CCN(c3ccc(F)cc3)CC2)N1c1cccc(C(F)(F)F)c1]

Starting with 100 mg (0.28 mmol) of the iminophosphorane from Example 11A, the general procedure [G] gives 58 mg (39% of theory) of product.

HPLC (Method 1): $R_t$=4.80 min

Example 22A

Methyl {6-fluoro-2-[4-(4-fluorophenyl)-1-piperazinyl]-3-[3-(trifluoromethyl)phenyl]-3,4-dihydro-4-quinazolinyl}acetate

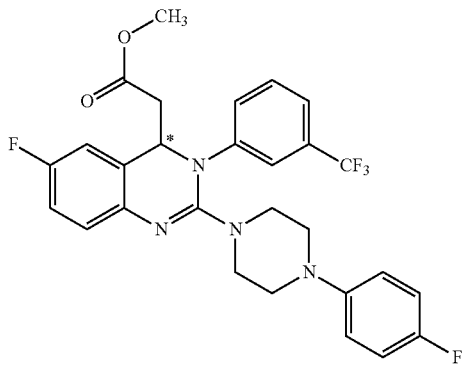 [SMILES: COC(=O)CC1c2cc(F)ccc2N=C(N2CCN(c3ccc(F)cc3)CC2)N1c1cccc(C(F)(F)F)c1]

This compound is obtained as enantiomer A following the separation of enantiomers of 832 mg of Example 21A (368 mg, 17% of theory).

HPLC (Method 1): $R_t$=4.77 min
MS (ESI-pos): m/z=544.9 (M+H)$^+$

Example 23A

Methyl {8-fluoro-2-[4-(3-methylphenyl)-1-piperazinyl]-3-[3-(trifluoromethyl)phenyl]-3,4-dihydro-4-quinazolinyl}acetate

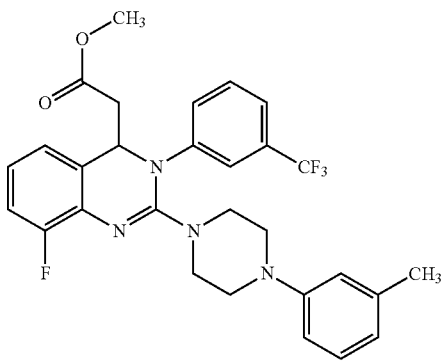 [SMILES: COC(=O)CC1c2cccc(F)c2N=C(N2CCN(c3cccc(C)c3)CC2)N1c1cccc(C(F)(F)F)c1]

Starting with 93 mg (0.2 mmol) of the iminophosphorane from Example 10A, the general procedure [G] gives 43 mg (39% of theory) of product.

HPLC (Method 1): $R_t$=4.80 min
MS (ESI-pos): m/z=541.0 (M+H)$^+$

Example 24A

Methyl {8-fluoro-2-[4-(3-methylphenyl)-1-piperazinyl]-3-[3-(trifluoromethyl)phenyl]-3,4-dihydro-4-quinazolinyl}acetate

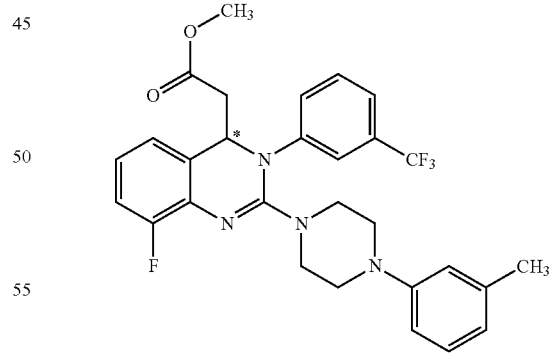

This compound is obtained as enantiomer A following the separation of enantiomers of 3.31 g of Example 23A (1.18 g, 22% of theory).

HPLC (Method 1): $R_t$=4.80 min
MS (ESI-pos): m/z=541.0 (M+H)$^+$

Example 25A

Methyl {8-fluoro-2-[4-(3-methoxyphenyl)-1-piperazinyl]-3-[3-(trifluoromethyl)phenyl]-3,4-dihydro-4-quinazolinyl}acetate

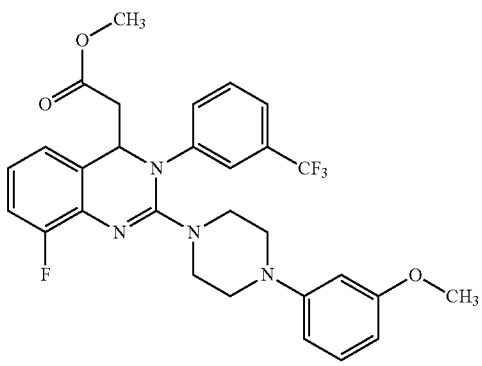 [SMILES: COC(=O)CC1c2cccc(F)c2N=C(N2CCN(c3cccc(OC)c3)CC2)N1c1cccc(C(F)(F)F)c1]

Starting with 93 mg (0.2 mmol) of the iminophosphorane from Example 10A, the general procedure [G] gives 51 mg (45% of theory) of product.

HPLC (Method 1): $R_t$=4.62 min

MS (ESI-pos): m/z=556.7 (M+H)$^+$

Example 26A

Methyl {8-fluoro-2-[4-(3-methoxyphenyl)-1-piperazinyl]-3-[3-(trifluoromethyl)phenyl]-3,4-dihydro-4-quinazolinyl}acetate

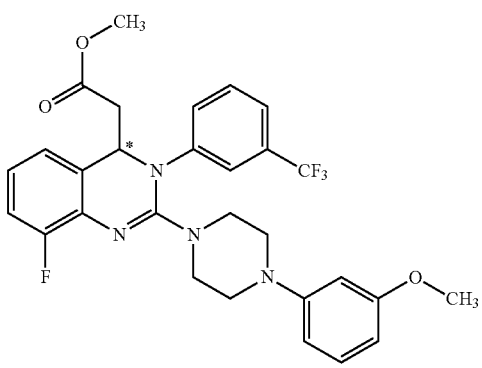 [SMILES: COC(=O)CC1c2cccc(F)c2N=C(N2CCN(c3cccc(OC)c3)CC2)N1c1cccc(C(F)(F)F)c1]

This compound is obtained as enantiomer A following the separation of enantiomers of 5.11 g of Example 25A (0.49 g, 9% of theory).

HPLC (Method 1): $R_t$=4.71 min

MS (ESI-pos): m/z=556.8 (M+H)$^+$

Example 27A

Methyl {8-fluoro-2-[4-(4-fluoro-3-methylphenyl)-1-piperazinyl]-3-[6-methoxy-3-(trifluoromethyl)-phenyl]-3,4-dihydro-4-quinazolinyl}acetate

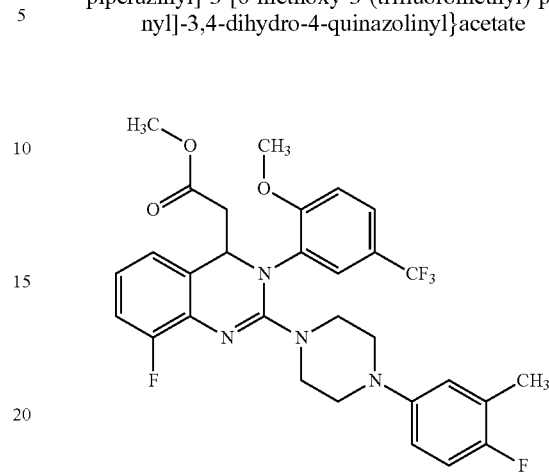

Starting with 1.0 g (2.2 mmol) of the iminophosphorane from Example 10A, 500 mg (2.31 mmol) of 2-isocyanato-1-methoxy-4-(trifluoromethyl)benzene (Example 17A) and 427 mg (2.2 mmol) of the phenylpiperazine from Example 13A, 1.03 g (79% of theory) of crude product are obtained following filtration through silica gel (cyclohexane/ethyl acetate 2:1 (v/v)). This product is reacted further without further purification.

LC-MS (Method 3): $R_t$=2.55 min, 2.66 min

MS (ESI-pos): m/z=589.3 (M+H)$^+$

Example 28A

Methyl {8-fluoro-2-[4-(4-fluoro-3-methylphenyl)-1-piperazinyl]-3-[6-methoxy-3-methylphenyl]-3,4-dihydro-4-quinazolinyl}acetate

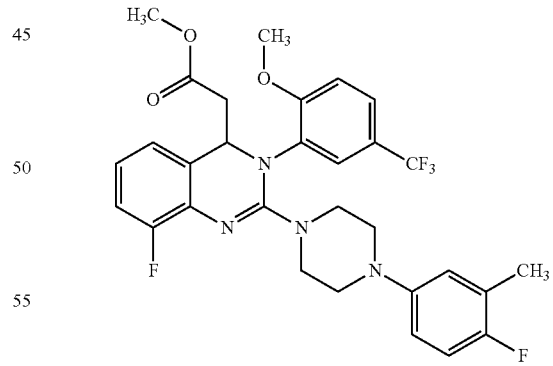

Starting with 0.60 g (1.76 mmol) of the iminophosphorane from Example 10A, 376 mg (2.31 mmol) of 2-methoxy-5-methylphenyl isocyanate and 342 mg (1.76 mmol) of the phenylpiperazine from Example 13A, 183 mg (16% of theory) of product are obtained after purification by preparative HPLC.

HPLC (Method 1): $R_t$=4.77 min

MS (ESI-pos): m/z=535.2 (M+H)$^+$

Example 29A

Methyl {8-fluoro-2-[4-(4-fluorophenyl)-1-piperazinyl]-3-[6-methoxy-3-chlorophenyl]-3,4-dihydro-4-quinazolinyl}acetate

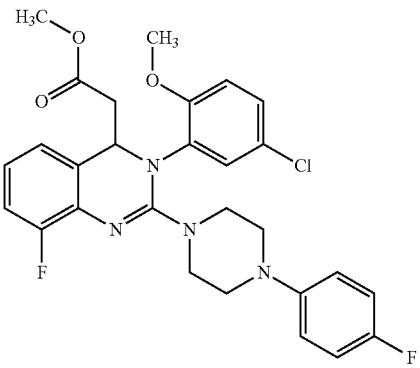

Starting with 1.0 g (2.2 mmol) of the iminophosphorane from Example 10A, 423 mg (2.31 mmol) of 2-methoxy-5-chlorophenyl isocyanate and 396 mg (2.2 mmol) of 4-fluorophenylpiperazine, 621 mg (52% of theory) of product are obtained after purification by preparative HPLC.

HPLC (Method 1): $R_t$=4.75 min
MS (ESI-pos): m/z=541.2 (M+H)$^+$

Example 30A

Methyl {8-fluoro-2-[4-(4-fluorophenyl)-1-piperazinyl]-3-[2-methoxy-5-(trifluoromethyl)phenyl]-3,4-dihydro-4-quinazolinyl}acetate

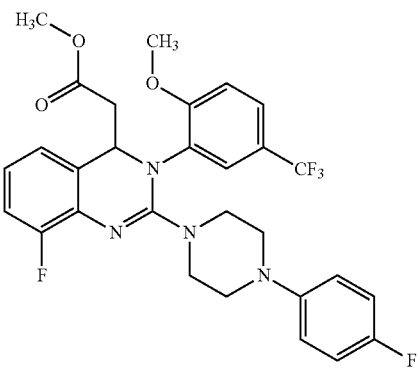 [SMILES: COC(=O)CC1c2cccc(F)c2N=C(N2CCN(c3ccc(F)cc3)CC2)N1c1cc(C(F)(F)F)ccc1OC]

550 mg (1.39 mmol) of methyl (2E)-3-{3-fluoro-2-[({[2-methoxy-5-(trifluoromethyl)phenyl]-imino}methylene)amino]phenyl}-2-propenoate (Example 18A) and 251 mg (1.39 mmol) of 1-(4-fluorophenyl)piperazine are stirred in the presence of a spatula tip of silica gel in 15 ml of dichloromethane for 1 hour. After 90 hours of stirring under reflux, the product is purified by chromatography on silica gel (dichloromethane, dichloromethane/ethyl acetate 10:1).

Yield: 769 mg (96% of theory)
HPLC (Method 1): $R_t$=4.8 min
MS (ESI-pos): m/z=575 (M+H)$^+$

Example 31A

Methyl {8-fluoro-2-[4-(3-methoxyphenyl)-1-piperazinyl]-3-[2-methoxy-5-(trifluoromethyl)-phenyl]-3,4-dihydro-4-quinazolinyl}acetate

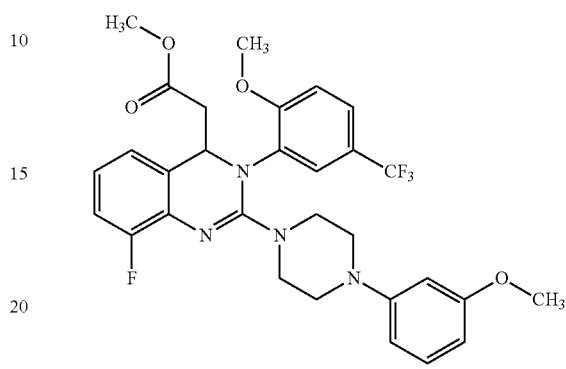

700 mg (1.78 mmol) of methyl (2E)-3-{3-fluoro-2-[({[2-methoxy-5-(trifluoromethyl)phenyl]-imino}methylene)amino]phenyl}-2-propenoate (Example 18A), 341 mg (1.78 mmol) of 1-(3-methoxyphenyl)piperazine and a spatula tip of silica gel are stirred in 20 ml of dichloromethane at room temperature for one hour and then under reflux for 35 hours. The target compound is obtained after purification on silica gel (dichloromethane, dichloromethane/ethyl acetate 10:1).

Yield: 1012 mg (97% of theory)
HPLC (Method 6): $R_t$=4.8 min
MS (ESI-pos): m/z=587 (M+H)$^+$

Example 32A

Methyl {8-fluoro-2-[4-(3,4-difluorophenyl)-1-piperazinyl]-3-[2-methoxy-5-(trifluoromethyl)-phenyl]-3,4-dihydro-4-quinazolinyl}acetate

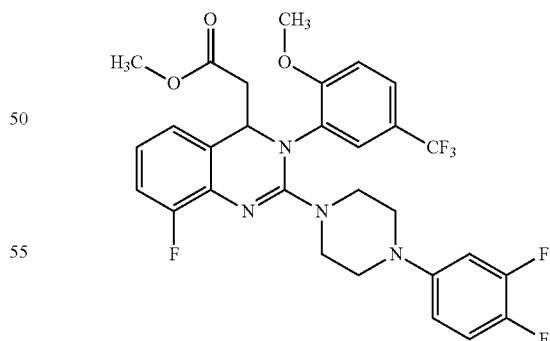

700 mg (1.78 mmol) of methyl (2E)-3-{3-fluoro-2-[({[2-methoxy-5-(trifluoromethyl)phenyl]-imino}methylene)amino]phenyl}-2-propenoate (Example 18A), 352 mg (1.78 mmol) of 1-(3,4-difluorophenyl)piperazine (Example 16A) and a spatula tip of silica gel are stirred in 20 ml of dichloromethane at room temperature for 1 hour and then under reflux for 20 hours. The target compound is then purified by chromatography on silica gel (dichloromethane, dichloromethane/ethyl acetate 10:1).
Yield: 1027 mg (97% of theory)
HPLC (Method 1): $R_t$=4.8 min
MS (ESI-pos): m/z=593 (M+H)$^+$ Example 33A Methyl {8-fluoro-2-[4-(3-methylphenyl)-1-piperazinyl]-3-[2-methoxy-5-(trifluoromethyl)phenyl]-3,4-dihydro-4-quinazolinyl}acetate

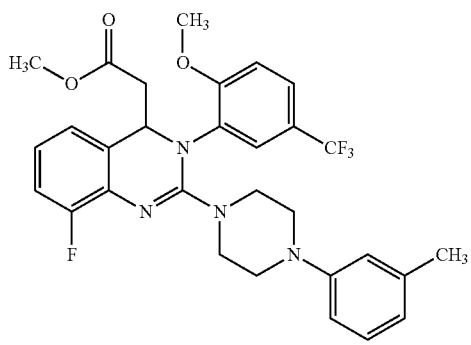

11.5 g (29.16 mmol) of methyl (2E)-3-{3-fluoro-2-[({[2-methoxy-5-(trifluoromethyl)phenyl]-imino}methylene)amino]phenyl}-2-propenoate (Example 18A), 5.14 g (29.16 mmol) of 1-(3-methylphenyl)piperazine and a spatula tip of silica gel are stirred in 300 ml of dichloromethane at room temperature for 1 hour and then under reflux for 20 hours. The product is obtained after chromatography on silica gel (dichloromethane, dichloromethane/ethyl acetate 10:1, 5:1).
Yield: 15.8 g (95% of theory)
HPLC (Method 1): $R_t$=4.8 min
MS (ESI-pos): m/z=571 (M+H)$^+$ Example 34A Methyl {8-fluoro-2-[4-(3-fluorophenyl)-1-piperazinyl]-3-[2-methoxy-5-(trifluoromethyl)phenyl]-3,4-dihydro-4-quinazolinyl}acetate

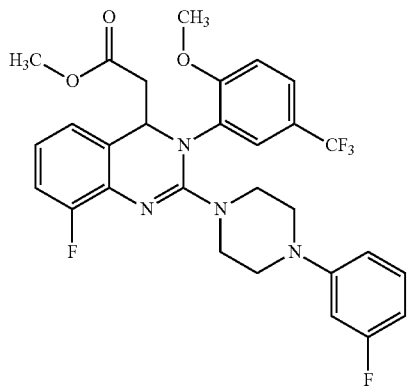 [SMILES: COC(=O)CC1c2cccc(F)c2N=C(N2CCN(c3cccc(F)c3)CC2)N1c1cc(C(F)(F)F)ccc1OC]

100 mg (0.25 mmol) of methyl (2E)-3-{3-fluoro-2-[({[2-methoxy-5-(trifluoromethyl)phenyl]-imino}methylene)amino]phenyl}-2-propenoate (Example 18A), 45.7 mg (0.25 mmol) of 1-(3-fluorophenyl)piperazine (Example 15A) and a spatula tip of silica gel are stirred in 15 ml of dichloromethane at room temperature for 1 hour and then under reflux for 20 hours. The target compound is obtained after chromatography on silica gel (dichloromethane, dichloromethane/ethyl acetate 10:1).
Yield: 139.2 mg (96% of theory)
HPLC (Method 1): =4.8 min
MS (ESI-pos): m/z=575 (M)$^+$ Example 35A Methyl {8-fluoro-2-[4-(3-chlorophenyl)-1-piperazinyl]-3-[3-(trifluoromethyl)phenyl]-3,4-dihydro-4-quinazolinyl}acetate

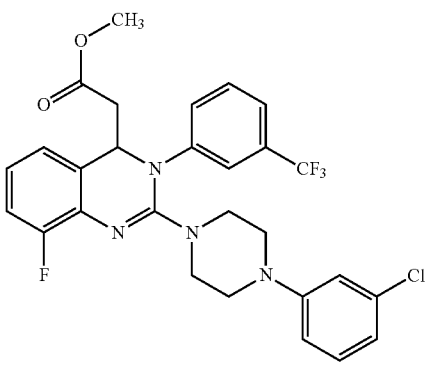 [SMILES: COC(=O)CC1c2cccc(F)c2N=C(N2CCN(c3cccc(Cl)c3)CC2)N1c1cccc(C(F)(F)F)c1]

Starting with 93 mg (0.2 mmol) of the iminophosphorane from Example 10A, the general procedure [G] gives 51 mg (45% of theory) of product. LC-MS (Method 3): $R_t$=4.78 min
MS (ESI-pos): m/z=561 (M+H)$^+$ Example 36A Methyl {8-fluoro-2-[4-(1,3-benzodioxol-5-yl)-1-piperazinyl]-3-[3-(trifluoromethyl)phenyl]-3,4-dihydro-4-quinazolinyl}acetate

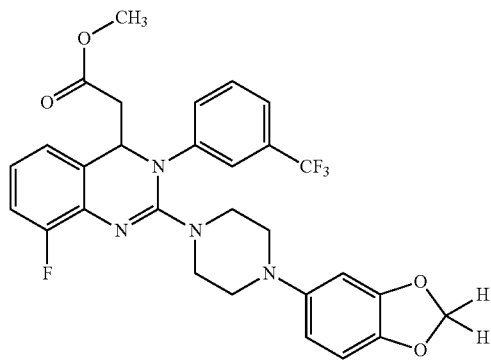 [SMILES: COC(=O)CC1c2cccc(F)c2N=C(N2CCN(c3ccc4c(c3)OCO4)CC2)N1c1cccc(C(F)(F)F)c1]

Starting with 4.19 g (9.2 mmol) of the iminophosphorane from Example 10A, the general procedure [G] gives 3.67 g (70% of theory) of product.
HPLC (Method 1): $R_t$=4.67 min
MS (ESI-pos): m/z=571 (M+H)$^+$

Example 37A

Methyl 4-amino-3-[(1E)-3-tert-butoxy-3-oxoprop-1-en-1-yl]benzoate

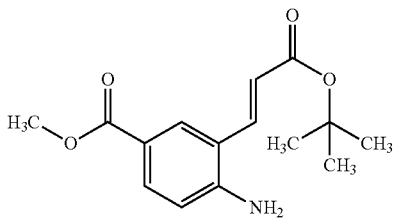 [SMILES: COC(=O)c1ccc(N)c(/C=C/C(=O)OC(C)(C)C)c1]

Starting with 25.0 g (90.2 mmol) of methyl 4-amino-3-iodobenzoate, the general procedure [A] gives 24.3 g (88% of theory) of product.

HPLC (Method 1): $R_t$=4.71 min
MS (DCI-pos): m/z=295 (M+NH$_4$)$^+$

Example 38A

Methyl (2E)-3-(4-cyano-2-nitrophenyl)-2-propenoate

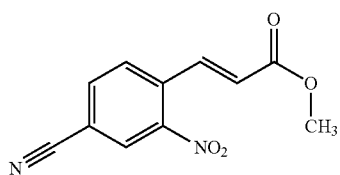

Starting with 3.00 g (17.0 mmol) of 4-cyano-2-nitrobenzaldehyde, the general procedure [B] and recrystallization from methanol gives 2.51 g (63% of theory) of product.

HPLC (Method 1): $R_t$=4.06 min
MS (ESI-pos): m/z=233 (M+H)$^+$

Example 39A

Methyl 3-[2-amino-7-cyanophenyl]propenoate

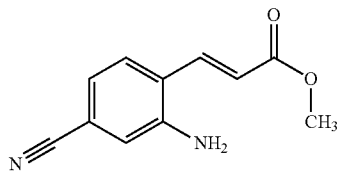 [SMILES: COC(=O)/C=C/c1ccc(C#N)cc1[N+](=O)[O-]]

Starting with 1.0 g (4.31 mmol) of the nitro compound from Example 38A, the general procedure [D] (but without boiling over activated carbon) gives 793 mg (89% of theory) of product.

HPLC (Method 1): $R_t$=3.99 min

Example 40A

Methyl (2E)-3-{6-cyano-2-[(triphenylphosphoranylidene)amino]phenyl}propenoate

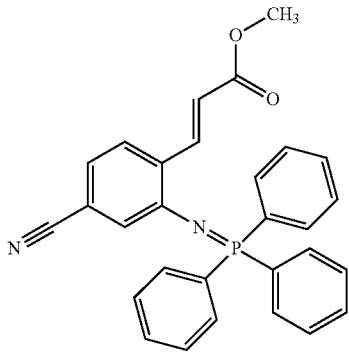 [SMILES: COC(=O)/C=C/c1ccc(C#N)cc1N=P(c1ccccc1)(c1ccccc1)c1ccccc1]

Starting with 0.75 g (3.71 mmol) of the amine compound from Example 39A, the general procedure [E] gives 1.09 g (62% of theory) of product.

HPLC (Method 1): =4.30 min
MS (ESI-pos): m/z=463 (M+H)$^+$

Example 41A

Methyl 3-[(1E)-3-tert-butoxy-3-oxoprop-1-en-1-yl]-4-[(triphenylphosphoranylidene)amino]-benzoate

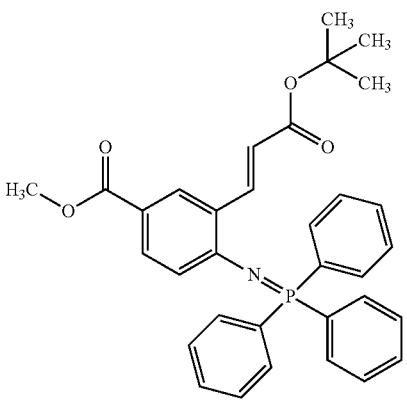 [SMILES: COC(=O)c1ccc(N=P(c2ccccc2)(c2ccccc2)c2ccccc2)c(/C=C/C(=O)OC(C)(C)C)c1]

Starting with 19.0 g (68.5 mmol) of the amine compound from Example 37A, the general procedure [E] gives 31.4 g (85% of theory) of product.

HPLC (Method 1): =4.69 min
MS (ESI-pos): m/z=538 (M+H)$^+$

Example 42A

Methyl {8-fluoro-2-[4-(4-fluorophenyl)-1-piperazinyl]-3-[2-methoxy-5-(trifluoromethyl)phenyl]-3,4-dihydro-4-quinazolinyl}acetate

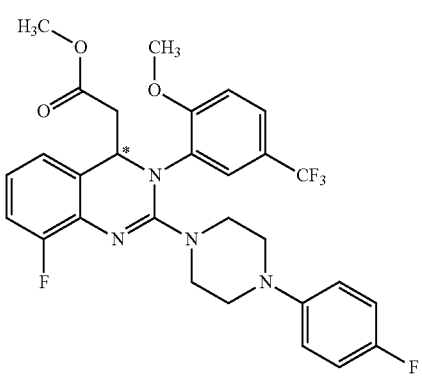

This compound is obtained as enantiomer A by separating the racemate from Example 30A chromatographically according to Method 15 in to the enantiomers. Starting with 231 g of racemate, 120 g of the target product, which is directly reacted further, are obtained.

MS (ESI-pos): m/z=575 (M+H)$^+$

Example 43A

Methyl {8-fluoro-2-[4-(3-methoxyphenyl)-1-piperazinyl]-3-[2-methoxy-5-(trifluoromethyl)-phenyl]-3,4-dihydro-4-quinazolinyl}acetate

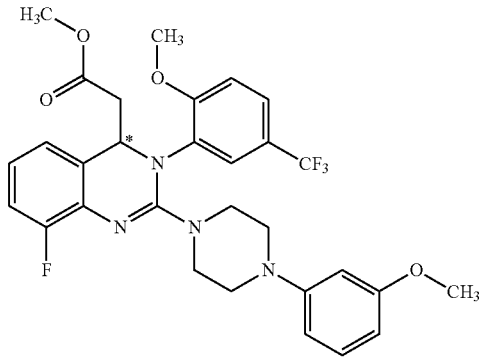 [SMILES: COC(=O)CC1c2cccc(F)c2N=C(N2CCN(c3cccc(OC)c3)CC2)N1c1cc(C(F)(F)F)ccc1OC]

The compound is obtained as enantiomer A by separating the racemate from Example 31A chromatographically according to Method 15 into the enantiomers. Starting with 231 g of racemate, 111 g (48% of theory) of the target product are obtained.

MS (ESI-pos): m/z=587 (M+H)$^+$

Example 44A

Methyl {6-cyano-2-[4-(4-fluorophenyl)-1-piperazinyl]-3-[3-(trifluoromethyl)phenyl]-3,4-dihydro-4-quinazolinyl}acetate

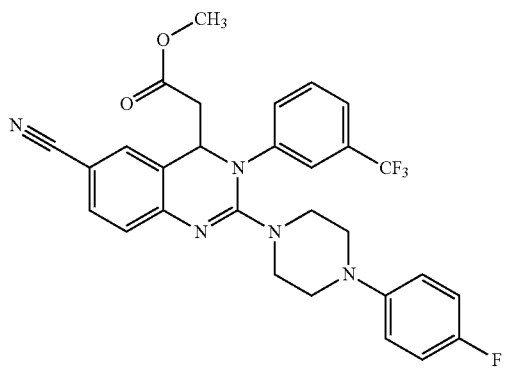 [SMILES: COC(=O)CC1c2cc(C#N)ccc2N=C(N2CCN(c3ccc(F)cc3)CC2)N1c1cccc(C(F)(F)F)c1]

Starting with 400 mg (0.6 mmol) of the iminophosphorane from Example 12A, the general procedure [G] gives 166 mg (48% of theory) of product.

HPLC (Method 1): R$_t$=4.65 min
MS (ESI-pos): m/z=552 (M+H)$^+$

Example 45A

Methyl {7-cyano-2-[4-(4-fluorophenyl)-1-piperazinyl]-3-[3-(trifluoromethyl)phenyl]-3,4-dihydro-4-quinazolinyl}acetate Starting with 1.0 g (2.16 mmol) of the iminophosphorane from Example 40A, the general procedure [G] gives 1.07 g (98% of theory) of product.

HPLC (Method 1): R$_t$=4.72 min
MS (ESI-pos): m/z=552 (M+H)$^+$

Example 46A

Methyl 4-(2-tert-butoxy-2-oxoethyl)-2-[4-(4-fluorophenyl)piperazin-1-yl]-3-[3-(trifluoromethyl)-phenyl]-3,4-dihydroquinazoline-6-carboxylate

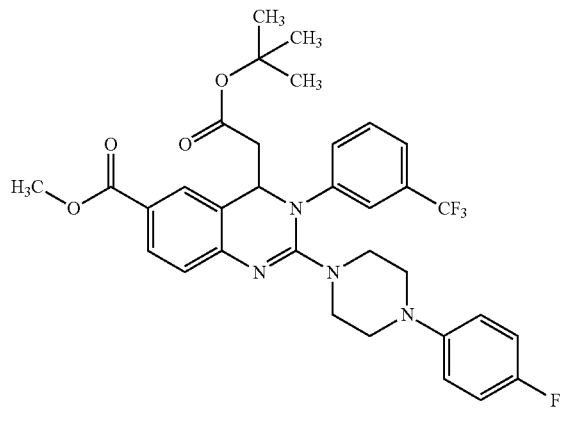 [SMILES: COC(=O)c1ccc2c(c1)C(CC(=O)OC(C)(C)C)N(c1cccc(C(F)(F)F)c1)C(N1CCN(c3ccc(F)cc3)CC1)=N2]

Starting with 4.2 g (9.3 mmol) of the iminophosphorane from Example 41A, the general procedure [G] gives 3.9 g (51% of theory) of product. HPLC (Method 1): $R_t$=5.03 min MS (ESI-pos): m/z=627 (M+H)$^+$

Example 47A

Methyl {8-fluoro-2-[4-(4-fluorophenyl)-1-piperazinyl]-3-[3-(trifluoromethyl)phenyl]-3,4-dihydro-4-quinazolinyl}acetate

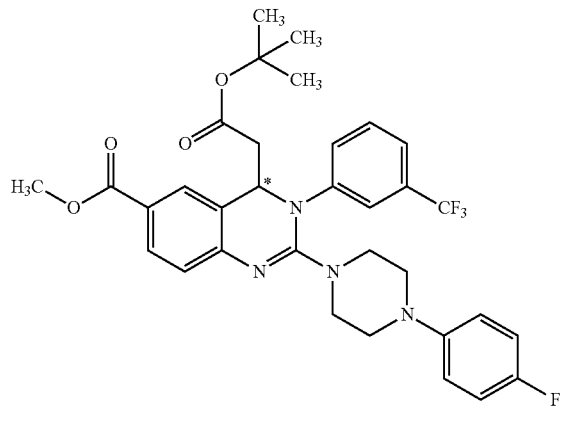 [SMILES: COC(=O)c1ccc2c(c1)C(CC(=O)OC(C)(C)C)N(c1cccc(C(F)(F)F)c1)C(N1CCN(c3ccc(F)cc3)CC1)=N2]

This compound is obtained as enantiomer A following the separation of enantiomers of 3.5 g of Example 46A (1.4 mg, 20% of theory).

HPLC (Method 1): $R_t$=4.91 min

MS (ESI-pos): m/z=627 (M-41)$^+$

Example 48A 4-(2-tert-Butoxy-2-oxoethyl)-2-[4-(4-fluorophenyl)piperazin-1-yl]-3-[3-(trifluoromethyl)phenyl]-3,4-dihydroquinazoline-6-carboxylic acid

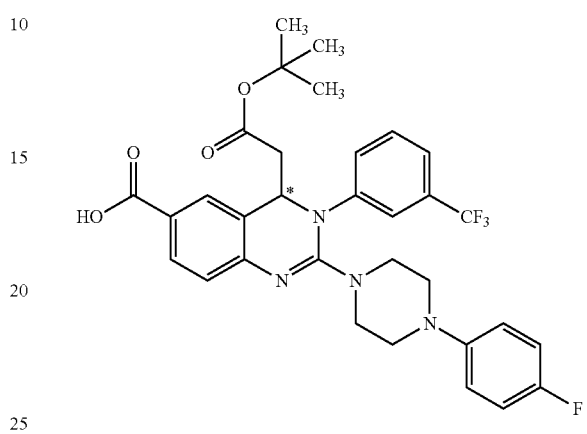

1.3 g (2.0 mmol) of the methyl carboxylate from Example 47A are dissolved in 12 ml of dioxane, 2.4 ml of an aqueous 1N solution of potassium hydroxide are added and the mixture is stirred at 60° C. for 5 hours. The pH is adjusted to pH=4 using an aqueous 1N solution of hydrochloric acid and the reaction mixture is concentrated and purified by preparative HPLC. This gives 580 mg (48% of theory) of the product.

HPLC (Method 1): $R_t$=4.85 min

MS (ESI-pos): m/z=613 (M+H)$^+$

Example 49A

Tert-butyl {6-(aminocarbonyl)-2-[4-(4-fluorophenyl)piperazin-1-yl]-3-[3-(trifluoromethyl)phenyl]-3,4-dihydroquinazolin-4-yl}acetate

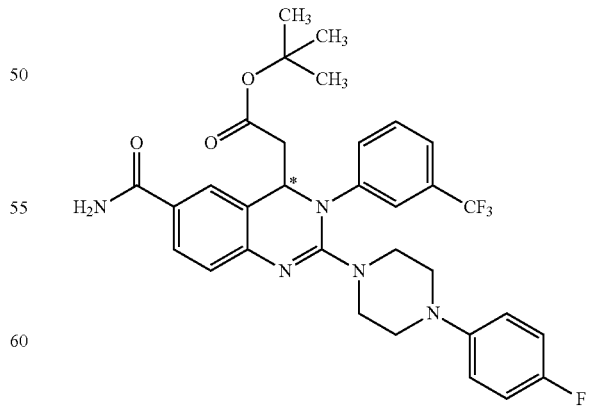

560 mg (0.9 mmol) of the carboxylic acid from Example 48A, 2.6 mmol of aluminium chloride, 1.1 mmol of 1-hydroxy-1H-benzotriazole hydrate and 1.1 mmol of N-(3-dim ethylaminopropyl)-N'-ethylcarbodiimide are suspended in DMF. 2.6 mmol of N,N-diisopropylamine are added, and the mixture is stirred at room temperature for 16 hours. 20 ml of ethyl acetate are added to the reaction mixture, which is then washed with a saturated aqueous sodium bicarbonate solution and a saturated aqueous sodium chloride solution. The combined aqueous phases are adjusted to pH=8 and extracted with ethyl acetate. The combined organic phases are finally washed with a saturated aqueous sodium chloride solution, dried over sodium sulphate and concentrated. This gives 548 mg (97% of theory) of product.

HPLC (Method 1): $R_t$=4.73 min

MS (ESI-pos): m/z=612 (M+H)$^+$

Examples 50A to 112A of Table 1 can be prepared from the corresponding starting materials using the general procedures [A] to [G].

TABLE 1

| Example No. | Structure | $R_t$ [min] | HPLC method | MS ESIpos. [M + H]$^+$ |
|---|---|---|---|---|
| 50A | 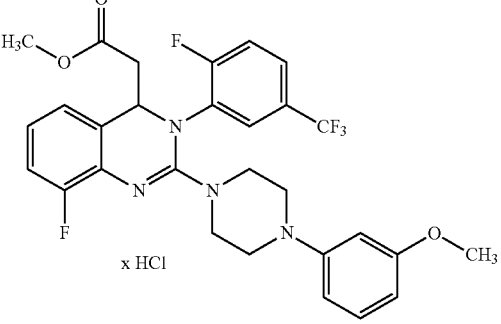 x HCl | 4.53 | 1 | 561 [M + H − HCl]$^+$ |
| 51A | 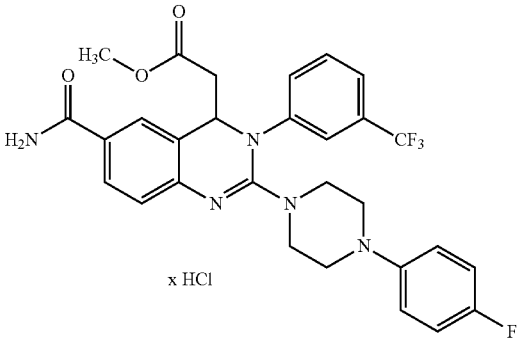 x HCl | 4.22 | 1 | 556 [M + H − HCl]$^+$ |
| 52A | 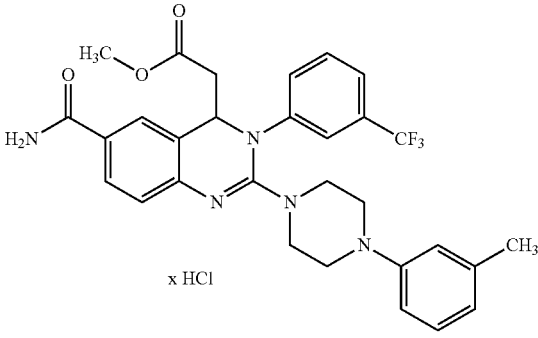 x HCl | 4.36 | 1 | 552 [M + H − HCl]$^+$ |
| 53A | 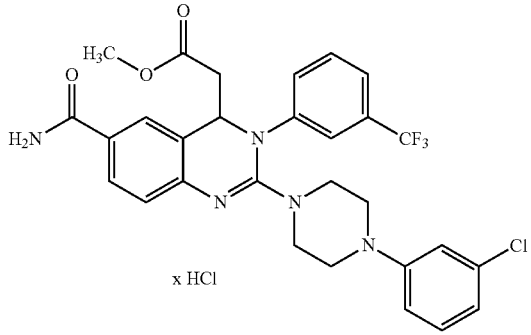 x HCl | 4.37 | 1 | 572 [M + H − HCl]$^+$ |

TABLE 1-continued

| Example No. | Structure | R$_t$ [min] | HPLC method | MS ESIpos. [M + H]$^+$ |
|---|---|---|---|---|
| 54A | x HCl | 4.54 | 1 | 549 [M + H − HCl]$^+$ |
| 55A | x HCl | 4.27 | 1 | 568 [M + H − HCl]$^+$ |
| 56A | 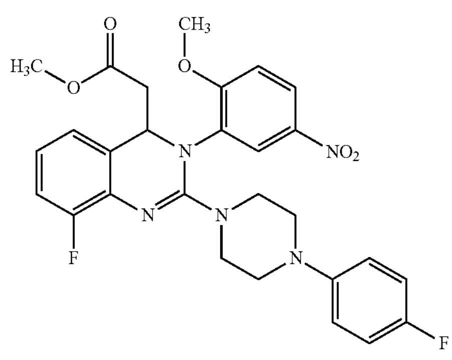 | 4.30 | 1 | 538 |
| 57A | 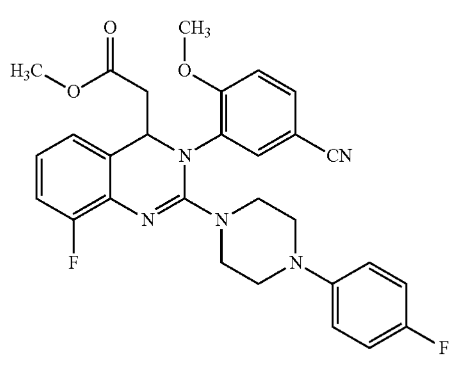 [SMILES: COC(=O)CC1c2cccc(F)c2N=C(N2CCN(c3ccc(F)cc3)CC2)N1c1cc([N+](=O)[O-])ccc1OC] | 4.28 | 1 | 518 |

TABLE 1-continued
| Example No. | Structure | $R_t$ [min] | HPLC method | MS ESIpos. $[M + H]^+$ |
|---|---|---|---|---|
| 58A | 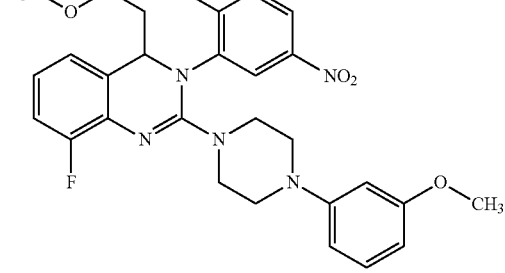 | 4.41 | 1 | 538 |
| 59A | 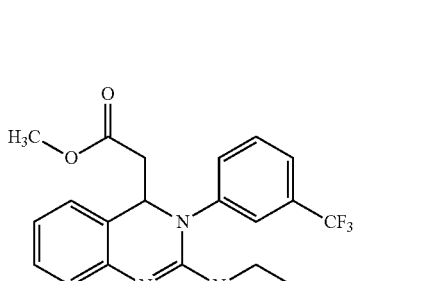 | 4.82 | 1 | 557 |
| 60A | 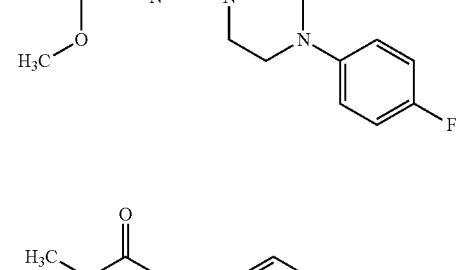 | 4.61 | 1 | 549 $[M + H - HCl]^+$ |
| 61A | 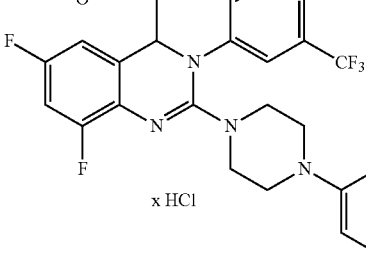 | 4.89 | 1 | 517 |

TABLE 1-continued

| Example No. | Structure | $R_t$ [min] | HPLC method | MS ESIpos. $[M + H]^+$ |
|---|---|---|---|---|
| 62A | 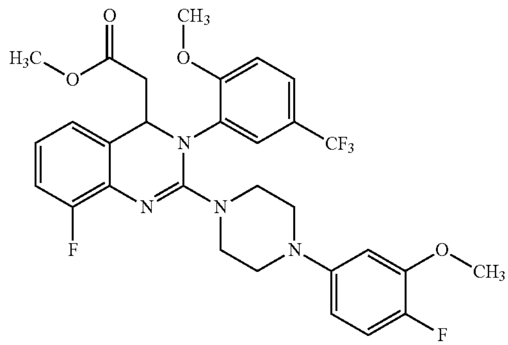 [SMILES: COC(=O)CC1c2cccc(F)c2N=C(N2CCN(c3ccc(F)c(OC)c3)CC2)N1c1cc(C(F)(F)F)ccc1OC] | 4.81 | 6 | 605 |
| 63A | 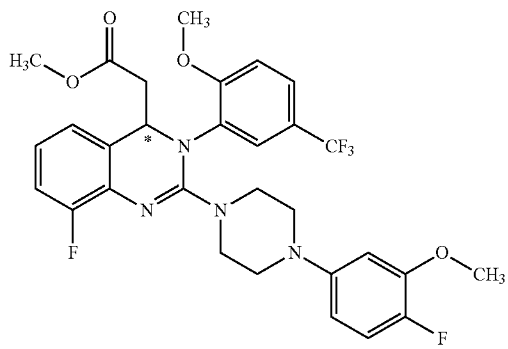 [SMILES: COC(=O)CC1c2cccc(F)c2N=C(N2CCN(c3ccc(F)c(OC)c3)CC2)N1c1cc(C(F)(F)F)ccc1OC] | 4.60 | 6 | 591 |
| 64A | 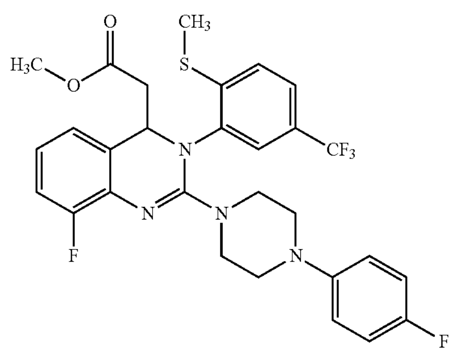 [SMILES: COC(=O)CC1c2cccc(F)c2N=C(N2CCN(c3ccc(F)cc3)CC2)N1c1cc(C(F)(F)F)ccc1SC] | 4.85 | 6 | 591 |
| 65A | 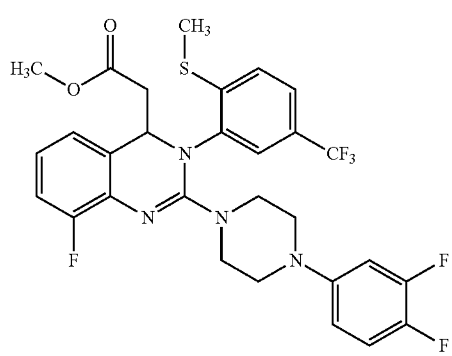 [SMILES: COC(=O)CC1c2cccc(F)c2N=C(N2CCN(c3ccc(F)c(F)c3)CC2)N1c1cc(C(F)(F)F)ccc1SC] | 4.92 | 6 | 609 |

TABLE 1-continued

| Example No. | Structure | R$_t$ [min] | HPLC method | MS ESIpos. [M + H]$^+$ |
|---|---|---|---|---|
| 66A | 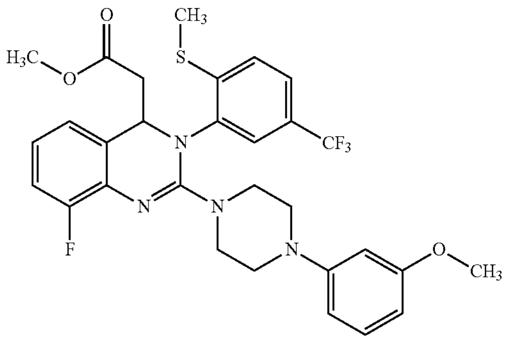 [SMILES: COC(=O)CC1c2cccc(F)c2N=C(N2CCN(c3cccc(OC)c3)CC2)N1c1cc(C(F)(F)F)ccc1SC] | 4.83 | 1 | 603 |
| 67A | 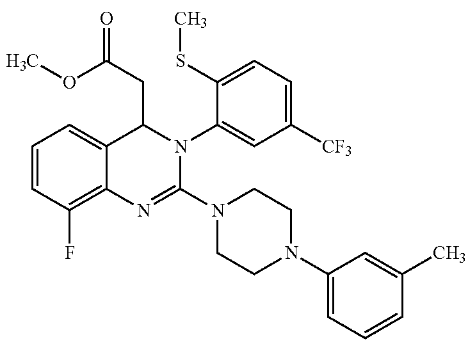 [SMILES: COC(=O)CC1c2cccc(F)c2N=C(N2CCN(c3cccc(C)c3)CC2)N1c1cc(C(F)(F)F)ccc1SC] | 4.78 | 1 | 587 |
| 68A | 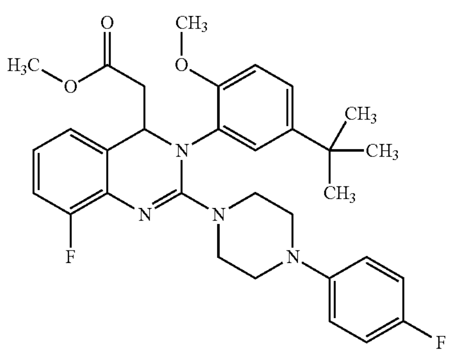 [SMILES: COC(=O)CC1c2cccc(F)c2N=C(N2CCN(c3ccc(F)cc3)CC2)N1c1cc(C(C)(C)C)ccc1OC] | 5.13 | 1 | 563 |
| 69A | 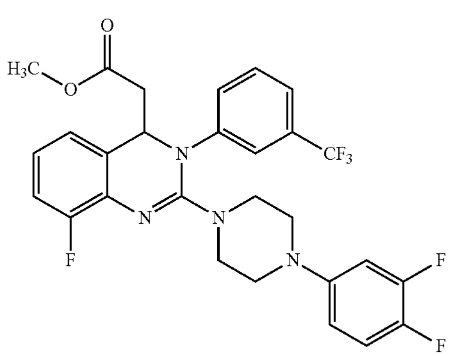 [SMILES: COC(=O)CC1c2cccc(F)c2N=C(N2CCN(c3ccc(F)c(F)c3)CC2)N1c1cccc(C(F)(F)F)c1] | 4.76 | 1 | 563 |

TABLE 1-continued

| Example No. | Structure | $R_t$ [min] | HPLC method | MS ESIpos. $[M + H]^+$ |
|---|---|---|---|---|
| 70A | 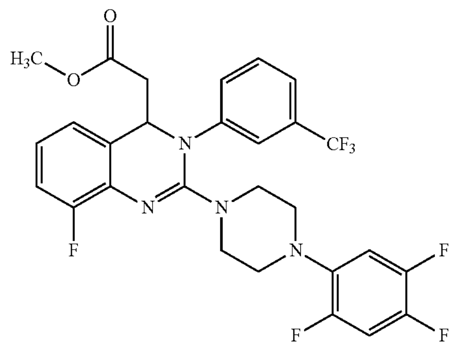 [SMILES: COC(=O)CC1c2cccc(F)c2N=C(N2CCN(c3cc(F)c(F)cc3F)CC2)N1c1cccc(C(F)(F)F)c1] | 4.81 | 1 | 581 |
| 71A | 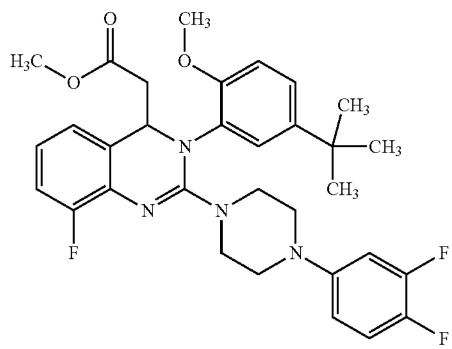 [SMILES: COC(=O)CC1c2cccc(F)c2N=C(N2CCN(c3ccc(F)c(F)c3)CC2)N1c1cc(C(C)(C)C)ccc1OC] | 5.21 | 1 | 581 |
| 72A | 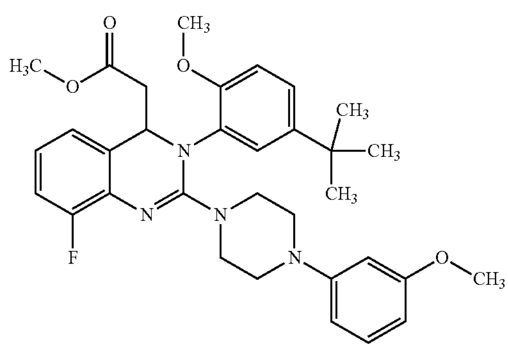 [SMILES: COC(=O)CC1c2cccc(F)c2N=C(N2CCN(c3cccc(OC)c3)CC2)N1c1cc(C(C)(C)C)ccc1OC] | 5.12 | 1 | 575 |
| 73A | 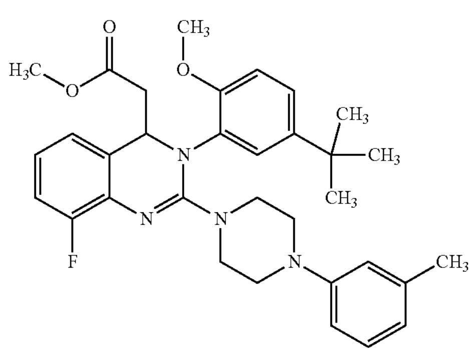 [SMILES: COC(=O)CC1c2cccc(F)c2N=C(N2CCN(c3cccc(C)c3)CC2)N1c1cc(C(C)(C)C)ccc1OC] | 4.98 | 1 | 559 |

TABLE 1-continued
| Example No. | Structure | R$_t$ [min] | HPLC method | MS ESIpos. [M + H]$^+$ |
|---|---|---|---|---|
| 74A | 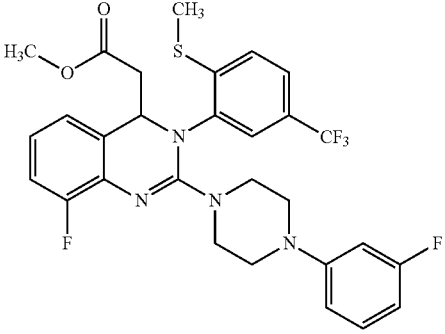 [SMILES: COC(=O)CC1c2cccc(F)c2N=C(N2CCN(c3cccc(F)c3)CC2)N1c1cc(C(F)(F)F)ccc1SC] | 4.86 | 1 | 591 |
| 75A | 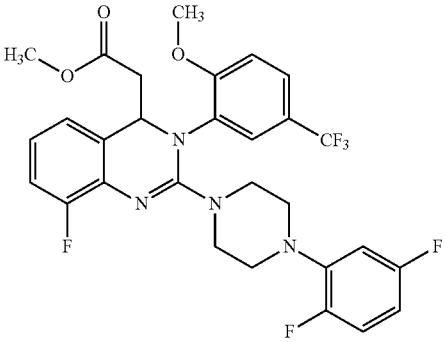 [SMILES: COC(=O)CC1c2cccc(F)c2N=C(N2CCN(c3cc(F)ccc3F)CC2)N1c1cc(C(F)(F)F)ccc1OC] | 4.86 | 6 | 593 |
| 76A | 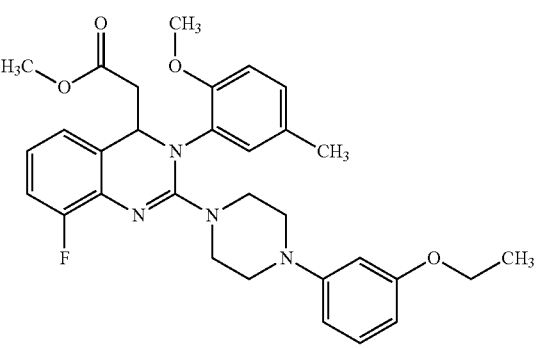 [SMILES: CCOc1cccc(N2CCN(C3=Nc4c(F)cccc4C(CC(=O)OC)N3c3cc(C)ccc3OC)CC2)c1] | 4.94 | 1 | 547 |
| 77A | 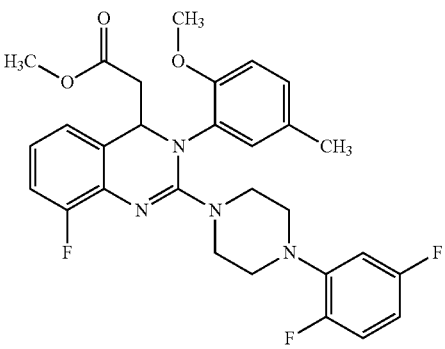 | 4.82 | 1 | 539 |

TABLE 1-continued
| Example No. | Structure | $R_t$ [min] | HPLC method | MS ESIpos. $[M + H]^+$ |
|---|---|---|---|---|
| 78A | 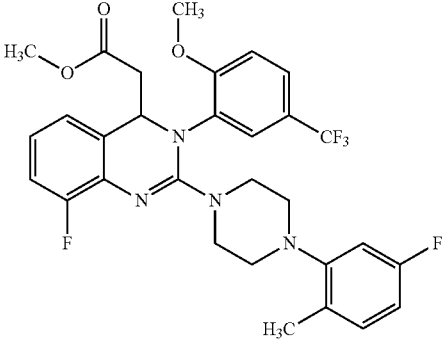 [SMILES: COC(=O)CC1c2cccc(F)c2N=C(N2CCN(c3cc(F)ccc3C)CC2)N1c1cc(C(F)(F)F)ccc1OC] | 4.92 | 1 | 589 |
| 79A | 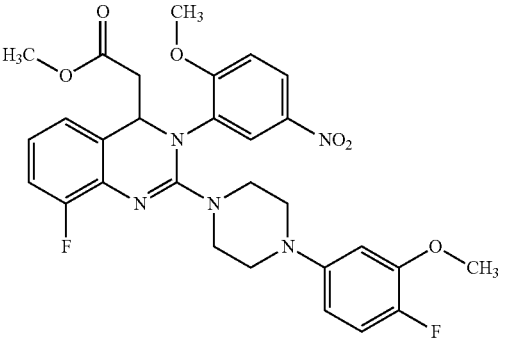 [SMILES: COC(=O)CC1c2cccc(F)c2N=C(N2CCN(c3ccc(F)c(OC)c3)CC2)N1c1cc([N+](=O)[O-])ccc1OC] | 4.57 | 1 | 582 |
| 80A | 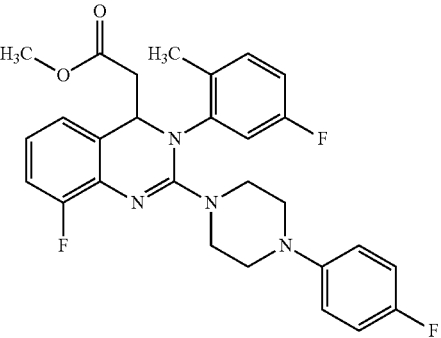 [SMILES: COC(=O)CC1c2cccc(F)c2N=C(N2CCN(c3ccc(F)cc3)CC2)N1c1cc(F)ccc1C] | 2.38 | 3 | 495 |
| 81A | 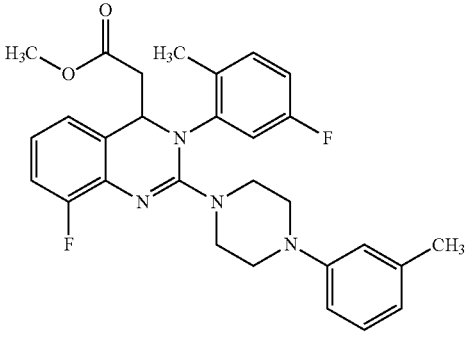 | 1.95 | 9 | 491 |

TABLE 1-continued

| Example No. | Structure | $R_t$ [min] | HPLC method | MS ESIpos. $[M + H]^+$ |
|---|---|---|---|---|
| 82A | 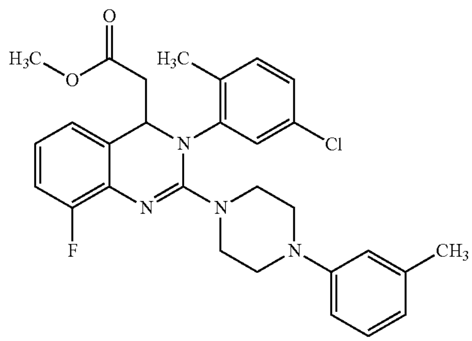 [SMILES: COC(=O)CC1c2cccc(F)c2N=C(N2CCN(c3cccc(C)c3)CC2)N1c1cc(F)ccc1C] | 1.97 | 9 | 507 |
| 83A | 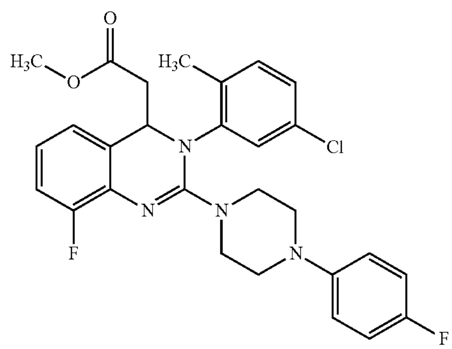 | 1.93 | 9 | 511 |
| 84A | 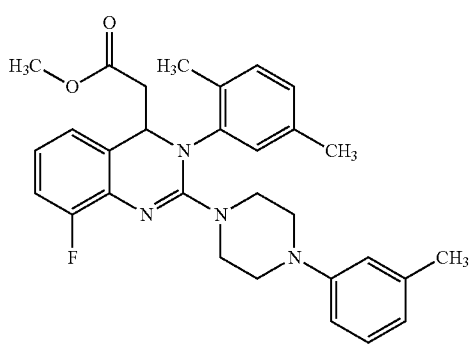 [SMILES: COC(=O)CC1c2cccc(F)c2N=C(N2CCN(c3cccc(C)c3)CC2)N1c1cc(Cl)ccc1C] | 1.90 | 9 | 487 |
| 85A | 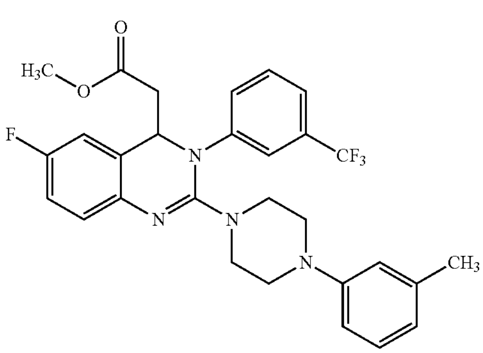 [SMILES: COC(=O)CC1c2cc(F)ccc2N=C(N2CCN(c3cccc(C)c3)CC2)N1c1cccc(C(F)(F)F)c1] | 4.87 | 1 | 541 |

TABLE 1-continued

| Example No. | Structure | $R_t$ [min] | HPLC method | MS ESIpos. $[M + H]^+$ |
|---|---|---|---|---|
| 86A | 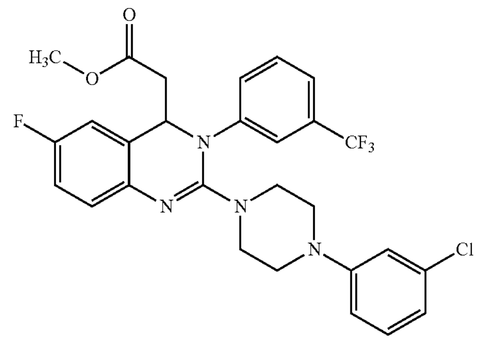 [SMILES: COC(=O)CC1c2cc(F)ccc2N=C(N2CCN(c3cccc(Cl)c3)CC2)N1c1cccc(C(F)(F)F)c1] | 4.91 | 1 | 561 |
| 87A | 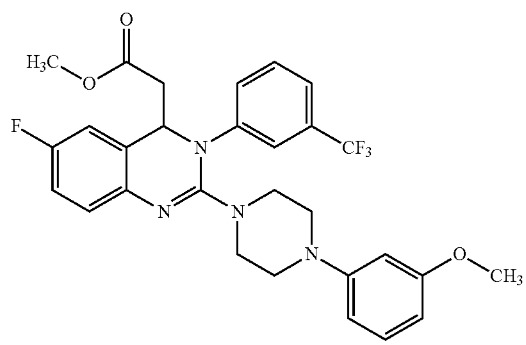 [SMILES: COC(=O)CC1c2cc(F)ccc2N=C(N2CCN(c3cccc(OC)c3)CC2)N1c1cccc(C(F)(F)F)c1] | 4.76 | 1 | 557 |
| 88A | 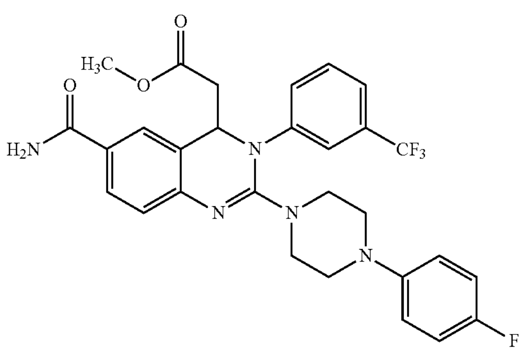 [SMILES: COC(=O)CC1c2cc(C(N)=O)ccc2N=C(N2CCN(c3ccc(F)cc3)CC2)N1c1cccc(C(F)(F)F)c1] | 4.65 | 1 | 552 |
| 89A | 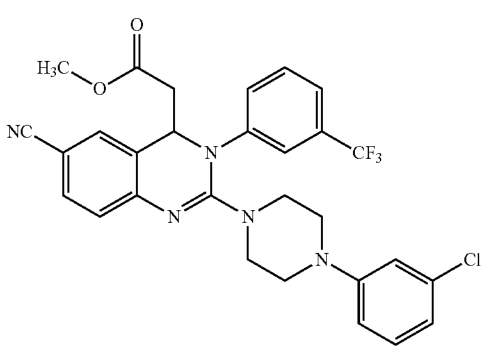 [SMILES: COC(=O)CC1c2cc(C#N)ccc2N=C(N2CCN(c3cccc(Cl)c3)CC2)N1c1cccc(C(F)(F)F)c1] | 4.77 | 1 | 568 |

TABLE 1-continued

| Example No. | Structure | $R_t$ [min] | HPLC method | MS ESIpos. $[M + H]^+$ |
|---|---|---|---|---|
| 90A | 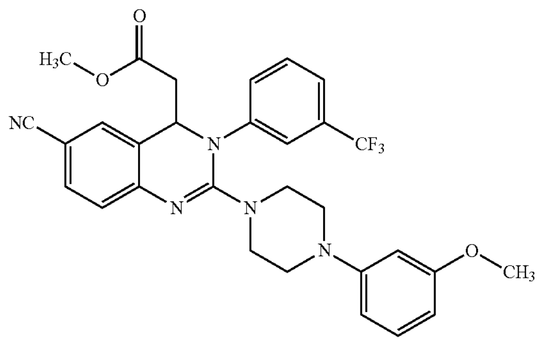 [SMILES: COC(=O)CC1c2cc(C#N)ccc2N=C(N2CCN(c3cccc(OC)c3)CC2)N1c1cccc(C(F)(F)F)c1] | 4.62 | 1 | 564 |
| 91A | 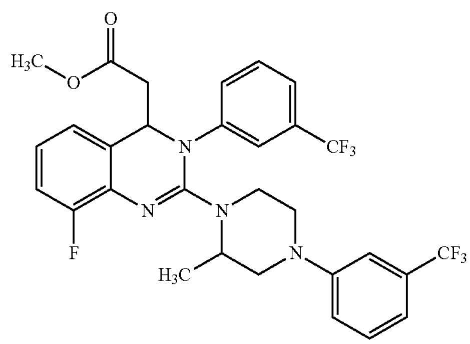 [SMILES: COC(=O)CC1c2cccc(F)c2N=C(N2CCN(c3cccc(C(F)(F)F)c3)CC2C)N1c1cccc(C(F)(F)F)c1] | 5.00 | 1 | 609 |
| 92A | 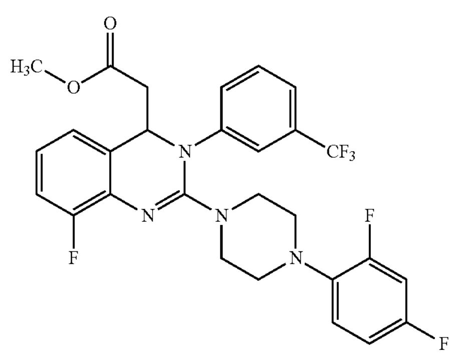 [SMILES: COC(=O)CC1c2cccc(F)c2N=C(N2CCN(c3ccc(F)cc3F)CC2)N1c1cccc(C(F)(F)F)c1] | 4.70 | 1 | 563 |
| 93A | 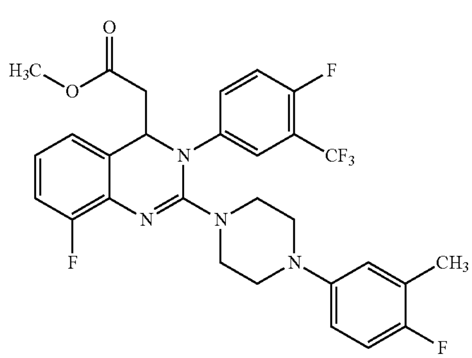 [SMILES: COC(=O)CC1c2cccc(F)c2N=C(N2CCN(c3ccc(F)c(C)c3)CC2)N1c1ccc(F)c(C(F)(F)F)c1] | | | 577 |

TABLE 1-continued

| Example No. | Structure | R$_t$ [min] | HPLC method | MS ESIpos. [M + H]$^+$ |
|---|---|---|---|---|
| 94A | 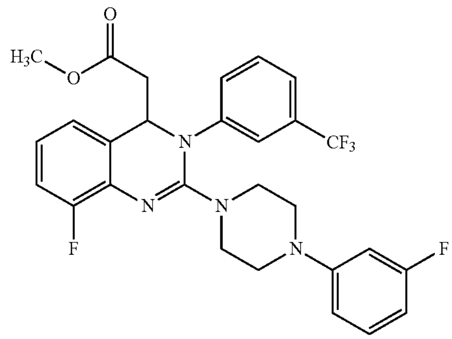 [SMILES: COC(=O)CC1c2cccc(F)c2N=C(N2CCN(c3cccc(F)c3)CC2)N1c1cccc(C(F)(F)F)c1] | 4.74 | 1 | 545 |
| 95A | 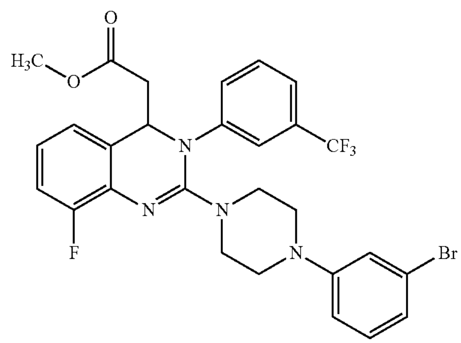 [SMILES: COC(=O)CC1c2cccc(F)c2N=C(N2CCN(c3cccc(Br)c3)CC2)N1c1cccc(C(F)(F)F)c1] | 4.90 | 1 | 605 |
| 96A | 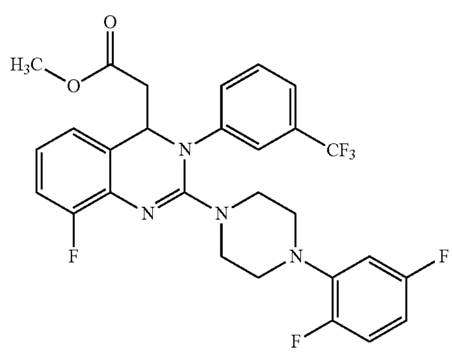 [SMILES: COC(=O)CC1c2cccc(F)c2N=C(N2CCN(c3cc(F)ccc3F)CC2)N1c1cccc(C(F)(F)F)c1] | 4.83 | 1 | 563 |
| 97A | 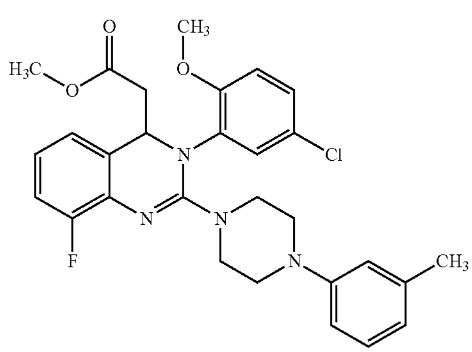 [SMILES: COC(=O)CC1c2cccc(F)c2N=C(N2CCN(c3cccc(C)c3)CC2)N1c1cc(Cl)ccc1OC] | 4.82 | 1 | 537 |

TABLE 1-continued

| Example No. | Structure | R$_t$ [min] | HPLC method | MS ESIpos. [M + H]$^+$ |
|---|---|---|---|---|
| 98A | 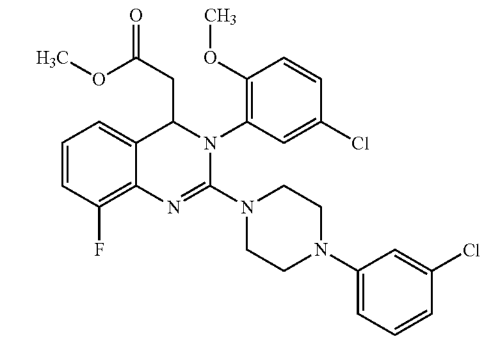 [SMILES: COC(=O)CC1c2cccc(F)c2N=C(N2CCN(c3cccc(Cl)c3)CC2)N1c1cc(Cl)ccc1OC] | 4.90 | 1 | 557 |
| 99A | 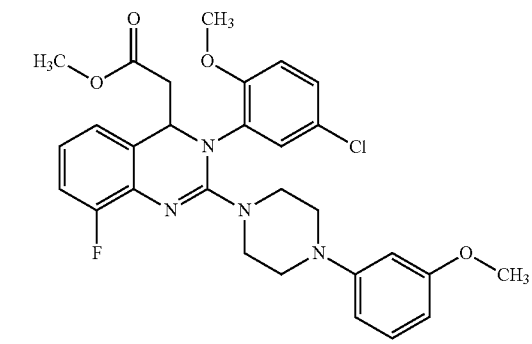 [SMILES: COC(=O)CC1c2cccc(F)c2N=C(N2CCN(c3cccc(OC)c3)CC2)N1c1cc(Cl)ccc1OC] | 4.81 | 1 | 553 |
| 100A | 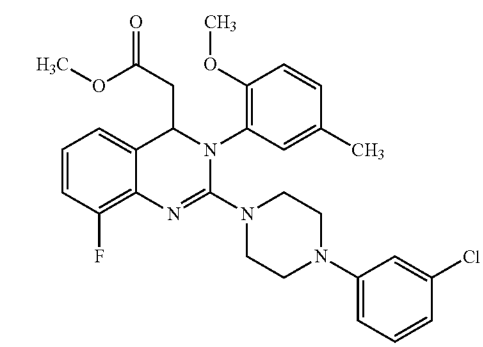 [SMILES: COC(=O)CC1c2cccc(F)c2N=C(N2CCN(c3cccc(Cl)c3)CC2)N1c1cc(C)ccc1OC] | 4.78 | 1 | — |
| 101A | 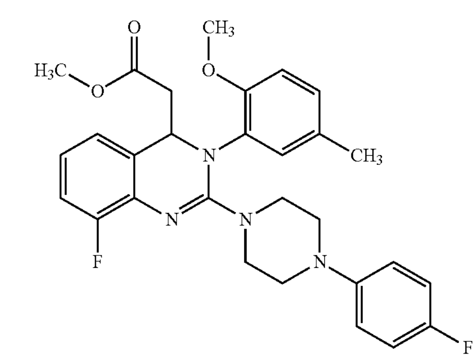 [SMILES: COC(=O)CC1c2cccc(F)c2N=C(N2CCN(c3ccc(F)cc3)CC2)N1c1cc(C)ccc1OC] | 4.78 | 1 | 521 |

TABLE 1-continued
| Example No. | Structure | $R_t$ [min] | HPLC method | MS ESIpos. $[M + H]^+$ |
|---|---|---|---|---|
| 102A | 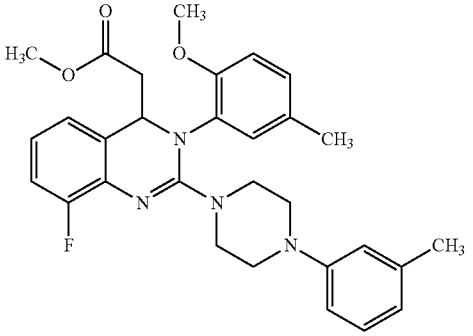 | 4.73 | 1 | 517 |
| 103A | 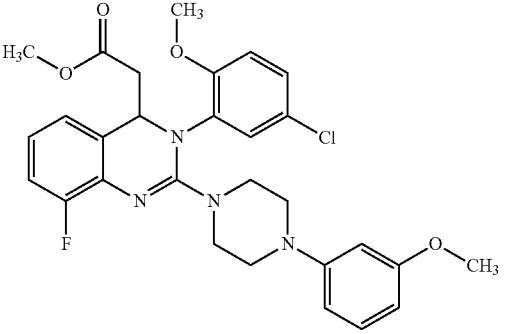 [SMILES: COC(=O)CC1c2cccc(F)c2N=C(N2CCN(c3cccc(OC)c3)CC2)N1c1cc(Cl)ccc1OC] | 3.10 | 16 | 533 |
| 104A | 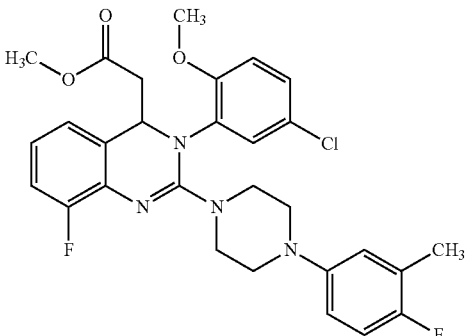 | 2.75 | 17 | 555 |
| 105A | 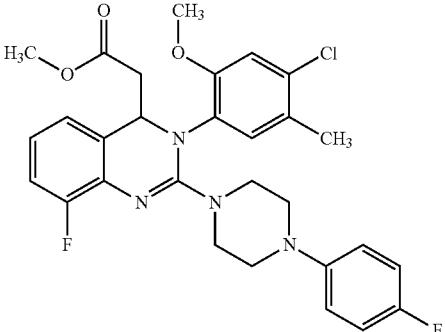 | 2.95 | 17 | 555 |

TABLE 1-continued

| Example No. | Structure | R_t [min] | HPLC method | MS ESIpos. [M + H]+ |
|---|---|---|---|---|
| 106A | 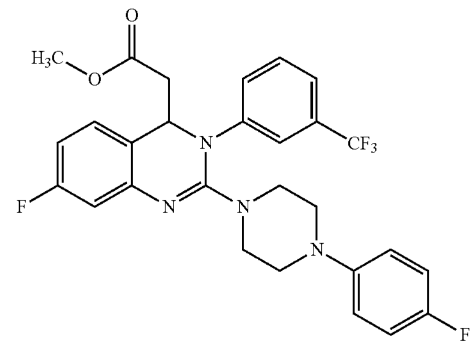 [SMILES: COC(=O)CC1c2ccc(F)cc2N=C(N2CCN(c3ccc(F)cc3)CC2)N1c1cccc(C(F)(F)F)c1] | 4.74 | 1 | 545 |
| 107A | 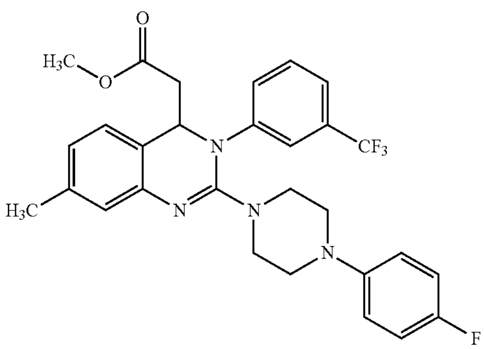 [SMILES: COC(=O)CC1c2ccc(C)cc2N=C(N2CCN(c3ccc(F)cc3)CC2)N1c1cccc(C(F)(F)F)c1] | 4.93 | 1 | 541 |
| 108A | 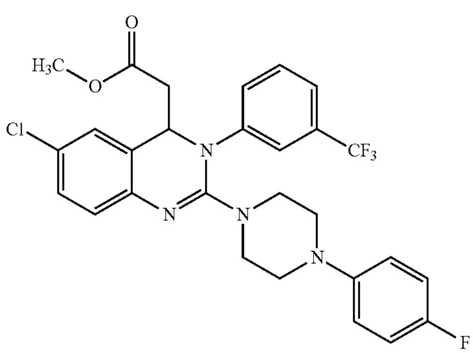 [SMILES: COC(=O)CC1c2cc(Cl)ccc2N=C(N2CCN(c3ccc(F)cc3)CC2)N1c1cccc(C(F)(F)F)c1] | 5.08 | 1 | 575 |
| 109A | 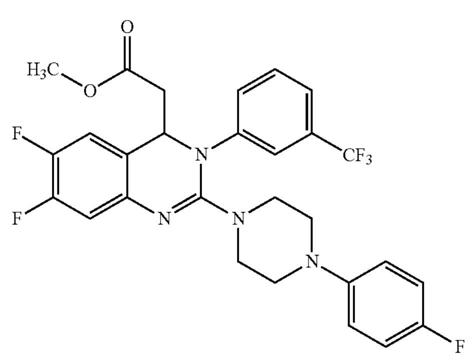 [SMILES: COC(=O)CC1c2cc(F)c(F)cc2N=C(N2CCN(c3ccc(F)cc3)CC2)N1c1cccc(C(F)(F)F)c1] | 4.88 | 1 | 563 |

TABLE 1-continued

| Example No. | Structure | R$_t$ [min] | HPLC method | MS ESIpos. [M + H]$^+$ |
|---|---|---|---|---|
| 110A | 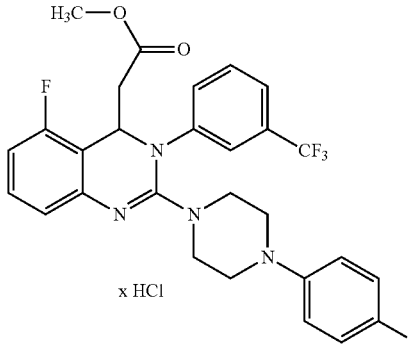 x HCl | 4.54 | 1 | 531 [M + H − HCl]$^+$ |
| 111A | 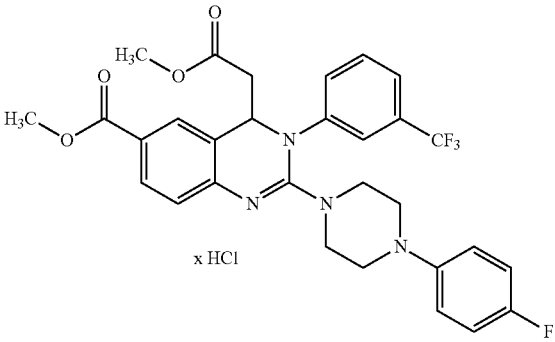 x HCl | 4.54 | 1 | 571 [M + H − HCl]$^+$ |

WORKING EXAMPLES

General procedure [H]: Hydrolysis of the Quinazolylacetic Acid Esters 1.0 equivalent of the quinazolyl ester are dissolved in dioxane, and 5.0 equivalents of 1N aqueous sodium hydroxide solution are added. The mixture is stirred at 80° C. for 16 hours, and after the reaction has ended (the reaction is monitored by analytical HPLC) the mixture is concentrated. The residue is then taken up in water and adjusted to pH 5 using 1N hydrochloric acid. The resulting precipitate is filtered off, washed with a little water and diethyl ether and dried at room temperature under high vacuum. Alternatively, the precipitate can be filtered off through an Extrelute cartridge, then washed with ethyl acetate, followed by concentration of the filtrate. If the purity of the product is not high enough, the product is purified either by preparative HPLC on an RP phase (Method 2 or Method 5) or on silica gel using mixtures of cyclohexane/ethyl acetate.

Example 1

{8-Fluoro-2-[4-(4-fluorophenyl)-1-piperazinyl]-3-[3-(trifluoromethyl)phenyl]-3,4-dihydro-4-quinazolinyl}acetic acid

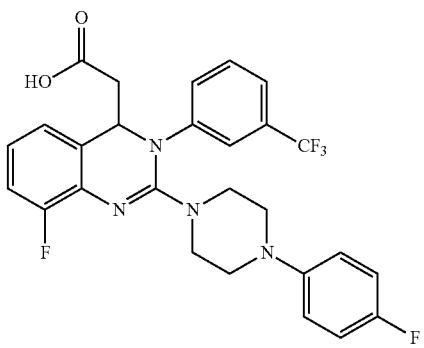 [SMILES: O=C(O)CC1c2cccc(F)c2N=C(N2CCN(c3ccc(F)cc3)CC2)N1c1cccc(C(F)(F)F)c1]

Starting with 37 mg (0.07 mmol) of the methyl ester from Example 19A, the general procedure [H] gives 29 mg (80% of theory) of product.

HPLC (Method 1): $R_t$=4.49 min

MS (ESI-pos): m/z=530.7 (M+H)$^+$ $^1$H NMR (400 MHz, CD$_3$CN): δ [ppm]=7.59 (s, 1H); 7.45 (t, 1H); 7.37 (t, 2H); 7.02-6.95 (m, 3H); 6.93-6.85 (m, 4H); 5.24 (dd, 1H); 2.98 (d$_b$, 4H); 2.91 (d$_b$, 4H); 2.73 (dd, 1H); 2.54 (dd, 1H).

Example 2

{8-Fluoro-2-[4-(4-fluorophenyl)-1-piperazinyl]-3-[3-(trifluoromethyl)phenyl]-3,4-dihydro-4-quinazolinyl}acetic acid

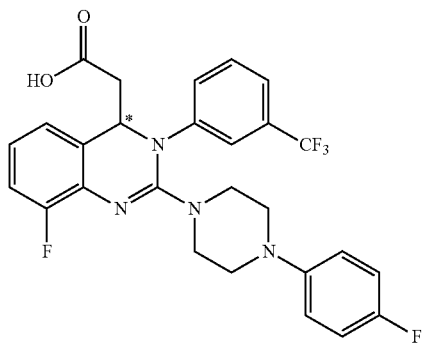 [SMILES: O=C(O)CC1c2cccc(F)c2N=C(N2CCN(c3ccc(F)cc3)CC2)N1c1cccc(C(F)(F)F)c1]

Starting with 695 mg (1.27 mmol) of the methyl ester from Example 20A, the general procedure [H] gives 488 mg (64% of theory) of product.

HPLC (Method 1): $R_t$=4.59 min

MS (ESI-pos): m/z=530.8 (M+H)$^+$ $^1$H NMR (400 MHz, CD$_3$CN): δ [ppm]=7.60 (s, 1H); 7.47-7.40 (m, 3H); 7.03-6.86 (m, 7H); 5.26-5.23 (m, 1H); 3.60-3.52 (m, 4H); 2.99-2.90 (m, 4H); 2.75 (dd, 1H); 2.56 (dd, 1H).

Example 3

{8-Fluoro-2-[4-(3-methylphenyl)-1-piperazinyl]-3-[3-(trifluoromethyl)phenyl]-3,4-dihydro-4-quinazolinyl}acetic acd

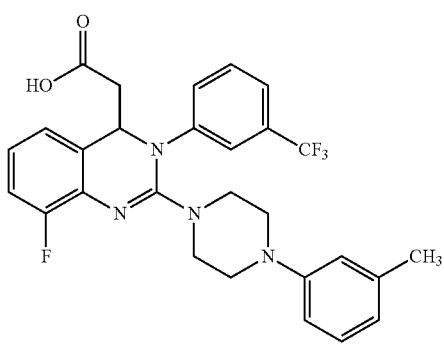 [SMILES: Cc1cccc(N2CCN(C3=Nc4c(F)cccc4C(CC(=O)O)N3c3cccc(C(F)(F)F)c3)CC2)c1]

Starting with 34 mg (0.06 mmol) of the methyl ester from Example 23A, the general procedure [H] gives 30 mg (90% of theory) of product.

HPLC (Method 1): $R_t$=4.56 min

MS (ESI-pos): m/z=526.9 (M+H)$^+$ $^1$H NMR (200 MHz, DMSO-d$_6$): δ [ppm]=7.64 (s, 1H); 7.53 (t, 1H); 7.44-7.34 (m, 2H); 7.11-6.90 (m, 3H); 6.72-6.59 (m, 4H); 5.33-5.25 (m, 1H); 3.52 (d$_b$, 4H); 3.02 (d$_b$, 4H); 2.69-2.55 (m, 2H, partially obscured by DMSO signal); 2.23 (s, 3H).

Example 4

{8-Fluoro-2-[4-(3-methoxyphenyl)-1-piperazinyl]-3-[3-(trifluoromethyl)phenyl]-3,4-dihydro-4-quinazolinyl}acetic acid

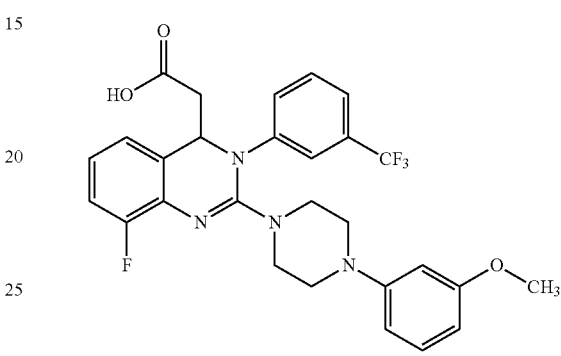

Starting with 36 mg (0.07 mmol) of the methyl ester from Example 25A, the general procedure [H] and chromatography (Method 2) give 28 mg (77% of theory) of product.

HPLC (Method 1): $R_t$=4.46 min

MS (ESI-pos): m/z=542.9 (M+H)$^+$ $^1$H NMR (200 MHz, DMSO-d$_6$): δ [ppm]=7.67 (s, 1H); 7.54 (t, 1H); 7.45-7.38 (m, 2H); 7.14-6.94 (m, 3H); 6.51-6.35 (m, 4H); 5.35-5.25 (m, 1H); 3.69 (s, 3H); 3.50 (d$_b$, 4H); 3.06 (d$_b$, 4H); 2.58-2.52 (m, 2H).

Example 5

{8-Fluoro-2-[4-(3-chlorophenyl)-1-piperazinyl]-3-[3-(trifluoromethyl)phenyl]-3,4-dihydro-4-quinazolinyl}acetic acid

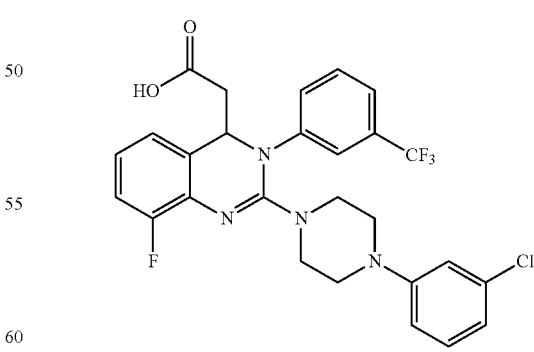

Starting with 38 mg (0.07 mmol) of the methyl ester from Example 35A, the general procedure [H] gives 25 mg (66% of theory) of product.

HPLC (Method 1): $R_t$=4.64 min

MS (ESI-pos): m/z=546.9 (M+H)$^+$

¹H NMR (200 MHz, DMSO-d₆): δ [ppm]=7.66 (s, 1H); 7.52 (t, 1H); 7.38 (dd, 2H); 7.20 (t, 1H); 7.10-6.78 (m, 6H); 5.33-5.26 (m, 1H); 3.51 (d_b, 4H); 3.11 (d_b, 4H); 2.61-2.55 (m, 2H).

Example 6

{8-Fluoro-2-[4-(1,3-benzodioxol-5-yl)-1-piperazinyl]-3-[3-(trifluoromethyl)phenyl]-3,4-dihydro-4-quinazolinyl}acetic acid

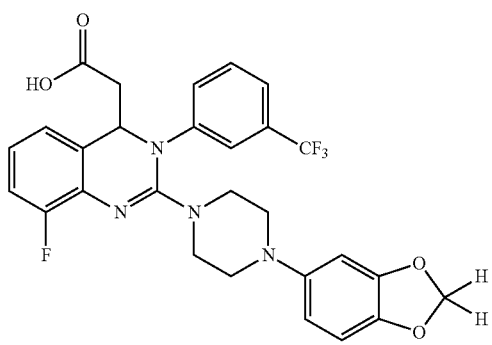 [SMILES: O=C(O)CC1c2cccc(F)c2N=C(N2CCN(c3ccc4c(c3)OCO4)CC2)N1c1cccc(C(F)(F)F)c1]

Starting with 173 mg (0.30 mmol) of the methyl ester from Example 36A, the general procedure [H] gives 79 mg (46% of theory) of product.

HPLC (Method 1): R_t=4.44 min

MS (ESI-pos): m/z=557.2 (M+H)⁺

¹H NMR (300 MHz, CDCl₃): δ [ppm]=7.47 (s, 1H); 7.42-7.34 (m, 3H); 7.03-6.89 (m, 2H); 6.79 (d, 1H); 6.64 (d, 1H); 6.41 (d, 1H); 6.22 (dd, 1H); 5.87 (s, 2H); 5.20-5.15 (m, 1H); 3.59 (s_b, 3H); 2.94-2.85 (m, 5H); 2.59 (dd, 1H).

Example 7

{6-Fluoro-2-[4-(4-fluorophenyl)-1-piperazinyl]-3-[3-(trifluoromethyl)phenyl]-3,4-dihydro-4-quinazolinyl}acetic acid

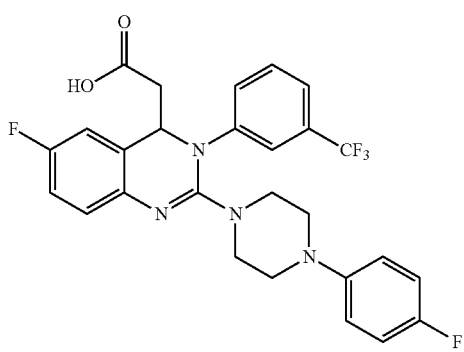 [SMILES: O=C(O)CC1c2cc(F)ccc2N=C(N2CCN(c3ccc(F)cc3)CC2)N1c1cccc(C(F)(F)F)c1]

Starting with 42 mg (0.08 mmol) of the methyl ester from Example 21A, the general procedure [H] gives 34 mg (76% of theory) of product.

HPLC (Method 1): R_t=4.63 min

MS (ESI-pos): m/z=530.9 (M+H)⁺

Example 8

{6-Fluoro-2-[4-(4-fluorophenyl)-1-piperazinyl]-3-[3-(trifluoromethyl)phenyl]-3,4-dihydro-4-quinazolinyl}acetic acid hydrochloride

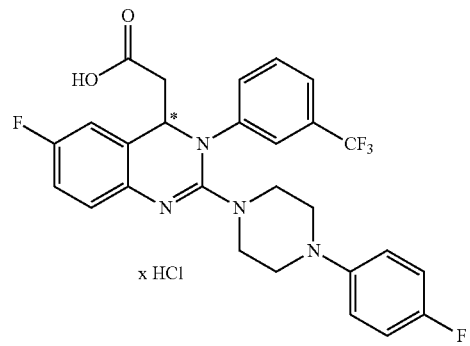 [SMILES: O=C(O)CC1c2cc(F)ccc2N=C(N2CCN(c3ccc(F)cc3)CC2)N1c1cccc(C(F)(F)F)c1]

Starting with 350 mg (0.64 mmol) of the ester from Example 22A, the general procedure [H] gives 284 mg (83% of theory) of product.

HPLC (Method 1): R_t=4.53 min

MS (ESI-pos): m/z=530.8 (M+H—HCl)⁺

¹H NMR (400 MHz, CD₃CN): δ [ppm]=7.62 (s, 1H); 7.51-7.48 (m, 1H); 7.43-7.41 (d, 1H); 7.26-7.23 (m, 1H); 7.04-6.95 (m, 2H); 6.91-6.85 (m, 3H); 5.23 (dd, 1H); 3.55 (s_b, 3H); 3.02-2.99 (m, 1H); 2.94 (s_b, 4H); 2.80 (dd, 1H).

Example 9

{8-Fluoro-2-[4-(3-methylphenyl)-1-piperazinyl]-3-[3-(trifluoromethyl)phenyl]-3,4-dihydro-4-quinazolinyl}acetic acid hydrochloride

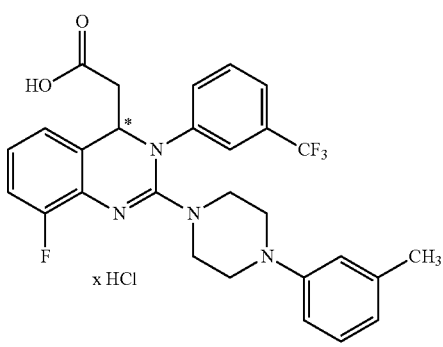 [SMILES: Cc1cccc(N2CCN(C3=Nc4c(F)cccc4C(CC(=O)O)N3c3cccc(C(F)(F)F)c3)CC2)c1]

Starting with 1.10 g (1.93 mmol) of the ester from Example 24A, the general procedure [H] gives 1.04 g (91% of theory) of product. Following the separation of enantiomers by Method 4, the product is obtained as enantiomer A.

HPLC (Method 1): R_t=4.68 min

MS (ESI-pos): m/z=526.9 (M+H—HCl)⁺

¹H NMR (400 MHz, CD₃CN): δ [ppm]=7.61 (s, 1H); 7.49-7.38 (m, 3H); 7.10-6.89 (m, 4H); 6.71-6.65 (m, 3H); 5.26 (dd, 1H); 3.60-3.52 (m, 4H); 3.03-2.95 (m, 4H); 2.76 (dd, 1H); 2.57 (dd, 1H); 2.25 (s, 3H).

Example 10

{8-Fluoro-2-[4-(3-methoxyphenyl)-1-piperazinyl]-3-[3-(trifluoromethyl)phenyl]-3,4-dihydro-4-quinazolinyl}acetic acid hydrochloride

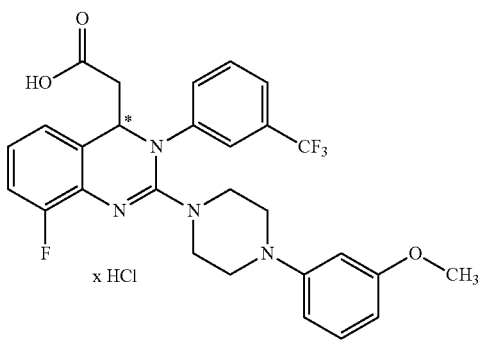 [SMILES: COc1cccc(N2CCN(C3=Nc4c(F)cccc4C(CC(=O)O)N3c3cccc(C(F)(F)F)c3)CC2)c1]

Starting with 437 mg (0.79 mmol) of the ester from Example 26A, the general procedure [H] gives 344 mg (72% of theory) of product.

HPLC (Method 1): R$_t$=4.48 min

MS (ESI-pos): m/z=543.0 (M+H—HCl)⁺

¹H NMR (400 MHz, CD₃CN): δ [ppm]=7.61 (s, 1H); 7.49-7.38 (m, 3H); 7.14-6.89 (m, 4H); 6.47-6.39 (m, 3H); 5.26 (dd, 1H); 3.72 (s, 1H); 3.60-3.54 (m, 4H); 3.07-3.00 (m, 4H); 2.77 (dd, 1H); 2.57 (dd, 1H).

Example 11

{8-Fluoro-2-[4-(4-fluoro-3-methylphenyl)-1-piperazinyl]-3-[6-methoxy-3-(trifluoromethyl)-phenyl]-3,4-dihydro-4-quinazolinyl}acetic acid hydrochloride

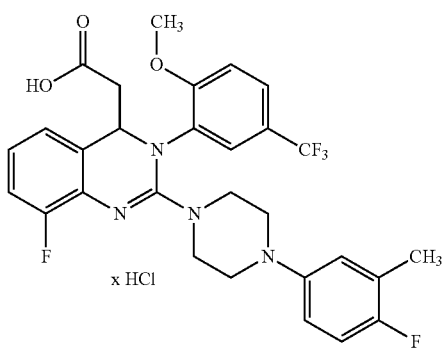 [SMILES: COc1ccc(C(F)(F)F)cc1N1C(N2CCN(c3ccc(F)c(C)c3)CC2)=Nc2c(F)cccc2C1CC(=O)O]

Starting with 1.03 g (1.75 mmol) of the crude product of the ester from Example 27A, the general procedure [H] and chromatography according to Method 5 followed by dissolution of the product in methanol/1N hydrochloric acid and re-evaporation of the solvent give 283 mg (22% of theory) of hydrochloride.

HPLC (Method 1): R$_t$=4.58 min

MS (ESI-pos): m/z=575.2 (M+H—HCl)⁺

¹H NMR (400 MHz, CD₃CN): δ [ppm]=8.17 (s, 0.66H); 7.69 (d, 1H); 7.55-7.30 (m, 1H); 7.27-7.24 (m, 2H); 7.16 (d, 0.6H); 7.09-7.04 (m, 2H); 5.33-5.27, 5.12-5.06 (2×m, 1H); 4.08-3.35 (m, 4H); 3.69 (s, 3H); 3.30-3.22 (m, 1H); 2.80-2.76 (m, 1H); 2.25 (s, 3H).

Example 12

{8-Fluoro-2-[4-(4-fluoro-3-methylphenyl)-1-piperazinyl]-3-[6-methoxy-3-(trifluoromethyl)-phenyl]-3,4-dihydro-4-quinazolinyl}acetic acid hydrochloride

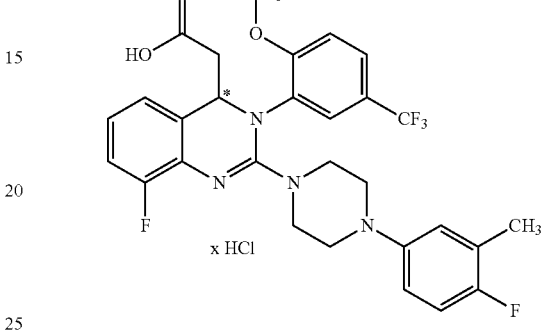

Prior to the separation of enantiomers, 268 mg of the hydrochloride from Example 11 are taken up in dichloromethane, and the organic phase is extracted twice with saturated sodium bicarbonate solution. The combined aqueous phases are extracted once with dichloromethane, the combined organic phases are dried over sodium sulphate and filtered and the solvent is removed under reduced pressure. This gives 204 mg (86% of theory) of the free base. Using this material, separation of enantiomers (Method 4), re-purification by preparative HPLC (Method 5) and subsequent dissolution of the product in methanol/1N hydrochloric acid and re-evaporation of the solvent gives 80 mg (78% of theory) of enantiomer A.

HPLC (Method 6): R$_t$=4.66 min

MS (ESI-pos): m/z=575.2 (M+H—HCl)⁺

¹H NMR (400 MHz, CD₃CN): δ [ppm]=8.17 (s, 0.66H); 7.69 (d, 1H); 7.45-7.30 (m, 1H); 7.24 (d, 2H); 7.15 (d, 0.7H); 7.08-7.01 (m, 2H); 5.32-5.27, 5.11-5.07 (2×m, 1H); 4.06-3.50 (m, 4H); 3.68 (s, 3H); 3.33-3.24 (m, 1H); 2.77-2.72 (m, 1H); 2.24, 2.23 (2×s, 3H).

Example 13

{8-Fluoro-2-[4-(4-fluoro-3-methylphenyl)-1-piperazinyl]-3-[6-methoxy-3-methylphenyl]-3,4-dihydro-4-quinazolinyl}acetic acid hydrochloride

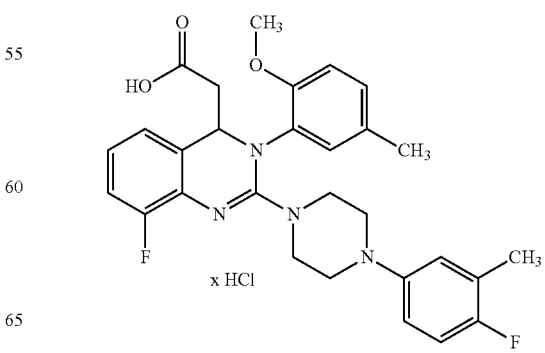

Starting with 183 mg (0.34 mmol) of the crude product of the ester from Example 28A, the general procedure [H] and chromatography according to Method 5 followed by dissolution of the product in methanol/1N hydrochloric acid and re-evaporation of the solvent give 135 mg (67% of theory) of hydrochloride.

HPLC (Method 1): $R_t$=4.67 min
MS (ESI-pos): m/z=521.2 (M+H—HCl)$^+$
$^1$H NMR (400 MHz, CD$_3$CN): δ [ppm]=7.69-7.42 (m, 4H); 7.25-7.06 (m, 5H); 6.93-6.78 (m, 1H); 5.24-5.21, 5.06-5.03 (2×m, 1H); 4.00-3.35 (m, 8H); 3.21-3.08 (m, 1H); 3.01-2.77 (m, 1H); 2.34, 2.20 (2×s, 3H); 2.26 (s, 3H).

Example 14

{8-Fluoro-2-[4-(3-methoxyphenyl)-1-piperazinyl]-3-[2-methoxy-5-(trifluoromethyl)phenyl]-3,4-dihydro-4-quinazolinyl}acetic acid

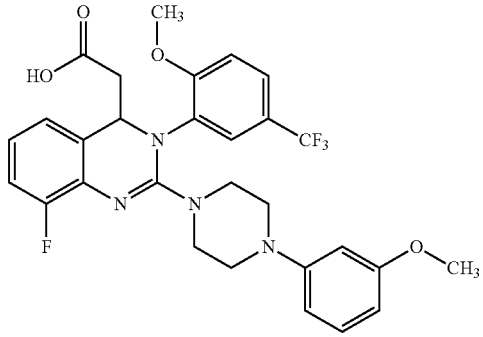

At room temperature, 179.6 mg (4.49 mmol) of sodium hydroxide are added to 878 mg (1.5 mmol) of methyl {8-fluoro-2-[4-(3-methoxyphenyl)-1-piperazinyl]-3-[2-methoxy-5-(trifluoromethyl)phenyl]-3,4-dihydro-4-quinazolinyl}acetate (Example 31A) in 40 ml of dioxane, and the mixture is stirred at 50° C. for 2 hours. The pH is then adjusted to 4-5. The product is filtered off, washed with water and dried under reduced pressure.

Yield: 801 mg (93% of theory)
HPLC (Method 1): $R_t$=4.5 min
MS (ESI-pos): m/z=573 (M-1-H)$^+$ Example 15

{8-Fluoro-2-[4-(3-methoxyphenyl)-1-piperazinyl]-3-[2-methoxy-5-(trifluoromethyl)phenyl]-3,4-dihydro-4-quinazolinyl}acetic acid

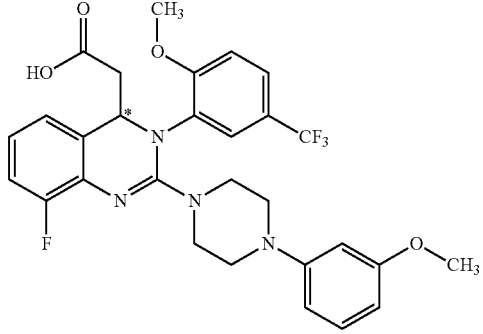

After separation of enantiomers (Method 11) of 500 mg of racemate (Example 14), the crude product is purified by chromatography on silica gel and then dissolved in 1N aqueous sodium hydroxide solution and extracted with diethyl ether. Following acidification with 1N hydrochloric acid, the product is filtered off and dried under reduced pressure.

Yield: 105 mg (21% of theory)
MS (ESI-pos): m/z=573 (M+H)$^+$
$^1$H NMR (300 MHz, DMSO-d$_6$): δ [ppm]=2.4-2.5 (m, 1H); 2.7-3.1 (m, 5H); 3.3-3.6 (m, 4H); 3.7 (s, 3H); 3.7-3.9 (s$_b$, 3H); 4.8-5.05 (s$_b$, 1H); 6.3-6.4 (m, 2H); 6.4-6.5 (m, 1H); 6.8-7.65 (m, 6H); 12.5 (s$_b$, 1H).

Alternatively, the target product is obtained by reacting the enantiomerically pure ester from Example 43A according to the general procedure [H]. Starting with 111 g (0.19 mol) of ester, 69 g (63% of theory) of target product are obtained.

Example 16

{8-Fluoro-2-[4-(3,4-difluorophenyl)-1-piperazinyl]-3-[2-methoxy-5-(trifluoromethyl)phenyl]-3,4-dihydro-4-quinazolinyl}acetic acid

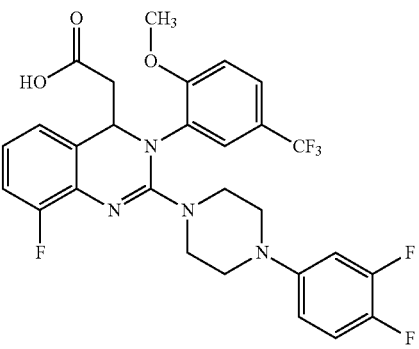 [SMILES: COc1ccc(C(F)(F)F)cc1N1C(N2CCN(c3ccc(F)c(F)c3)CC2)=Nc2c(F)cccc2C1CC(=O)O]

In 40 ml of dioxane, 881 mg (1.49 mmol) of methyl {8-fluoro-2-[4-(3,4-difluorophenyl)-1-piperazinyl]-3-[2-methoxy-5-(trifluoromethyl)phenyl]-3,4-dihydro-4-quinazolinyl}acetate (Example 32A) and 178 mg (4.46 mmol) of sodium hydroxide are stirred at 50° C. for 2 hours. Following acidification with 1N hydrochloric acid, the product is filtered off with suction, washed with water and dried under reduced pressure.

Yield: 775 mg (90% of theory)
HPLC (Method 1): $R_t$=4.5 min
MS (ESI-pos): m/z=579 (M+H)$^+$ Example 17

{8-Fluoro-2-[4-(3,4-difluorophenyl)-1-piperazinyl]-3-[2-methoxy-5-(trifluoromethyl)phenyl]-3,4-dihydro-4-quinazolinyl}acetic acid

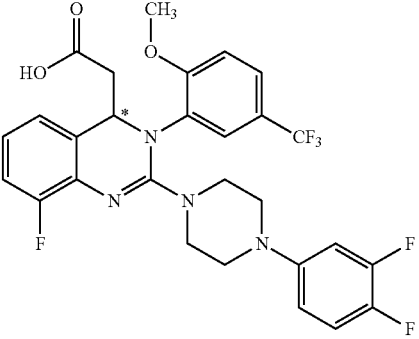 [SMILES: COc1ccc(C(F)(F)F)cc1N1C(N2CCN(c3ccc(F)c(F)c3)CC2)=Nc2c(F)cccc2C1CC(=O)O]

Following the separation of enantiomers (Method 12) of 500 mg (0.86 mmol) of racemate (Example 16), the crude product is purified by chromatography on silica gel (dichloromethane, dichloromethane/methanol 20:1, 10:1), dissolved in 1N aqueous sodium hydroxide solution and extracted with diethyl ether. Using 1N hydrochloric acid the aqueous phase is adjusted to pH 4-5, and the product is filtered off, washed with water and dried under reduced pressure.

Yield: 86 mg (17% of theory)

MS (ESI-pos): m/z=579 (M+H)$^+$ $^1$H NMR (300 MHz, DMSO-d$_6$): δ [ppm]=2.6-3.1 (m, 6H); 3.25-3.6 (m, 4H); 3.75 (s$_b$, 3H); 4.85 (s$_b$, 1H); 6.6-6.7 (m, 1H); 6.7-7.7 (m, 9H); 12.5 (s$_b$, 1H).

Example 18

{8-Fluoro-2-[4-(4-fluorophenyl)-1-piperazinyl]-3-[2-methoxy-5-(trifluoromethyl)phenyl]-3,4-dihydro-4-quinazolinyl}acetic acid

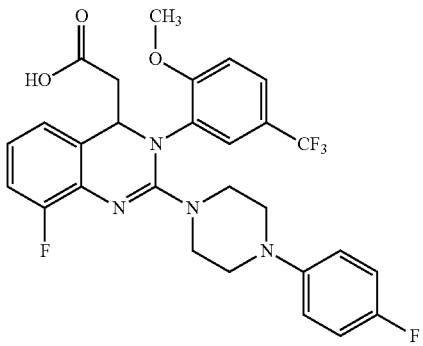 [SMILES: COc1ccc(C(F)(F)F)cc1N1C(N2CCN(c3ccc(F)cc3)CC2)=Nc2c(F)cccc2C1CC(=O)O]

In 800 ml of dioxane, 15 g (26.11 mmol) of methyl {8-fluoro-2-[4-(4-fluorophenyl)-1-piperazinyl]-3-[2-methoxy-5-(trifluoromethyl)phenyl]-3,4-dihydro-4-quinazolinyl}acetate (Example 30A) and 3.13 g (78.32 mmol) of sodium hydroxide are stirred at 50° C. for 4 hours. Following distillative removal of the solvent, the residue is dissolved in 500 ml of water and acidified and the precipitate is filtered off with suction. The product is washed with water and dried under reduced pressure.

Yield: 14.5 g (99% of theory)

HPLC (Method 1): R$_t$=4.5 min

MS (ESI-pos): m/z=561 (M+H)$^+$

Example 19

{8-Fluoro-2-[4-(4-fluorophenyl)-1-piperazinyl]-3-[2-methoxy-5-(trifluoromethyl)phenyl]-3,4-dihydro-4-quinazolinyl}acetic acid

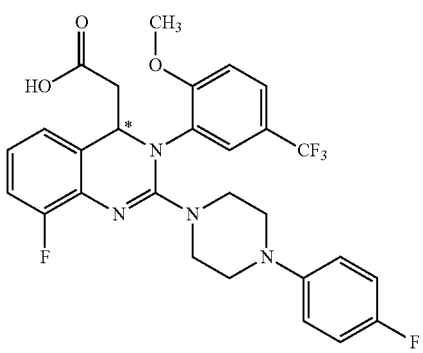 [SMILES: COc1ccc(C(F)(F)F)cc1N1C(N2CCN(c3ccc(F)cc3)CC2)=Nc2c(F)cccc2C1CC(=O)O]

14.2 g (25.33 mmol) of racemate (Example 18) are separated (Method 13). The crude product is dissolved in 250 ml of 0.5N sodium hydroxide solution and then purified by extraction with diethyl ether. After acidification of the aqueous phase with hydrochloric acid, the product is filtered off, washed with water and dried under reduced pressure.

Yield: 5.85 g (41% of theory)

MS (ESI-pos): m/z=561 (M+H)$^+$

HPLC (Method 1): R$_t$=4.5 min $^1$H NMR (400 MHz, DMSO-d$_6$): δ [ppm]=2.6-3.0 (m, 6H); 3.3-3.6 (m, 4H); 3.6-4.0 (s$_b$, 3H); 4.8-5.2 (s$_b$, 1H); 6.7-7.75 (m, 10H); 12.2-12.8 (s$_b$, 1H).

Alternatively, the target product is obtained by reacting the enantiomerically pure ester from Example 42A according to the general procedure [H]. Starting with 120 g (0.21 mol) of ester, 96 g (81% of theory) of target product are obtained.

Example 20

{8-Fluoro-2-[4-(3-methylphenyl)-1-piperazinyl]-3-[2-methoxy-5-(trifluoromethyl)phenyl]-3,4-dihydro-4-quinazolinyl}acetic acid

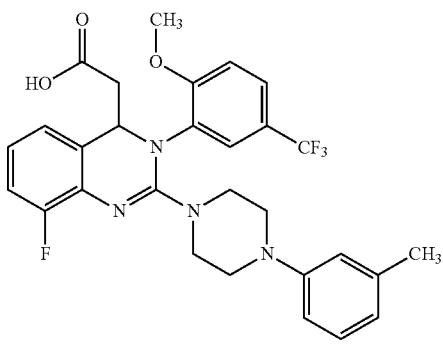

In 40 ml of dioxane, 892 mg (1.56 mmol) of methyl {8-fluoro-2-[4-(3-methylphenyl)-1-piperazinyl]-3-[2-methoxy-5-(trifluoromethyl)phenyl]-3,4-dihydro-4-quinazolinyl}acetate (Example 33A) and 187.6 mg (4.69 mmol) of sodium hydroxide are stirred at 50° C. for 2 hours. Following removal of the solvent, the residue is taken up in water and adjusted to pH 4-5 using 1N hydrochloric acid. The product is filtered off and then washed with water and dried under reduced pressure.

Yield: 788 mg (91% of theory)

MS (ESI-pos): m/z=557 (M+H)$^+$

HPLC (Method 6): R$_t$=4.5 min

Example 21

{8-Fluoro-2-[4-(3-methylphenyl)-1-piperazinyl]-3-[2-methoxy-5-(trifluoromethyl)phenyl]-3,4-dihydro-4-quinazolinyl}acetic acid

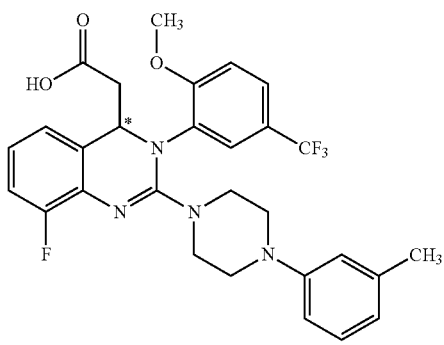

The separation of enantiomers (Method 13) is carried out using 500 mg (0.9 mmol) of racemate (Example 20). The crude product is then dissolved in 1N aqueous sodium hydroxide solution, the solution is extracted with diethyl ether and the aqueous phase is adjusted to pH 4-5 using 1N hydrochloric acid. The product is filtered off with suction, washed with water and dried under reduced pressure.

Yield: 104 mg (21% of theory)

MS (ESI-pos): m/z=557 (M+H)$^+$ $^1$H NMR (400 MHz, DMSO-d$_6$): δ [ppm]=2.2 (s$_b$, 3H); 2.35-2.5 (m, 1H); 2.6-3.1 (m, 5H); 3.3-3.6 (m, 4H); 3.8 (s$_b$, 3H); 4.9 (s$_b$, 1H); 6.5-6.7 (m, 3H); 6.8-7.7 (m, 7H); 12.6 (s$_b$, 1H).

Example 22

{8-Fluoro-2-[4-(4-fluorophenyl)-1-piperazinyl]-3-[6-methoxy-3-chlorophenyl]-3,4-dihydro-4-quinazolinyl}acetic acid hydrochloride

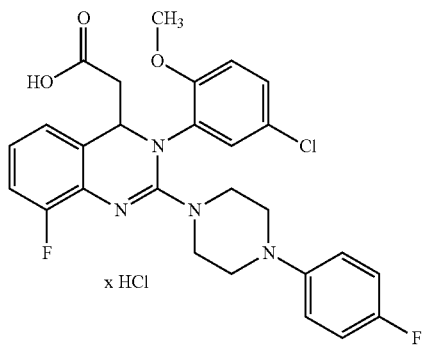 [SMILES: COc1ccc(Cl)cc1N1C(N2CCN(c3ccc(F)cc3)CC2)=Nc2c(F)cccc2C1CC(=O)O]

Starting with 621 mg (1.15 mmol) of the ester from Example 29A, the general procedure [H] and purification by preparative HPLC (Method 5) and coevaporation with methanol/1N hydrochloric acid give 330 mg (51% of theory) of product.

HPLC (Method 1): R$_t$=4.58 min

MS (ESI-pos): m/z=527.0 (M+H—HCl)$^+$

Example 23

{8-Fluoro-2-[4-(4-fluorophenyl)-1-piperazinyl]-3-[6-methoxy-3-chlorophenyl]-3,4-dihydro-4-quinazolinyl}acetic acid hydrochloride

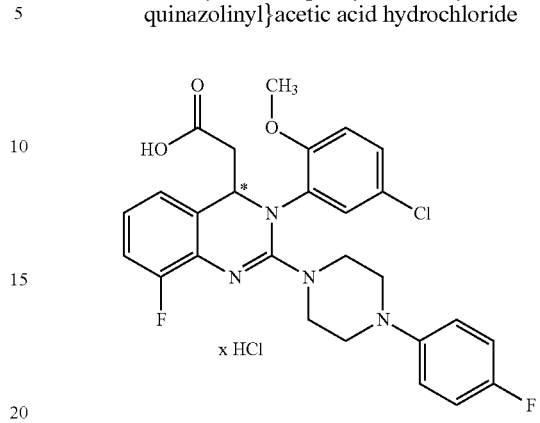

Starting with 320 mg (0.06 mmol) of the racemate from Example 22, chromatographic separation of enantiomers (Method 4) and subsequent dissolution of the product in methanol/1N hydrochloric acid and re-evaporation of the solvent give 174 mg (50% of theory) of hydrochloride.

HPLC (Method 1): R$_t$=4.51 min

MS (ESI-pos): m/z=527.1 (M+H—HCl)$^+$ $^1$H NMR (400 MHz, CD$_3$CN): δ [ppm]=7.29 (dd, 1H); 7.19-7.11 (m, 2H); 7.01-6.94 (m, 4H); 6.87-6.83 (m, 2H); 5.08 (t, 1H); 3.67 (s, 3H); 3.56 (s, 4H); 3.03-2.92 (m, 5H); 2.72 (dd, 1H).

Example 24

{8-Fluoro-2-[4-(3-fluorophenyl)-1-piperazinyl]-3-[2-methoxy-5-(trifluoromethyl)phenyl]-3,4-dihydro-4-quinazolinyl}acetic acid

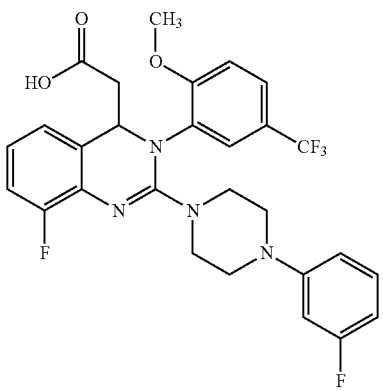 [SMILES: COc1ccc(C(F)(F)F)cc1N1C(N2CCN(c3cccc(F)c3)CC2)=Nc2c(F)cccc2C1CC(=O)O]

In 15 ml of dioxane, 117 mg (0.2 mmol) of methyl {8-fluoro-2-[4-(3-fluorophenyl)-1-piperazinyl]-3-[2-methoxy-5-(trifluoromethyl)phenyl]-3,4-dihydro-4-quinazolinyl}acetate (Example 34A) are mixed with 0.61 ml of 1N aqueous sodium hydroxide solution, and the mixture is stirred at 50° C. for 3 hours. After removal of the solvent, the residue is taken up in water and the mixture is adjusted to pH 3-4 using 1N hydrochloric acid. The precipitate is filtered off with suction, washed with water and dried under reduced pressure.

Yield: 76 mg (67% of theory)

HPLC (Method 1): R$_t$=4.6 min

MS (ESI-pos): m/z=561 (M+H)$^+$

Example 25

{8-Fluoro-2-[4-(3-fluorophenyl)-1-piperazinyl]-3-[2-methoxy-5-(trifluoromethyl)phenyl]-3,4-dihydro-4-quinazolinyl}acetic acid

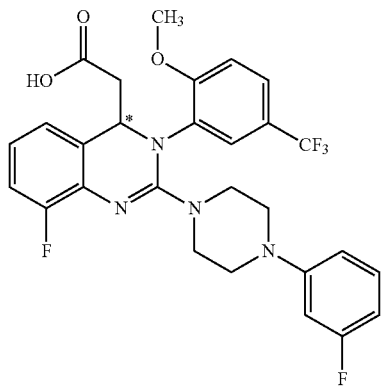 [SMILES: COc1ccc(C(F)(F)F)cc1N1C(N2CCN(c3cccc(F)c3)CC2)=Nc2c(F)cccc2C1CC(=O)O]

52 mg (0.09 mmol) of the racemate (Example 24) are separated into the enantiomers (Method 13). The crude product is then purified by chromatography on silica gel (acetic acid, dichloromethane/methanol 10:1) and dried under reduced pressure.

Yield: 12.3 mg (24% of theory)

LC-MS (Method 7): $R_t$=2.50 min

MS (ESI-pos): m/z=561 (M+H)$^+$ $^1$H NMR (400 MHz, DMSO-$d_6$): δ [ppm]=2.35-2.5 (m, 1H); 2.7-3.1 (m, 5H); 3.3-3.6 (m, 4H); 3.8 ($s_b$, 3H); 4.8-4.9 (m, 1H); 6.45-6.6 (m, 1H); 6.6-6.7 (m, 2H); 6.8-6.9 (m, 2H); 6.98-7.1 (m, 1H); 7.1-7.6 (m, 4H); 12.4 ($s_b$, 1H).

Examples 26 to 34 and 36 to 89 of Table 2 can be prepared from the corresponding starting materials using the general procedures [A] to [H], and Example 35 can be prepared as described below in Table 2.

TABLE 2

| Example No. | Structure | Molecular weight [g/mol] | Starting material Example | $R_t$ [min] | HPLC Method | MS |
|---|---|---|---|---|---|---|
| 26 | (structure) | 597.0 | 50A | 4.53 | 1 | 561 [M + H − HCl]$^+$ |
| 27 | (structure) x HCl | 592.0 | 51A | 4.22 | 1 | 556 [M + H − HCl]$^+$ |

TABLE 2-continued

| Example No. | Structure | Molecular weight [g/mol] | Starting material Example | $R_t$ [min] | HPLC Method | MS |
|---|---|---|---|---|---|---|
| 28 | (structure) × HCl | 588.0 | 52A | 4.36 | 1 | 552 [M + H − HCl]⁺ |
| 29 | (structure) × HCl | 608.4 | 53A | 4.37 | 1 | 572 [M + H − HCl]⁺ |
| 30 | (structure) × HCl | 584.9 | 54A | 4.54 | 1 | 548 [M + H − HCl]⁺ |
| 31 | (structure) × HCl | 604.0 | 55A | 4.27 | 1 | 568 [M + H − HCl]⁺ |

TABLE 2-continued

| Example No. | Structure | Molecular weight [g/mol] | Starting material Example | R$_t$ [min] | HPLC Method | MS |
|---|---|---|---|---|---|---|
| 32 | 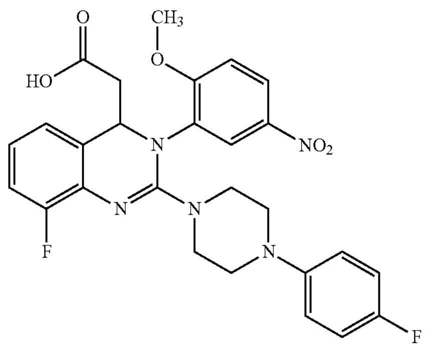 [SMILES: COc1ccc([N+](=O)[O-])cc1N1C(N2CCN(c3ccc(F)cc3)CC2)=Nc2c(F)cccc2C1CC(=O)O] | 537.5 | 56A | 4.30 | 1 | 538 [M + H]$^+$ |
| 33 | 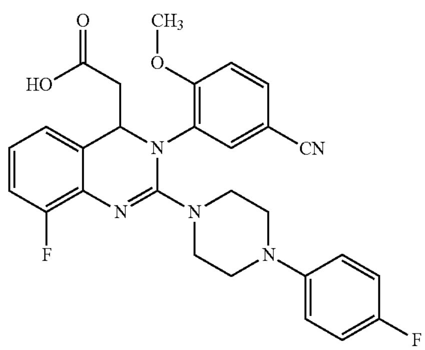 [SMILES: COc1ccc(C#N)cc1N1C(N2CCN(c3ccc(F)cc3)CC2)=Nc2c(F)cccc2C1CC(=O)O] | 517.5 | 57A | 4.28 | 1 | 518 [M + H]$^+$ |
| 34 | 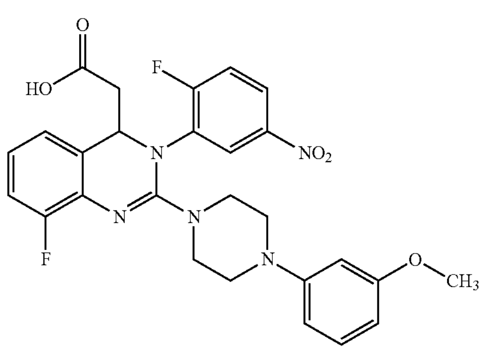 [SMILES: COc1cccc(N2CCN(C3=Nc4c(F)cccc4C(CC(=O)O)N3c3cc([N+](=O)[O-])ccc3F)CC2)c1] | 537.5 | 58A | 4.41 | 1 | 538 [M + H]$^+$ |
| 35 | 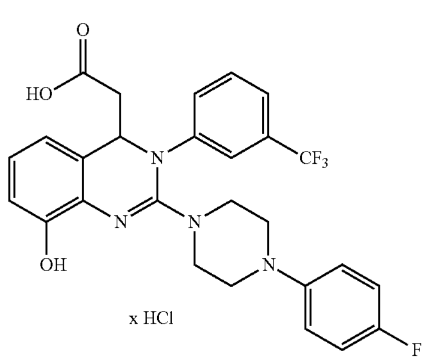 [SMILES: O=C(O)CC1c2cccc(O)c2N=C(N2CCN(c3ccc(F)cc3)CC2)N1c1cccc(C(F)(F)F)c1] | 565.0 | 89 | 4.47 | 1 | 529 [M + H − HCl]$^+$ |

TABLE 2-continued

| Example No. | Structure | Molecular weight [g/mol] | Starting material Example | R$_t$ [min] | HPLC Method | MS |
|---|---|---|---|---|---|---|
| 36 | 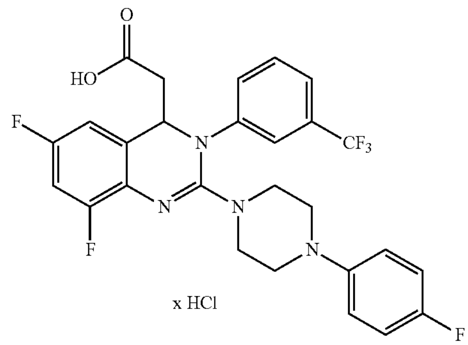 [SMILES: O=C(O)CC1c2cc(F)cc(F)c2N=C(N2CCN(c3ccc(F)cc3)CC2)N1c1cccc(C(F)(F)F)c1] | 584.9 | 60A | 4.61 | 1 | 549 [M + H − HCl]$^+$ |
| 37 | 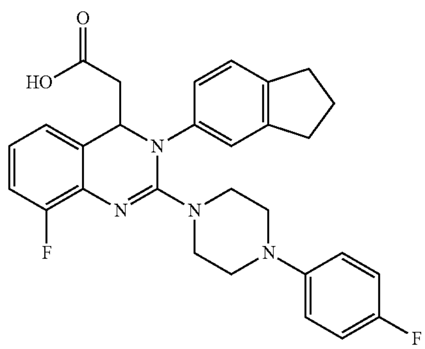 [SMILES: O=C(O)CC1c2cccc(F)c2N=C(N2CCN(c3ccc(F)cc3)CC2)N1c1ccc2c(c1)CCC2] | 502.6 | 61A | 4.6 | 1 | 503 [M + H]$^+$ |
| 38 | 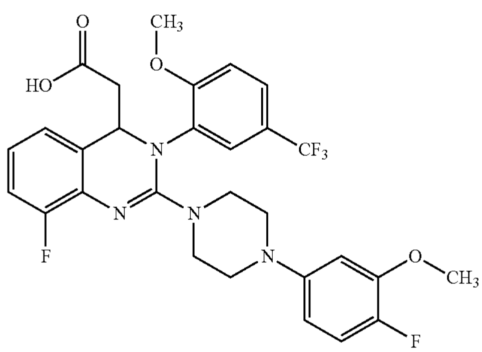 [SMILES: COc1cc(N2CCN(C3=Nc4c(F)cccc4C(CC(=O)O)N3c3cc(C(F)(F)F)ccc3OC)CC2)ccc1F] | 590.6 | 62A | 4.6 | 6 | 591 [M + H]$^+$ |
| 39 | 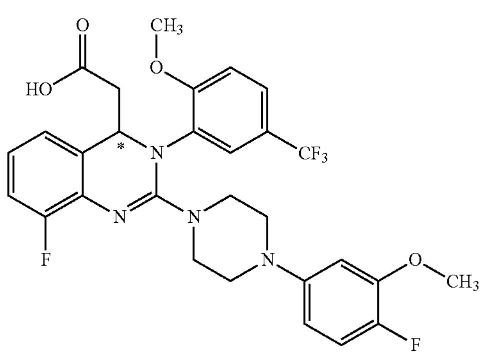 [SMILES: COc1cc(N2CCN(C3=Nc4c(F)cccc4C(CC(=O)O)N3c3cc(C(F)(F)F)ccc3OC)CC2)ccc1F] | 590.6 | 63A | 4.53 | 1 | 591 [M + H]$^+$ |

TABLE 2-continued

| Example No. | Structure | Molecular weight [g/mol] | Starting material Example | R$_t$ [min] | HPLC Method | MS |
|---|---|---|---|---|---|---|
| 40 | 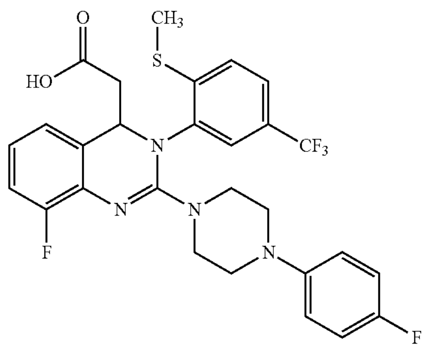 | 576.6 | 64A | 4.5 | 6 | 577 [M + H]$^+$ |
| 41 | 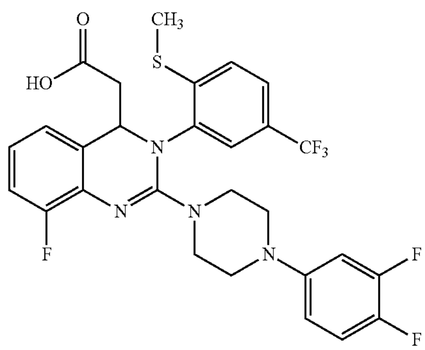 | 594.6 | 65A | 4.5 | 6 | 595 [M + H]$^+$ |
| 42 | 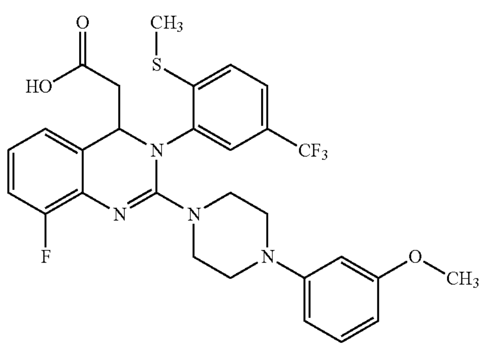 [SMILES: COc1cccc(N2CCN(C3=Nc4c(F)cccc4C(CC(=O)O)N3c3cc(C(F)(F)F)ccc3SC)CC2)c1] | 588.6 | 66A | 4.4 | 6 | 589 [M + H]$^+$ |
| 43 | 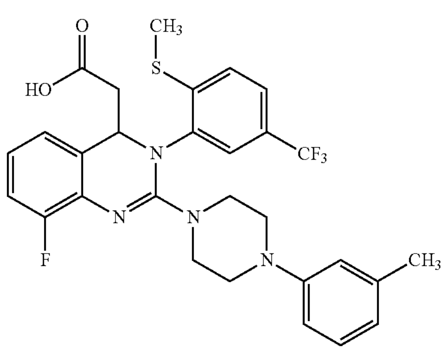 [SMILES: CSc1ccc(C(F)(F)F)cc1N1C(N2CCN(c3cccc(C)c3)CC2)=Nc2c(F)cccc2C1CC(=O)O] | 572.6 | 67A | 4.5 | 6 | 573 [M + H]$^+$ |

TABLE 2-continued

| Example No. | Structure | Molecular weight [g/mol] | Starting material Example | $R_t$ [min] | HPLC Method | MS |
|---|---|---|---|---|---|---|
| 44 | 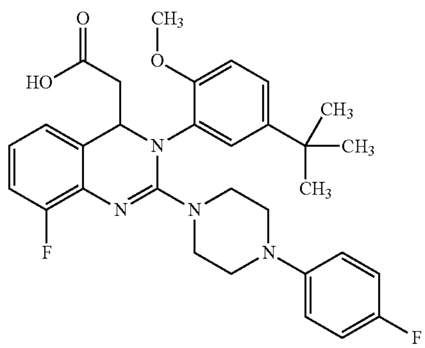 [SMILES: COc1ccc(C(C)(C)C)cc1N1C(N2CCN(c3ccc(F)cc3)CC2)=Nc2c(F)cccc2C1CC(=O)O] | 548.6 | 68A | 4.9 | 1 | 549 [M + H]$^+$ |
| 45 | 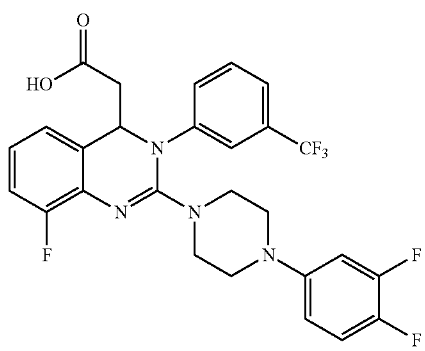 [SMILES: O=C(O)CC1c2cccc(F)c2N=C(N2CCN(c3ccc(F)c(F)c3)CC2)N1c1cccc(C(F)(F)F)c1] | 548.5 | 69A | 4.67 | 1 | 549 [M + H]$^+$ |
| 46 | 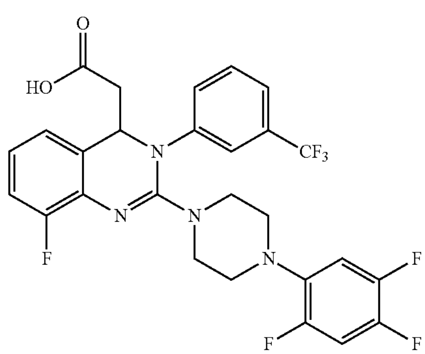 [SMILES: O=C(O)CC1c2cccc(F)c2N=C(N2CCN(c3cc(F)c(F)cc3F)CC2)N1c1cccc(C(F)(F)F)c1] | 566.5 | 70A | 4.60 | 1 | 567 [M + H]$^+$ |
| 47 | 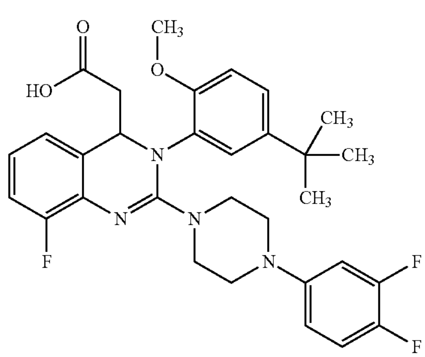 [SMILES: COc1ccc(C(C)(C)C)cc1N1C(N2CCN(c3ccc(F)c(F)c3)CC2)=Nc2c(F)cccc2C1CC(=O)O] | 566.6 | 71A | 4.9 | 1 | 567 [M + H]$^+$ |

TABLE 2-continued

| Example No. | Structure | Molecular weight [g/mol] | Starting material Example | R$_t$ [min] | HPLC Method | MS |
|---|---|---|---|---|---|---|
| 48 | 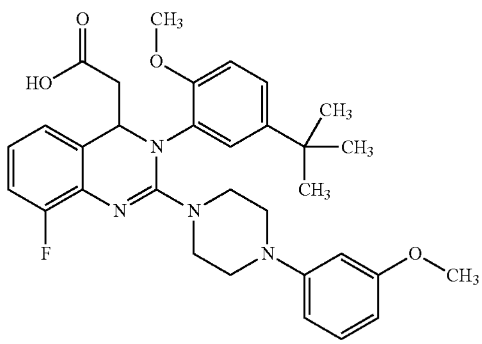 [SMILES: COc1cccc(N2CCN(C3=Nc4c(F)cccc4C(CC(=O)O)N3c3cc(C(C)(C)C)ccc3OC)CC2)c1] | 560.7 | 72A | 4.8 | 1 | 561 [M + H]$^+$ |
| 49 | 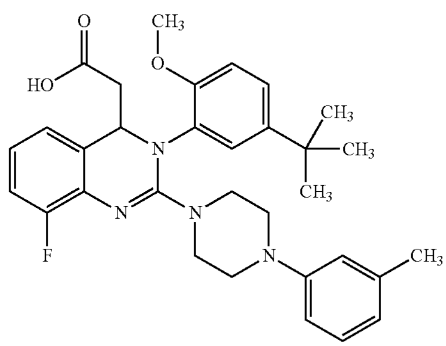 [SMILES: COc1ccc(C(C)(C)C)cc1N1C(N2CCN(c3cccc(C)c3)CC2)=Nc2c(F)cccc2C1CC(=O)O] | 544.7 | 73A | 5.0 | 1 | 545 [M + H]$^+$ |
| 50 | 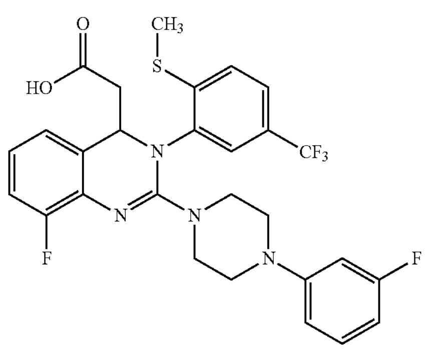 [SMILES: CSc1ccc(C(F)(F)F)cc1N1C(N2CCN(c3cccc(F)c3)CC2)=Nc2c(F)cccc2C1CC(=O)O] | 576.6 | 74A | 4.6 | 1 | 577 [M + H]$^+$ |
| 51 | 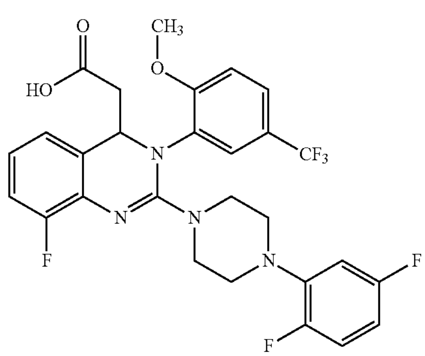 [SMILES: COc1ccc(C(F)(F)F)cc1N1C(N2CCN(c3cc(F)ccc3F)CC2)=Nc2c(F)cccc2C1CC(=O)O] | 578.5 | 75A | 4.7 | 1 | 579 [M + H]$^+$ |

TABLE 2-continued

| Example No. | Structure | Molecular weight [g/mol] | Starting material Example | R$_t$ [min] | HPLC Method | MS |
|---|---|---|---|---|---|---|
| 52 | 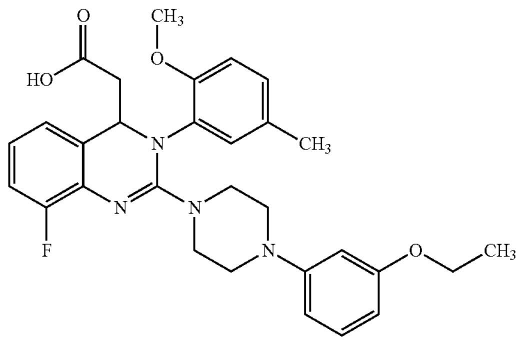 [SMILES: CCOc1cccc(N2CCN(C3=Nc4c(F)cccc4C(CC(=O)O)N3c3cc(C)ccc3OC)CC2)c1] | 532.6 | 76A | 4.6 | 1 | 561 [M + H]$^+$ |
| 53 | 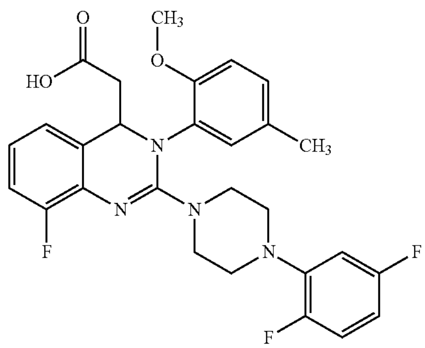 [SMILES: COc1ccc(C)cc1N1C(N2CCN(c3cc(F)ccc3F)CC2)=Nc2c(F)cccc2C1CC(=O)O] | 524.5 | 77A | 4.5 | 1 | 525 [M + H]$^+$ |
| 54 | 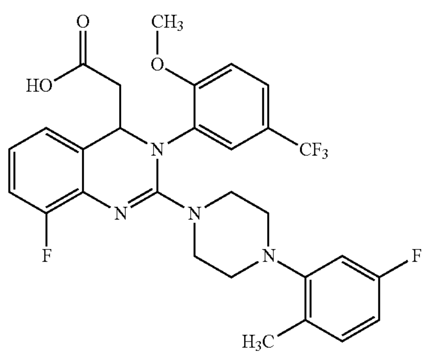 [SMILES: COc1ccc(C(F)(F)F)cc1N1C(N2CCN(c3cc(F)ccc3C)CC2)=Nc2c(F)cccc2C1CC(=O)O] | 574.6 | 78A | 4.7 | 1 | 575 [M + H]$^+$ |
| 55 | 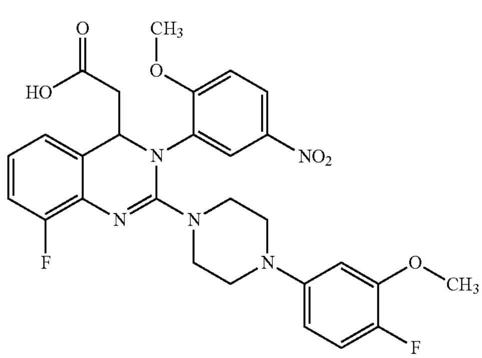 [SMILES: COc1cc(N2CCN(C3=Nc4c(F)cccc4C(CC(=O)O)N3c3cc([N+](=O)[O-])ccc3OC)CC2)ccc1F] | 567.6 | 79A | 4.3 | 1 | 568 [M + H]$^+$ |

TABLE 2-continued

| Example No. | Structure | Molecular weight [g/mol] | Starting material Example | R_t [min] | HPLC Method | MS |
|---|---|---|---|---|---|---|
| 56 | 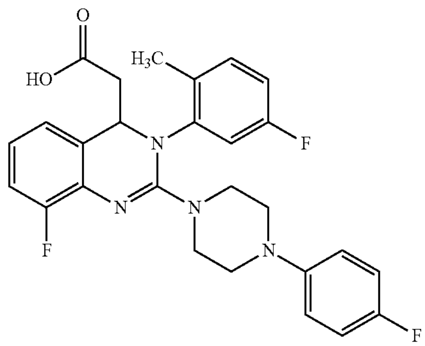 [SMILES: Cc1ccc(F)cc1N1C(N2CCN(c3ccc(F)cc3)CC2)=Nc2c(F)cccc2C1CC(=O)O] | 494.5 | 80A | 2.77 | 10 | 595 [M + H]⁺ |
| 57 | 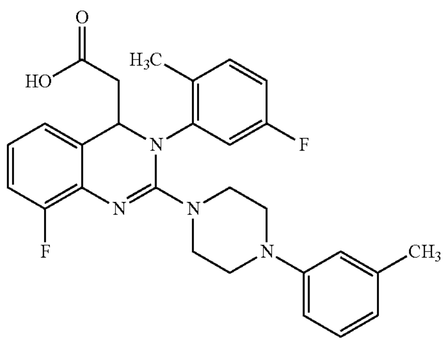 [SMILES: Cc1cccc(N2CCN(C3=Nc4c(F)cccc4C(CC(=O)O)N3c3cc(F)ccc3C)CC2)c1] | 490.6 | 81A | 1.94 | 9 | 591 [M + H]⁺ |
| 58 | 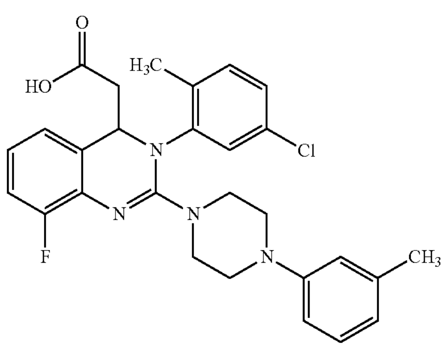 [SMILES: Cc1cccc(N2CCN(C3=Nc4c(F)cccc4C(CC(=O)O)N3c3cc(Cl)ccc3C)CC2)c1] | 507.0 | 82A | 1.97 | 9 | 507 [M + H]⁺ |
| 59 | 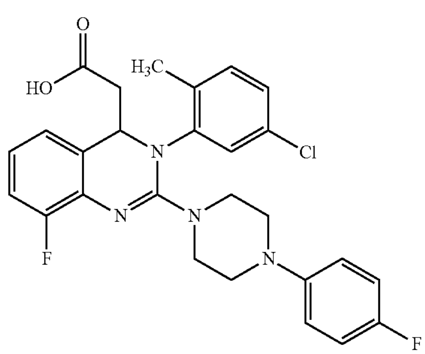 [SMILES: Cc1ccc(Cl)cc1N1C(N2CCN(c3ccc(F)cc3)CC2)=Nc2c(F)cccc2C1CC(=O)O] | 511.0 | 83A | 1.93 | 9 | 511 [M + H]⁺ |

TABLE 2-continued

| Example No. | Structure | Molecular weight [g/mol] | Starting material Example | R$_t$ [min] | HPLC Method | MS |
|---|---|---|---|---|---|---|
| 60 | 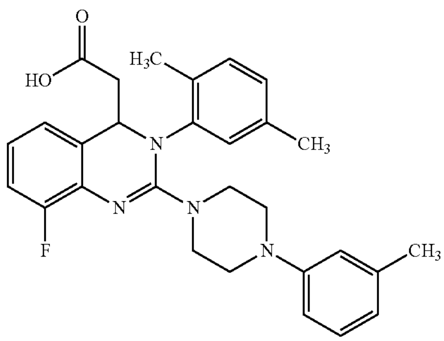 [SMILES: Cc1cccc(N2CCN(C3=Nc4c(F)cccc4C(CC(=O)O)N3c3cc(C)ccc3C)CC2)c1] | 486.6 | 84A | 1.90 | 9 | 587 [M + H]$^+$ |
| 61 | 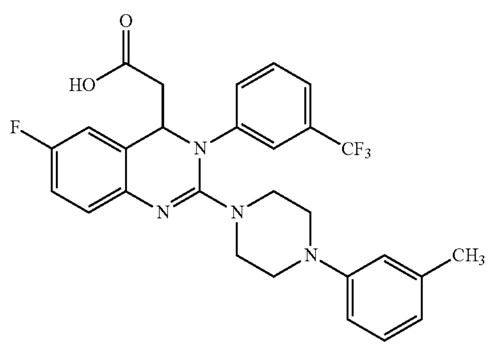 [SMILES: Cc1cccc(N2CCN(C3=Nc4ccc(F)cc4C(CC(=O)O)N3c3cccc(C(F)(F)F)c3)CC2)c1] | 526.5 | 85A | 4.69 | 1 | 527 [M + H]$^+$ |
| 62 | 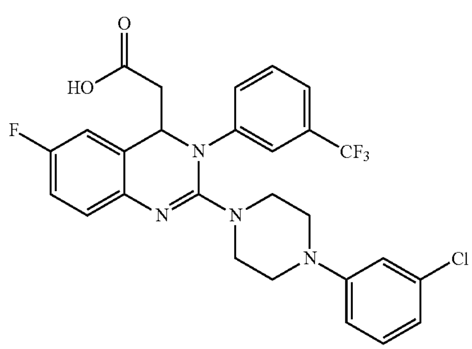 [SMILES: O=C(O)CC1c2cc(F)ccc2N=C(N2CCN(c3cccc(Cl)c3)CC2)N1c1cccc(C(F)(F)F)c1] | 545.0 | 86A | 3.57 | 8 | 547 [M + H]$^+$ |
| 63 | 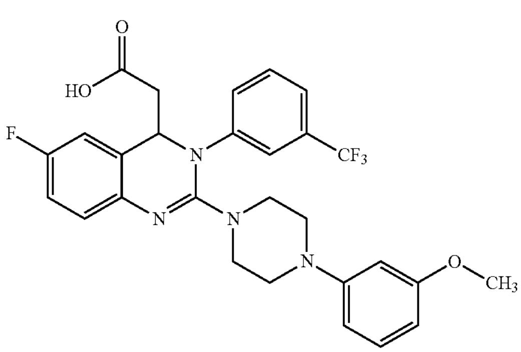 [SMILES: COc1cccc(N2CCN(C3=Nc4ccc(F)cc4C(CC(=O)O)N3c3cccc(C(F)(F)F)c3)CC2)c1] | 542.5 | 87A | 3.37 | 8 | 543 [M + H]$^+$ |

TABLE 2-continued

| Example No. | Structure | Molecular weight [g/mol] | Starting material Example | R$_t$ [min] | HPLC Method | MS |
|---|---|---|---|---|---|---|
| 64 | 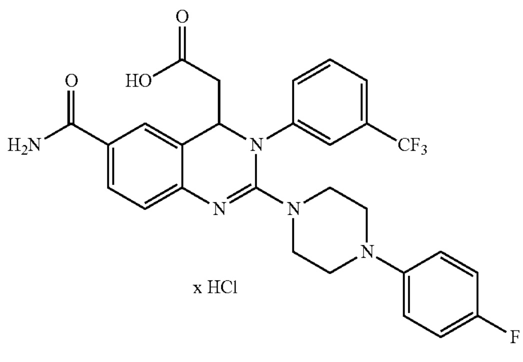 [SMILES: NC(=O)c1ccc2c(c1)C(CC(=O)O)N(c1cccc(C(F)(F)F)c1)C(N1CCN(c3ccc(F)cc3)CC1)=N2] | 574.0 | 88A | 4.43 | 1 | 538 [M + H − HCl]$^+$ |
| 65 | 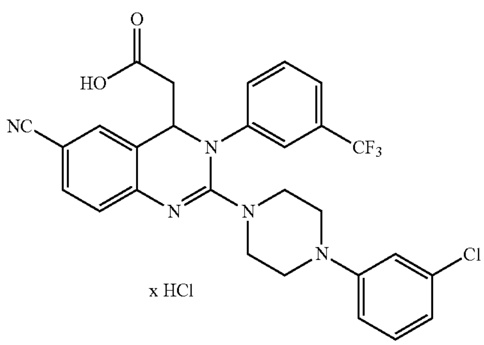 [SMILES: N#Cc1ccc2c(c1)C(CC(=O)O)N(c1cccc(C(F)(F)F)c1)C(N1CCN(c3cccc(Cl)c3)CC1)=N2] | 590.4 | 89A | 4.58 | 1 | 554 [M + H − HCl]$^+$ |
| 66 | 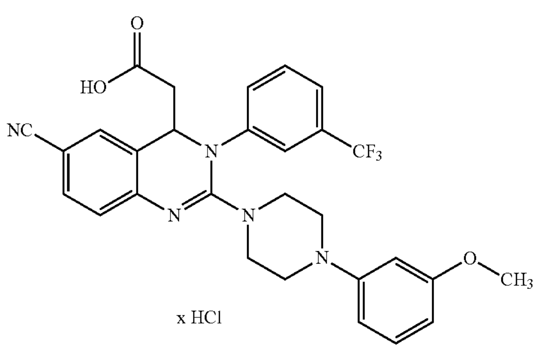 [SMILES: COc1cccc(N2CCN(C3=Nc4ccc(C#N)cc4C(CC(=O)O)N3c3cccc(C(F)(F)F)c3)CC2)c1] | 586.0 | 90A | 4.41 | 1 | 550 [M + H − HCl]$^+$ |
| 67 | 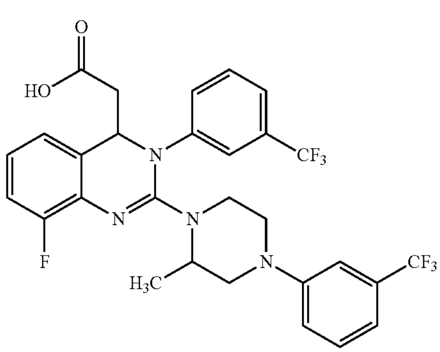 [SMILES: CC1CN(c2cccc(C(F)(F)F)c2)CCN1C1=Nc2c(F)cccc2C(CC(=O)O)N1c1cccc(C(F)(F)F)c1] | 594.5 | 91A | 4.82 | 1 | 595 [M + H]$^+$ |

TABLE 2-continued

| Example No. | Structure | Molecular weight [g/mol] | Starting material Example | R$_t$ [min] | HPLC Method | MS |
| --- | --- | --- | --- | --- | --- | --- |
| 68 | 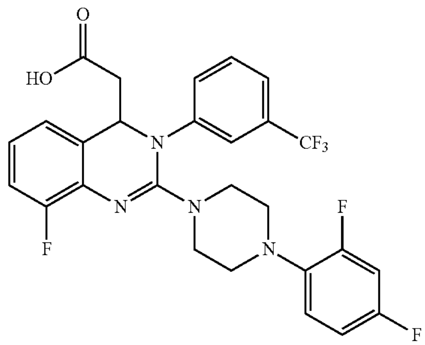 [SMILES: O=C(O)CC1c2cccc(F)c2N=C(N2CCN(c3ccc(F)cc3F)CC2)N1c1cccc(C(F)(F)F)c1] | 548.5 | 92A | 4.66 | 1 | 549 [M + H]$^+$ |
| 69 | 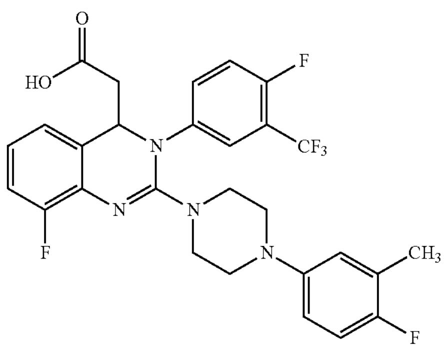 [SMILES: Cc1cc(N2CCN(C3=Nc4c(F)cccc4C(CC(=O)O)N3c3ccc(F)c(C(F)(F)F)c3)CC2)ccc1F] | 562.5 | 93A | 4.74 | 1 | 563 [M + H]$^+$ |
| 70 | 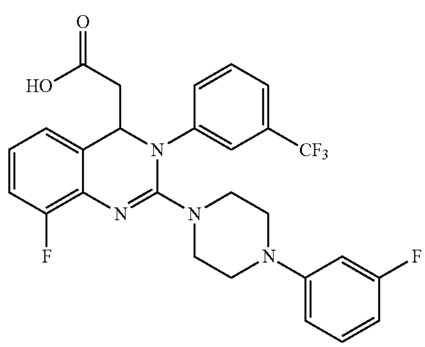 [SMILES: O=C(O)CC1c2cccc(F)c2N=C(N2CCN(c3cccc(F)c3)CC2)N1c1cccc(C(F)(F)F)c1] | 530.5 | 94A | 4.62 | 1 | 531 [M + H]+ |
| 71 | 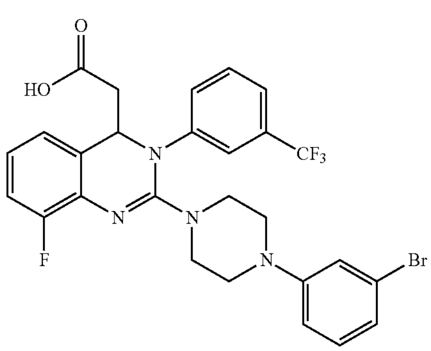 [SMILES: O=C(O)CC1c2cccc(F)c2N=C(N2CCN(c3cccc(Br)c3)CC2)N1c1cccc(C(F)(F)F)c1] | 591.4 | 95A | 4.76 | 1 | 591 [M + H]$^+$ |

TABLE 2-continued

| Example No. | Structure | Molecular weight [g/mol] | Starting material Example | R$_t$ [min] | HPLC Method | MS |
|---|---|---|---|---|---|---|
| 72 | 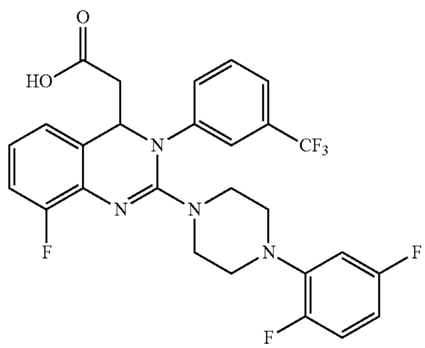 [SMILES: O=C(O)CC1c2cccc(F)c2N=C(N2CCN(c3cc(F)ccc3F)CC2)N1c1cccc(C(F)(F)F)c1] | 548.5 | 96A | 4.63 | I | 549 [M + H]$^+$ |
| 73 | 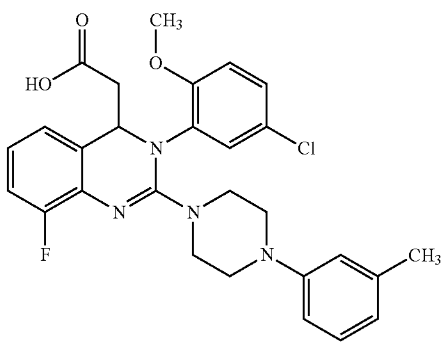 [SMILES: COc1ccc(Cl)cc1N1C(N2CCN(c3cccc(C)c3)CC2)=Nc2c(F)cccc2C1CC(=O)O] | 523.0 | 97A | 4.65 | 1 | 523 [M + H]$^+$ |
| 74 | 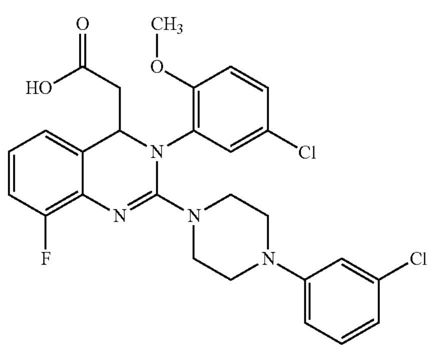 [SMILES: COc1ccc(Cl)cc1N1C(N2CCN(c3cccc(Cl)c3)CC2)=Nc2c(F)cccc2C1CC(=O)O] | 543.4 | 98A | 4.67 | 6 | 543 [M + H]$^+$ |
| 75 | 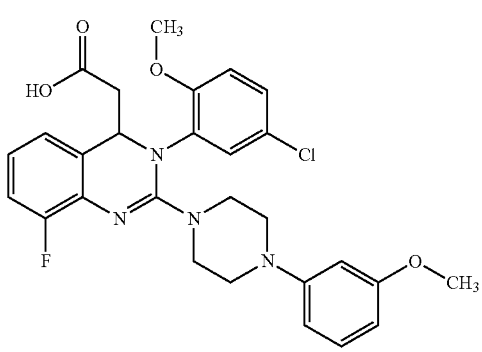 [SMILES: COc1cccc(N2CCN(C3=Nc4c(F)cccc4C(CC(=O)O)N3c3cc(Cl)ccc3OC)CC2)c1] | 539.0 | 99A | 4.56 | 6 | 539 [M + H]$^+$ |

TABLE 2-continued
| Example No. | Structure | Molecular weight [g/mol] | Starting material Example | R_t [min] | HPLC Method | MS |
|---|---|---|---|---|---|---|
| 76 | 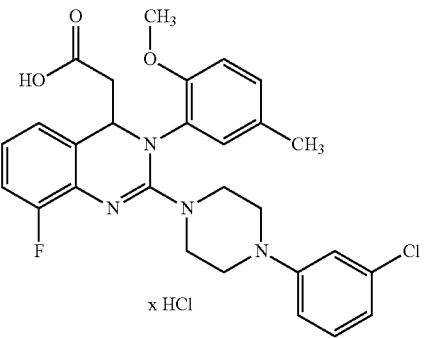 [SMILES: COc1ccc(C)cc1N1C(N2CCN(c3cccc(Cl)c3)CC2)=Nc2c(F)cccc2C1CC(=O)O] x HCl | 559.5 | 100A | 4.63 | 6 | 523 [M + H − HCl]+ |
| 77 | 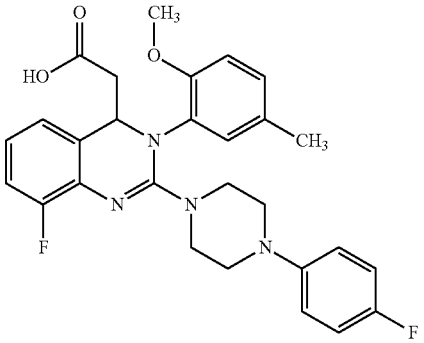 | 506.6 | 101A | 4.52 | 6 | 507 [M + H]+ |
| 78 | 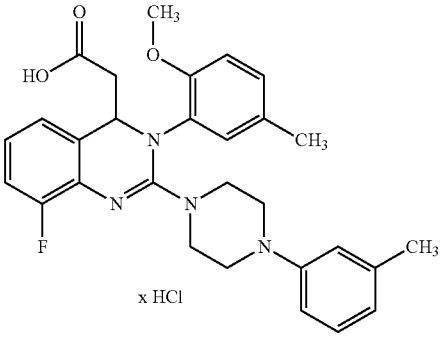 [SMILES: COc1ccc(C)cc1N1C(N2CCN(c3cccc(C)c3)CC2)=Nc2c(F)cccc2C1CC(=O)O] x HCl | 539.0 | 102A | 4.63 | 6 | 503 [M + H − HCl]+ |
| 79 | 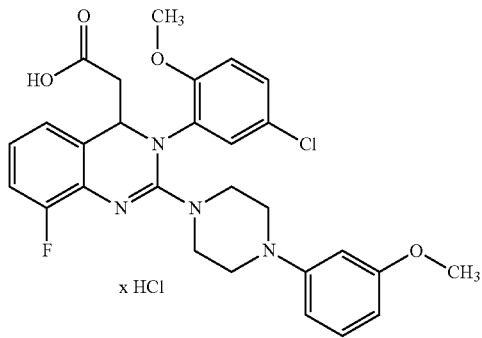 x HCl | 555.0 | 103A | 4.41 | 6 | 519 [M + H − HCl]+ |

TABLE 2-continued

| Example No. | Structure | Molecular weight [g/mol] | Starting material Example | R$_t$ [min] | HPLC Method | MS |
|---|---|---|---|---|---|---|
| 80 | (structure: quinazoline with 8-F, N3-(5-chloro-2-methoxyphenyl), C4-CH2COOH, 2-[4-(4-fluoro-3-methylphenyl)piperazin-1-yl]; x HCl) | 577.5 | 104A | 4.53 | 6 | 541 [M + H − HCl]$^+$ |
| 81 | (structure: quinazoline with 8-F, N3-(4-chloro-2-methoxy-5-methylphenyl), C4-CH2COOH, 2-[4-(4-fluorophenyl)piperazin-1-yl]) | 541.0 | 105A | 4.68 | 1 | 541 [M + H]$^+$ |
| 82 | (structure: quinazoline with 7-CN, N3-(3-trifluoromethylphenyl), C4-CH2COOH, 2-[4-(4-fluorophenyl)piperazin-1-yl]) | 537.5 | 45A | 4.52 | 1 | 538 [M + H]$^+$ |
| 83 | (structure: quinazoline with 7-F, N3-(3-trifluoromethylphenyl), C4-CH2COOH, 2-[4-(4-fluorophenyl)piperazin-1-yl]) | 530.5 | 106A | 4.51 | 1 | 531 [M + H]$^+$ |

TABLE 2-continued

| Example No. | Structure | Molecular weight [g/mol] | Starting material Example | $R_t$ [min] | HPLC Method | MS |
|---|---|---|---|---|---|---|
| 84 | 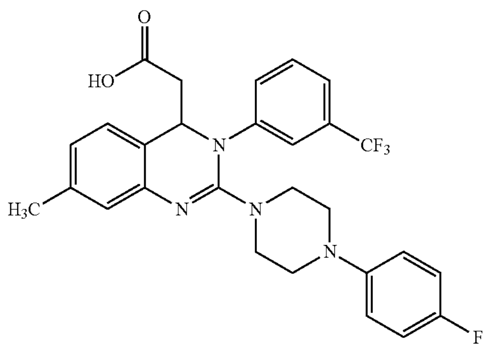 [SMILES: Cc1ccc2c(c1)N=C(N1CCN(c3ccc(F)cc3)CC1)N(c1cccc(C(F)(F)F)c1)C2CC(=O)O] | 526.5 | 107A | 4.70 | 1 | 527 [M + H]$^+$ |
| 85 | x HCl | 583.4 | 108A | 4.61 | 1 | 547 [M + H − HCl]$^+$ |
| 86 | x HCl | 585.0 | 109A | 4.82 | 1 | 549 [M + H − HCl]$^+$ |
| 87 | 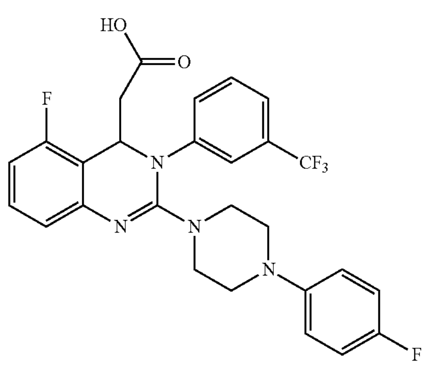 [SMILES: O=C(O)CC1c2c(F)cccc2N=C(N2CCN(c3ccc(F)cc3)CC2)N1c1cccc(C(F)(F)F)c1] | 530.5 | 110A | 4.54 | 1 | 531 [M + H]$^+$ |

TABLE 2-continued

| Example No. | Structure | Molecular weight [g/mol] | Starting material Example | $R_t$ [min] | HPLC Method | MS |
|---|---|---|---|---|---|---|
| 88 | 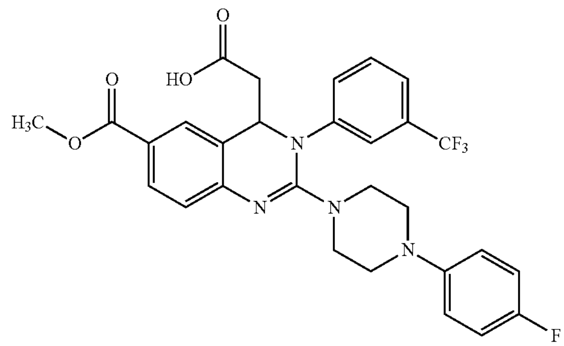 [SMILES: COC(=O)c1ccc2c(c1)C(CC(=O)O)N(c1cccc(C(F)(F)F)c1)C(N1CCN(c3ccc(F)cc3)CC1)=N2] | 570.6 | 111A | 4.54 | 1 | 571 $[M + H]^+$ |
| 89 | 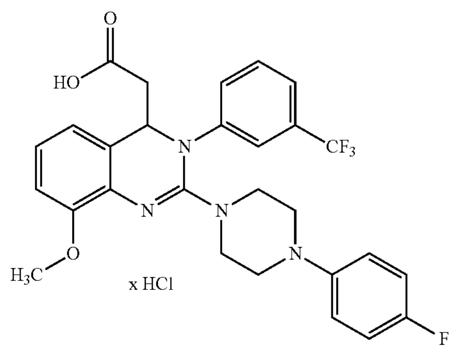 [SMILES: COc1cccc2c1N=C(N1CCN(c3ccc(F)cc3)CC1)N(c1cccc(C(F)(F)F)c1)C2CC(=O)O] | 579.0 | 59A | 4.60 | 1 | 543 $[M + H - HCl]^+$ |

Example 35

{2-[4-(4-Fluorophenyl)piperazin-1-yl]-8-hydroxy-3-[3-(trifluoromethyl)phenyl]-3,4-dihydroquinazolin-4-yl}acetic acid

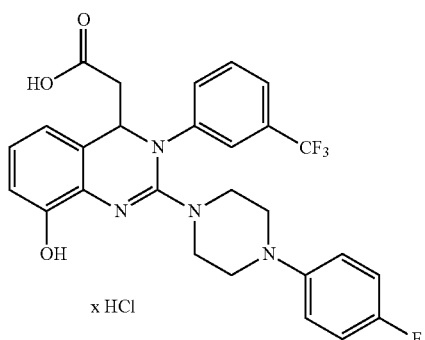

80 mg (0.14 mmol) of the methyl ether (Example 89) are dissolved in 2 ml of dichloromethane, and 0.41 mmol of a 1M solution of boron tribromide in dichloromethane is added at 0° C. The mixture is stirred at room temperature for 16 hours, a further 0.82 mmol of the boron tribromide solution is added, followed by a further 1.23 mmol after 24 hours. The reaction mixture is stirred at room temperature for 24 hours and then poured onto ice, and 5 ml of a 1N aqueous hydrochloric acid solution are added. The mixture is extracted with 25 ml of ethyl acetate. The organic phase is washed with a saturated aqueous sodium chloride solution, dried over sodium sulphate, concentrated and purified by preparative HPLC. This gives 50 mg (63% of theory) of product.

HPLC (Method 1): $R_t$=4.47 min
MS (ESI-pos): m/z=529 (M-1-H—HCl)$^+$

Example 90

{7-Hydroxycarbonyl-2-[4-(4-fluorophenyl)-1-piperazinyl]-3-[5-(trifluoromethyl)phenyl]-3,4-dihydro-4-quinazolinyl}acetic acid

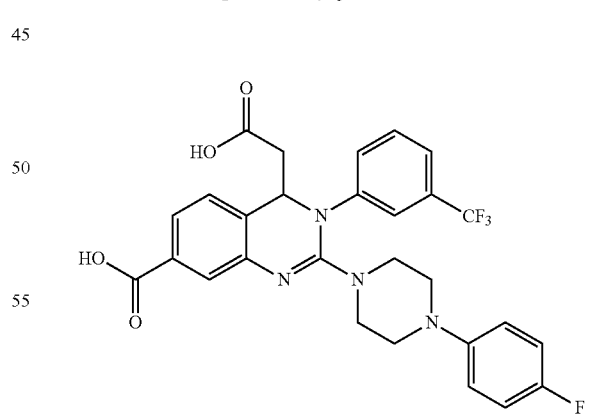

100 mg (0.16 mmol) of the ester from Example 45A are suspended in semiconcentrated hydrochloric acid, and the reaction mixture is stirred at 90° C. for 42 hours. After cooling, the mixture is adjusted to pH=4 using 20% strength aqueous sodium hydroxide solution and the precipitate that is formed is filtered off, washed with water and dried under reduced pressure.

Yield: 64 mg (66% of theory)
HPLC (Method 1): $R_t$=4.38 min
MS (ESI-pos): m/z=557 (M+H)$^+$

Example 91

{6-(Aminocarbonyl)-2-[4-(4-fluorophenyl)piperazin-1-yl]-3-[3-(trifluoromethyl)phenyl]-3,4-dihydroquinazolin-4-yl}acetic acid hydrochloride

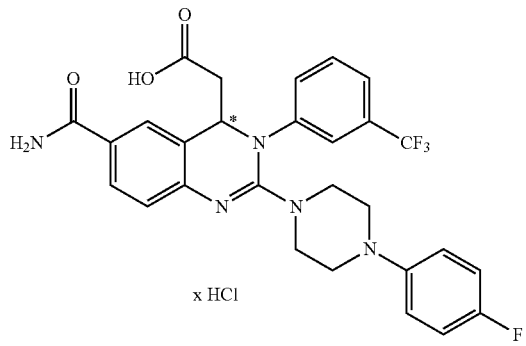 [SMILES: NC(=O)c1ccc2c(c1)C(CC(=O)O)N(c1cccc(C(F)(F)F)c1)C(N1CCN(c3ccc(F)cc3)CC1)=N2]

500 mg (0.8 mmol) of the tert-butyl ester from Example 49A are suspended with 8 ml of a 4M solution of hydrogen chloride in dioxane, and the reaction mixture is stirred at room temperature for 16 hours. The suspension is concentrated and dried under reduced pressure.

Yield: 564 mg (99% of theory)
HPLC (Method 1): $R_t$=4.25 min
MS (ESI-pos): m/z=556 (M+H—HCl)$^+$
$^1$H NMR (300 MHz, DMSO-$d_6$): δ [ppm]=12.94 (brs, 1H); 8.11 (s, 1H); 8.03-7.95 (m, 2H); 7.92-7.65 (m, 4H); 7.09-6.91 (m, 4H); 5.50 (dd, 1H); 4.38-4.12 (m, 4H); 3.17-3.06 (m, 5H); 2.81 (dd, 1H).

B. Assessment of the Physiological Activity

The in vitro effect of the compounds of the invention can be shown in the following assays:

Anti-HCMV (Anti-Human Cytomegalovirus) Cytopathogenicity Tests

The test compounds are employed as 50 millimolar (mM) solutions in dimethyl sulphoxide (DMSO). Ganciclovir®, Foscarnet® and Cidofovir® are used as reference compounds. After addition of in each case 2 µl of the 50, 5, 0.5 and 0.05 mM DMSO stock solutions to 98 µl portions of cell culture medium in row 2 A-H for duplicate determinations, 1:2 dilutions are carried out with 50 µl portions of medium up to row 11 of the 96-well plate. The wells in rows 1 and 12 each contain 50 µl of medium. In 150 µl of a suspension of 1×10$^4$ cells (human prepuce fibroblasts [NHDF]) are pipetted into each of the wells (row 1=cell control) and, in rows 2-12, a mixture of HCMV-infected and uninfected NHDF cells (M.O.I.=0.001-0.002), i.e. 1-2 infected cells per 1000 uninfected cells. Row 12 (without substance) serves as virus control. The final test concentrations are 250-0.0005 µM. The plates are incubated at 37° C./5% $CO_2$ for 6 days, i.e. until all the cells are infected in the virus controls (100% cytopathogenic effect [CPE]). The wells are then fixed and stained by adding a mixture of formalin and Giemsa's dye (30 minutes), washed with double-distilled water and dried in a drying oven at 50° C. The plates are then assessed visually using an overhead microscope (Plaque Multiplier from Technomara).

The following data can be acquired from the test plates:
$CC_{50}$ (NHDF)=substance concentration in µM at which no visible cytostatic effects on the cells are evident by comparison with the untreated cell control;
$EC_{50}$ (HCMV)=substance concentration in µM which inhibits the CPE (cytopathic effect) by 50% compared with the untreated virus control;
SI (selectivity index)=$CC_{50}$ (NHDF)/$EC_{50}$ (HCMV).

Representative in vitro data for the effects of the compounds of the invention are shown in Table A:

TABLE A

| Example No. | NHDF $CC_{50}$ [µM] | HCMV $EC_{50}$ [µM] | SI HCMV |
|---|---|---|---|
| 2 | 12 | 0.016 | 750 |
| 9 | 15 | 0.02 | 750 |
| 15 | 31 | 0.002 | 15500 |
| 19 | 17 | 0.002 | 8947 |
| 23 | 24 | 0.002 | 12632 |
| 29 | 47 | 0.07 | 671 |

The suitability of the compounds of the invention for the treatment of HCMV infections can be shown in the following animal model:

HCMV Xenograft Gelfoam® Model

Animals:

3-4-week old female immunodeficient mice (16-18 g), Fox Chase SCID or Fox Chase SCID-NOD or SCID beige, are purchased from commercial breeders (Taconic M+B, Jackson USA). The animals are housed under sterile conditions (including bedding and feed) in isolators.

Virus Growing:

Human cytomegalovirus (HCMV), Davis or AD169 strain, is grown in vitro on human embryonic prepuce fibroblasts (NHDF cells). After the NHDF cells have been infected with a multiplicity of infection (M.O.I.) of 0.01-0.03, the virus-infected cells are harvested 5-10 days later and stored in the presence of minimal essential medium (MEM), 10% fetal calf serum (FCS) with 10% DMSO at −40° C. After serial ten-fold dilutions of the virus-infected cells, the titer is determined on 24-well plates of confluent NHDF cells after vital staining with Neutral Red.

Preparation of the Sponges, Transplantation, Treatment and Evaluation:

Collagen sponges 1×1×1 cm in size (Gelfoam®; from Peasel & Lorey, order No. 407534; K. T. Chong et al., Abstracts of 39$^{th}$ Interscience Conference on Antimicrobial Agents and Chemotherapy, 1999, p. 439) are initially wetted with phosphate-buffered saline (PBS), the trapped air bubbles are removed by degassing, and then stored in MEM+10% FCS. 1×10$^6$ virus-infected NHDF cells (infection with HCMV Davis or HCMV AD169 M.O.I.=0.01) are detached 3 hours after infection and added in a drop of 20 µl of MEM, 10% of FCS, to a moist sponge. About 16 hours later, the infected sponges are incubated with 25 µl of PBS/0.1% BSA/1 mM DTT with 5 ng/µl basic fibroblast growth factor (bFGF). For the transplantation, the immunodeficient mice are anaesthetized with Avertin or a ketamine/xylazine/azepromazine mixture, the fur on the back is removed using a shaver, the epidermis is opened 1-2 cm, unstressed and the moist sponges are transplanted under the dorsal skin. The surgical wound is closed with tissue glue. 6 hours after the transplantation, the mice can be treated for the first time (on the day of the operation, there is one treatment). The next days, over a period of 8 days, the mice are treated with substance orally three times a day (7.00 h and 14.00 h and 19.00 h), two times a day (8.00 h and 18.00 h) or once a day (14.00 h). The daily dose is, for example 3 or 10 or 30 or 60 or 100 mg/kg of body weight, the volume administered is 10 ml/kg of body weight. The substances are formulated in the form of a 0.5% strength Tylose suspension with 2% DMSO or a 0.5% strength Tylose suspension. 9 days after transplantation and 16 hours after the last administration of substance, the animals are painlessly sacrificed and the sponge is removed. The virus-infected cells are released from the sponge by collagenase digestion (330 U/1.5 ml) and stored in the presence of MEM, 10% fetal calf serum, 10% DMSO at −140° C. Evaluation takes place after serial ten-fold dilutions of the virus-infected cells by determining the titer on 24-well plates of confluent NHDF cells after vital staining with Neutral Red. The number of infected cells or infectious virus particles (infectious centre assay) after the substance treatment compared with the placebo-treated control is determined.

CYP Inhibition Assay

To investigate the mechanism-based (irreversible) inhibition of CYP3A4, different concentrations of the test substance are incubated with human liver microsomes (2 mg/ml of microsomal protein) in potassium phosphate buffer pH 7.4 with addition of an NADPH-generating system (NADP+, glucose 6-phosphate, glucose 6-phosphate dehydrogenase) at 37° C. At various points of time, 2 aliquots are taken from the incubation.

The first aliquot is incubated 1:50 in a new incubation solution (phosphate buffer, NADPH-generating system and 10 μM of Midazolam) at 37° C. for a further 10 min. The incubation is then stopped using acetonitrile on ice, the protein is pelleted in a centrifuge at 15 000 g and the supernatant is analysed for formation of 1'-hydroxyimidazolam using standard HPLC/MS methods.

The second aliquot is stopped using acetonitrile on ice and analysed for remaining test substance using HPLC/UV/MS.

The two sets of analytical data are determined for irreversible-inhibition-typical parameters ($k_{inact}$, $K_i$ and partition ratio r), and using these data, the test substance is evaluated (cf. A. Madan, et al., in A. D. Rodrigues (ed.) "Drug-Drug Interaction" in "Drugs and the Pharmaceutical Science", Vol. 116, ISBN 0-8247-0283.2, Marcel Dekker Inc., New York, 2002.).

C. Exemplary Embodiments pf Pharmaceutical Compositions

The compounds of the invention can be converted into pharmaceutical preparations in the following ways:

Tablet:
Composition:
100 mg of the compound of Example 1, 50 mg of lactose (monohydrate), 50 mg of corn starch (native), 10 mg of polyvinylpyrrolidone (PVP 25) (from BASF, Ludwigshafen, Germany) and 2 mg of magnesium stearate.

Tablet weight 212 mg. Diameter 8 mm, radius of curvature 12 mm.

Production:
The mixture of active ingredient, lactose and starch is granulated with a 5% strength solution (m/m) of the PVP in water. The granules are then dried and mixed with the magnesium stearate for 5 min. This mixture is compressed using a conventional tablet press (see above for format of the tablet). A guideline for the compressive force used for the compression is 15 kN.

Suspension which can be Administered Orally:
Composition:
1000 mg of the compound of Example 1, 1000 mg of ethanol (96%), 400 mg of Rhodigel (xanthan gum from FMC, Pennsylvania, USA) and 99 g of water.

10 nil of oral suspension are equivalent to a single dose of 100 mg of the compound of the invention.

Production:
The Rhodigel is suspended in ethanol, and the active ingredient is added to the suspension. The water is added while stirring. The mixture is stirred for about 6 h until the swelling of the Rhodigel is complete.

Solution which can be Administered Intravenously:
Composition:
10-500 mg of the compound of Example 1, 15 g of polyethylene glycol 400 and 250 g of water for injection.

Production:
The compound of Example 1 is dissolved together with polyethylene glycol 400 in the water with stirring. The solution is sterilized by filtration (pore diameter 0.22 μm) and dispensed under aseptic conditions into heat-sterilized infusion bottles. The latter are closed with infusion stoppers and trimmed caps.

The invention claimed is:

1. A compound of formula (I):

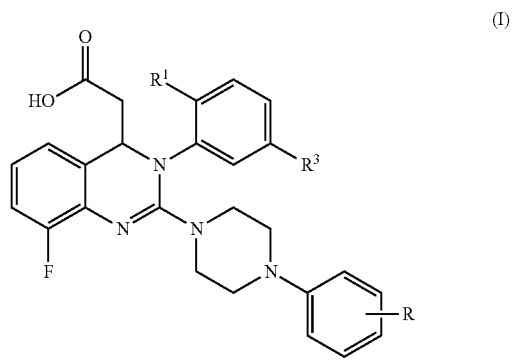

in which
R¹ represents hydrogen or methoxy;
R³ represents halogen or trifluoromethyl; and
R represents halogen or methoxy;
or a salt thereof.

2. The compound of claim 1, wherein R³ represents fluorine, chlorine or trifluoromethyl; or a salt thereof.

3. The compound of claim 1, wherein R represents fluorine, chlorine or methoxy; or a salt thereof.

4. The compound of claim 1, wherein R is attached to the phenyl ring via the position meta or para to the point of attachment of the phenyl ring; or a salt thereof.

5. A compound {8-Fluoro-2-[4-(3-methoxyphenyl)piperazin-1-yl]-3-(2-methoxy-5-trifluoromethylphenyl)-3,4-dihydroquinazolin-4-yl}acetic acid, or a salt thereof.

6. A compound (S)-{8-Fluoro-2-[4-(3-methoxyphenyl)piperazin-1-yl]-3-(2-methoxy-5-trifluoromethylphenyl)-3,4-dihydroquinazolin-4-yl}acetic acid, or a salt thereof.

7. A process for preparing a compound of formula (I) according to claim 1, wherein a compound of formula (II):

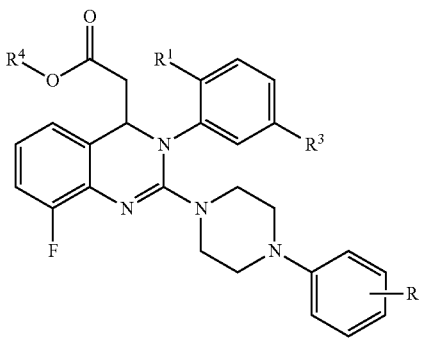

(II)

in which

R¹, R³ and R are as defined in claims 1; and

R⁴ represents alkyl;

is reacted with an acid or a base.

8. The process of claim 7, wherein R⁴ is methyl, ethyl or tert-butyl.

9. A medicament comprising a compound of claim 1, a compound of claim 5, or a compound of claim 6 in combination with at least one inert, non toxic, pharmaceutically acceptable excipient.

10. A method for the production of a medicament for the treatment of viral infections, comprising mixing a compound of claim 1, a compound of claim 5, or a compound of claim 6 with at least one inert, non toxic, pharmaceutically acceptable excipient.

11. The method of claim 10, wherein the viral infection is an infection with the human cytomegalovirus (HCMV) or another representative of the group of the Herpes viridae.

12. A method for treating infections HO—C(=O)—CH₂— at the 4-position; in humans and animals, comprising administering an antivirally effective amount of a compound of claim 1, a compound of claim 5, or a compound of claim 6, to a human or animal in need thereof.

13. A method for treating infections HO—C(=O)—CH₂— at the 4-position; in humans and animals, comprising administering an antivirally effective amount of a medicament of claim 9 to a human or animal in need thereof.

* * * * *